US011529345B2

(12) United States Patent
Hille et al.

(10) Patent No.: US 11,529,345 B2
(45) Date of Patent: Dec. 20, 2022

(54) BUPRENORPHINE TRANSDERMAL DELIVERY SYSTEM

(71) Applicant: LTS LOHMANN THERAPIE-SYSTEME AG, Andernach (DE)

(72) Inventors: Thomas Hille, Neuwied (DE); Gabriel Wauer, Bad Neuenahr-Ahrweiler (DE); Frank Seibertz, Bad Breisig (DE); Shu-Lun Weinheimer, Livingston, NJ (US)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 16/844,767

(22) Filed: Apr. 9, 2020

(65) Prior Publication Data
US 2020/0237748 A1  Jul. 30, 2020

Related U.S. Application Data

(63) Continuation of application No. 15/414,138, filed on Jan. 24, 2017, now abandoned, which is a continuation of application No. 14/772,474, filed as application No. PCT/EP2014/061567 on Jun. 4, 2014, now abandoned.

(60) Provisional application No. 61/830,975, filed on Jun. 4, 2013.

(51) Int. Cl.
*A61K 31/4748* (2006.01)
*A61K 31/485* (2006.01)
*A61K 9/70* (2006.01)
*A61F 13/02* (2006.01)
*A61K 9/00* (2006.01)
*A61K 47/12* (2006.01)
*A61K 47/32* (2006.01)

(52) U.S. Cl.
CPC ...... *A61K 31/4748* (2013.01); *A61F 13/0256* (2013.01); *A61K 9/0014* (2013.01); *A61K 9/7053* (2013.01); *A61K 9/7069* (2013.01); *A61K 31/485* (2013.01); *A61K 47/12* (2013.01); *A61K 47/32* (2013.01)

(58) Field of Classification Search
CPC .............. A61K 31/4748; A61K 9/0014; A61K 9/7053; A61K 9/7069; A61K 31/485; A61F 13/0256
See application file for complete search history.

(56) References Cited

U.S. PATENT DOCUMENTS

| 3,433,791 | A | 3/1969 | Bentley |
| 4,588,580 | A | 5/1986 | Gale |
| 4,806,341 | A | 2/1989 | Chien |
| 5,069,909 | A | 12/1991 | Sharma et al. |
| 5,240,711 | A | 8/1993 | Hille et al. |
| 5,788,983 | A | 8/1998 | Chien et al. |
| 5,968,547 | A | 10/1999 | Reder |
| 6,264,980 | B1 | 7/2001 | Hille et al. |
| 6,344,212 | B2 | 2/2002 | Reder |
| 6,365,178 | B1* | 4/2002 | Venkateshwaran ......... A61K 9/7053 424/447 |
| 6,783,769 | B1 | 8/2004 | Arth et al. |
| 7,390,500 | B2 | 6/2008 | Muller |
| 9,289,397 | B2 | 3/2016 | Wright |
| 9,308,202 | B2 | 4/2016 | Hille et al. |
| 2001/0002259 | A1* | 5/2001 | Reder .................. A61K 9/0014 424/422 |
| 2004/0081685 | A1 | 4/2004 | Wright |
| 2004/0126416 | A1 | 7/2004 | Reidenberg |

(Continued)

FOREIGN PATENT DOCUMENTS

CA    2374930        8/2008
DE    39 39 376 C1   5/1991

(Continued)

OTHER PUBLICATIONS

Chien "Transdermal Controlled System Medications", Marcel Dekker Inc., 1987, pp. 36-45.
European Pat. Appln. No. 14 171 110.1 (Pub. No. 2 810 646) (corresponds to PCT Application No. PCDEP2014/061567) - Response to Third Party Submission dated Jun. 12, 2015.
European Pat Appln. 12 826 670.7 (based on PCT Application No. PCT/IB2012/002973)—Third party submission dated May 24, 2015.
European Pat. Appln. No. 14 171 110.1 (Pub. No. 2 810 646) (corresponds to PCT Application No. PCT/EP2014/061567)—Third Party Submission dated May 8, 2015.
European Pat. Appln. No. 14 171 110.1 (Pub. No. 2 810 646) (corresponds to PCT Application No. PCT/EP2014/061567)—Communication re: European Search Report dated Aug. 21, 2014.

(Continued)

*Primary Examiner* — Michael B. Pallay
(74) *Attorney, Agent, or Firm* — Jones Day

(57) ABSTRACT

A transdermal therapeutic system for the transdermal administration of buprenorphine comprising a buprenorphine-containing self-adhesive layer structure having (A) a buprenorphine-impermeable backing layer, and (B) a buprenorphine-containing pressure-sensitive adhesive layer on the backing layer. The buprenorphine-containing adhesive layer comprises (a) at least one polymer-based pressure-sensitive adhesive, (b) an analgesically effective amount of buprenorphine base or a pharmaceutically acceptable salt thereof, (c) a viscosity-increasing substance in an amount of about 0.1% to about 8% of the buprenorphine-containing pressure-sensitive adhesive layer, and (d) a carboxylic acid selected from oleic acid, linoleic acid, linolenic acid, levulinic acid and mixtures thereof. The amount of the carboxylic acid is sufficient so that the analgesically effective amount of buprenorphine is solubilized in the carboxylic acid to form a mixture including the viscosity-increasing substance. This mixture forms dispersed deposits in the pressure-sensitive adhesive. The buprenorphine-containing pressure-sensitive adhesive layer is the skin contact layer.

48 Claims, 9 Drawing Sheets

(56) References Cited

U.S. PATENT DOCUMENTS

| | | | |
|---|---|---|---|
| 2004/0202707 A1* | 10/2004 | Muller | A61K 31/165 424/449 |
| 2004/0202710 A1* | 10/2004 | Muller | A61K 9/7069 424/449 |
| 2004/0219196 A1 | 11/2004 | Hart et al. | |
| 2004/0228906 A1 | 11/2004 | Bartholomaeus | |
| 2004/0234583 A1 | 11/2004 | Muller | |
| 2004/0253301 A1 | 12/2004 | Hille et al. | |
| 2005/0118245 A1 | 6/2005 | Wilsmann | |
| 2005/0191340 A1 | 9/2005 | Bartholomaeus | |
| 2005/0232964 A1 | 10/2005 | Fennimore, Jr. | |
| 2006/0148364 A1 | 7/2006 | Pohlmann | |
| 2006/0198881 A1 | 9/2006 | Howard et al. | |
| 2007/0065365 A1 | 3/2007 | Kugelmann et al. | |
| 2008/0113013 A1 | 5/2008 | Koch | |
| 2008/0274167 A1 | 11/2008 | Muller | |
| 2009/0124953 A1 | 5/2009 | Nakahara et al. | |
| 2009/0258062 A1 | 10/2009 | Horstmann et al. | |
| 2010/0112064 A1 | 5/2010 | Hille et al. | |
| 2010/0119585 A1* | 5/2010 | Hille | A61M 37/00 424/449 |
| 2011/0288112 A1 | 11/2011 | Reder et al. | |
| 2014/0363487 A1 | 12/2014 | Hille | |
| 2015/0306093 A1 | 10/2015 | Wauer | |
| 2015/0374642 A1 | 12/2015 | Ogino et al. | |
| 2016/0008294 A1 | 1/2016 | Hille et al. | |
| 2016/0120823 A1 | 5/2016 | Hille et al. | |
| 2016/0175447 A1 | 6/2016 | Hille et al. | |

FOREIGN PATENT DOCUMENTS

| | | |
|---|---|---|
| DE | 199 58 554 A1 | 1/2001 |
| DE | 10 2004 062 647 A1 | 6/2006 |
| DE | 10 2004 062 614 A1 | 7/2006 |
| EP | 0 368 409 A2 | 5/1990 |
| EP | 0 430 019 A2 | 6/1991 |
| EP | 0 430 019 B1 | 3/1996 |
| EP | 1 572 167 A1 | 9/2005 |
| EP | 0 964 677 B1 | 8/2006 |
| EP | 1 731 152 A2 | 12/2006 |
| EP | 2366388 A1 | 9/2011 |
| GB | 1136214 | 12/1968 |
| JP | 2000-511936 A | 9/2000 |
| JP | 2003-503445 | 1/2003 |
| JP | 2003-522144 | 7/2003 |
| JP | 2005-518354 A | 6/2005 |
| JP | 2009-539786 A | 11/2009 |
| JP | 2010-510259 A | 4/2010 |
| JP | 2012-500787 A | 1/2012 |
| RU | 2251413 | 5/2005 |
| RU | 2005132834 A | 4/2006 |
| WO | WO 96/19975 | 7/1996 |
| WO | WO 1998/36728 A | 8/1998 |
| WO | WO 01/01967 | 1/2001 |
| WO | WO 01/01967 A1 | 1/2001 |
| WO | WO 01/58447 | 8/2001 |
| WO | WO 2003/018071 | 3/2003 |
| WO | WO 03/043657 A1 | 5/2003 |
| WO | WO 2003/079962 | 10/2003 |
| WO | WO 2004/014336 A | 2/2004 |
| WO | WO 2004/054553 A1 | 7/2004 |
| WO | WO 2002/41878 | 5/2005 |
| WO | WO 2006/030030 | 3/2006 |
| WO | WO 2008/061625 A2 | 5/2008 |
| WO | WO 2010/020794 A1 | 2/2010 |
| WO | WO 2012/065740 A1 | 5/2012 |
| WO | WO 2014/195352 A1 | 12/2014 |

OTHER PUBLICATIONS

*Fachinformation* TRANSTEC, 2001, Bundesverband der Pharmazeutishen Inudtrie e.V. (in German w/ English translation).

*Gebrauchsinformation: Information für den Anwender, Transtec 35 Mikrogramm/h—transdermales Pflaster, Version 5.0m* Nov. 18, 2010 (in German with English translation of p. 8, last paragraph (item6) to p. 9, first paragraph of the Summary of Product Characteristics of Transtec 35 micrograms/hr (Transtec SPC)).
Highlights of Prescribing Information—Butrans (buprenorphine) Transdermal System—Aug. 2010.
Highlights of Prescribing Information—Butrans (buprenorphine) Transdermal System—Jun. 2010.
Kandavilli, S. "Polmers n Transdermal Drug Delivery Systems", *Pharmaceutical Technology*, May 2002, pp. 62-80.
Merck Index "An encyclopedia of chemicals, drugs, and biological",15th Edition, p. 264 (buprenorphine).
Napp Pharmaceuticals Limited, BuTrans 5, 10 and 20 ug/h Transdermal Patch—Summary of Product Characteristics, Mar. 11, 2010.
PCT Application No. PCT/EP2007/09622—International Preliminary Report on Patentability (IPRP) and Written Opinion of IPRP (WO-IPRP) from EPO as International Search Authority (in German) dated Jun. 10, 2009 (with English translation).
PCT Application No. PCT/EP2007/09622—International Search Report dated Jul. 18, 2008.
PCT Application No. PCT/EP2013/076325—International Search Report (ISR) and Written Opinion from EPO as International Search Authority dated May 13, 2014.
PCT Application No. PCT/EP2013/076325—International Preliminary Report on Patentability dated Jun. 16, 2015 with Written Opinion from EPO as International Search Authority.
PCT Application No. PCT/EP2014/061567—International Search Report (ISR) and Written Opinion from EPO as International Search Authority dated Aug. 21, 2014.
PCT Application No. PCT/IB2012/002973—International Preliminary Report on Patentability (IPRP) and Written Opinion from EPO as International Search Authority, dated Jun. 17, 2014.
Posker, GL "Buprenorphine 5, 10 and 20 μg/h Transdermal Patch—A review of Its Use in the Management of Chronic Non-Malignant Pain," Adis International Ltd, , Drugs, Dec. 1, 2011, 71(18) 2491-2509.
Transdermanye terapevti' cheskie sistemy (Transdermal Therapeutic System), http://medi.ru/doc/991011.htm, 2001 (in Russion with English translation).
Transtec 35, 52.5 and 70 micrograms transdermal patch—Summary of Product Characteristics, Nov. 10, 2014.
PCT Application No. PCT/EP2007/09622—International Preliminary Report on Patentability (IPRP) and Written Opinion of ISA dated Jun. 10, 2009.
Roy et al., "Transdermal Delivery of Buprenorphine through Cadaver Skin", Journal of Pharmaceutical Sciences, vol. 83, No. 2 Feb. 1994, pp. 126-130.
Rustan et al., "Fatty Acids: Structures and Properties", Encyclopedia of Life Sciences 2005, John Wiley & Sons, pp. 1-7.
Chilean Appln. No. 001559-2014—Notification of Oppositions dated Jan. 23, 2015 (in Spanish with English translation).
Chilean Appln. No. 001559-2014—Opposition dated Dec. 2, 2014 by Asociacion Industrial de Laboratorios Farmaceuticos AG (in Spanish with English translation).
Chilean Appln. No. 001559-2014—Opposition dated Dec. 9, 2014 by Laboratorios Recalcine SA (in Spanish with English translation).
Chilean Appln. No. 001559-2014—Response with attachments dated Mar. 23, 2015 to Oppositions by Asociacion Industrial de Laboratorios Farmaceuticos AG and Laboratorios Recalcine SA (in Spanish with English translation of Response).
Colombian Appln. No. 14.149.730—Opposition by Laboratorio Franco Colombiano SAS Lafrancol SAS, publication in Gazette 700 dated Jul. 21, 2014 (in Spanish with English translation).
Colombian Appln. No. 14.149.730—Response dated Jan. 21, 2015 to Opposition by Laboratorio Franco Colombiano SAS Lafrancol SAS (in Spanish with English translation).
Correa, Carlos, "Pautas para el examen de patentes farmaceuticas. Una perspectiva desde Ia Salud Publica" ("Guidelines for the examination of pharmaceutical patents" Developing a public health perspective), Universidad de Buenos Aires, Mar. 2008 (in Spanish with English translation of Foreword, pp. vii-viii).
ROMPP Online, Version 3.27, "Emulsionen", Sep. 6, 2012, Angsgar Behler (ed.) (in German with English translation).

(56) References Cited

OTHER PUBLICATIONS

Falbe, J., ROMPP Chemie Lexikon, (1990), Georg Thieme Verlag Stuttgart, pp. 1158-1159 (in German with English translation).
Liao, et al., "In Vitro Skin Permeation of Buprenorphine Transdermal Patch," J. Food and Drug Analysis, vol. 16, No. 6 (2008) pp. 8-15.
Indian Patent Appln. No. 2662/CHENP/2009—Pre-Grant Opposition dated Jan. 8, 2016 by Indian Pharmaceutical Alliance.
Chilean Patent Appln. No. 2015-001577—Pre-Grant Opposition dated Feb. 9, 2016 by Asociacion Industrial de Laboratorios Farmaceuticos AG (ASILFA) (in Spanish with English translation).
Chilean Patent Appln. No. 2015-001577—Applicant's Response dated Apr. 12, 2016 to Pre-Grant Opposition by Asociacion Industrial de Laboratorios Farmaceuticos AG (ASILFA) with Amended Claims (in Spanish with English translation).
Opposition of EP 2790685, Notice of Opposition submitted by Luye Supply AG (Opponent 1) on May 15, 2018.
Opposition of EP 2790685, Exhibit D1—US Publication 2010/0119585, submitted May 15, 2018 with the Notice of Opposition by Luye Supply AG.
Opposition of EP 2790685, Exhibit D2—German Patent DE 10 2006 054 732, submitted May 15, 2018 with the Notice of Opposition by Luye Supply AG.
Opposition of EP 2790685, Exhibit D3—PCT Publication WO 98/36728, submitted May 15, 2018 with the Notice of Opposition by Luye Supply AG.
Opposition of EP 2790685, Exhibit D4—PCT Publication WO 2006/030030, submitted May 15, 2018 with the Notice of Opposition by Luye Supply AG.
Opposition of EP 2790685, Exhibit D5—PCT Publication WO 03/079962, submitted May 15, 2018 with the Notice of Opposition by Luye Supply AG.
Opposition of EP 2790685, Notice of Opposition submitted by Pajaro Limited (Opponent 2) on May 16, 2018.
Opposition of EP 2790685, Exhibit N1—EP 2790685 B1, submitted May 16, 2018 with the Notice of Opposition by Pajaro Limited.
Opposition of EP 2790685, Exhibit N2—Patentee's (applicant's) submission in the examination proceedings dated Jun. 16, 2016, submitted May 16, 2018 with the Notice of Opposition by Pajaro Limited.
Opposition of EP 2790685, Exhibit N3—Patentee's (applicant's) submission in the examination proceedings dated Feb. 13, 2015, submitted May 16, 2018 with the Notice of Opposition by Pajaro Limited.
Opposition of EP 2790685, Exhibit N4—Patentee's (applicant's) submission in the examination proceedings dated Dec. 22, 2016, submitted May 16, 2018 with the Notice of Opposition by Pajaro Limited.
Opposition of EP 2790685, Exhibit N5—Microscope inages of the (buprenorphine-containing) matrix layer of the commercial Norspang® system, submitted May 16, 2018 with the Notice of Opposition by Pajaro Limited.
Opposition of EP 2790685, Exhibit N6—Patentee's (applicant's) submission in the examination proceedings dated Oct. 22, 2015, submitted May 16, 2018 with the Notice of Opposition by Pajaro Limited.
Opposition of EP 2790685, Exhibit D1—US Publication 2010/0119585 (published on May 13, 2010), submitted May 16, 2018 with the Notice of Opposition by Pajaro Limited.
Opposition of EP 2790685, Exhibit D2—US Publication 2010/0112064 (published on May 6, 2010), submitted May 16, 2018 with the Notice of Opposition by Pajaro Limited.
Opposition of EP 2790685, Exhibit D3—Liao, C. L. Journal of Food and Drug Analysis 2008, 16, 8-15, submitted May 16, 2018 with the Notice of Opposition by Pajaro Limited.
Opposition of EP 2790685, Exhibit D4—PCT Publication WO98/36728 A2 (published on Aug. 27, 1998), submitted May 16, 2018 with the Notice of Opposition by Pajaro Limited.
Opposition of EP 2790685, Exhibit D5—PCT Publication 96/19975 (published on Jul. 4, 1996), submitted May 16, 2018 with the Notice of Opposition by Pajaro Limited.
Opposition of EP 2790685, Exhibit D6—Declaration of Thomas Hille, submitted May 16, 2018 with the Notice of Opposition by Pajaro Limited.
Opposition of EP 2790685, Notice of Opposition submitted by Hexal AG (Opponent 3) on May 16, 2018.
Opposition of EP 2790685, Exhibit TM1—Note for guidance on modified release oral and transdermal dosage forms: Section II (Pharmacokinetic and Clinical Evaluation) dated Jul. 28, 1999, submitted May 16, 2018 with the Notice of Opposition by Hexal AG.
Opposition of EP 2790685, Exhibit TM2—US Publication 2010/0119585 (published on May 13, 2010), submitted May 16, 2018 with the Notice of Opposition by Hexal AG.
Opposition of EP 2790685, Exhibit TM3—*European Pharmacopoeia*, 5th Ed., 2005, submitted May 16, 2018 with the Notice of Opposition by Hexal AG.
Opposition of EP 2790685, Exhibit TM4—US Publication 2008/0274167 (published on Nov. 6, 2008), submitted May 16, 2018 with the Notice of Opposition by Hexal AG.
Opposition of EP 2790685, Notice of Opposition submitted by Swindell & Pearson Limited (Opponent 4) on May 16, 2018.
Opposition of EP 2790685, Exhibit SP1,—U.S. Pat. No. 6,264,980 (granted on Jul. 24, 2001), submitted May 16, 2018 with the Notice of Opposition by Swindell & Pearson Limited.
Opposition of EP 2790685, Exhibit SP2—PCT Publication WO1998036728 (published on Aug. 27, 1998), submitted May 16, 2018 with the Notice of Opposition by Swindell & Pearson Limited.
Opposition of EP 2790685, Exhibit SP3—U.S. Pat. No. 5,069,909 (granted on Dec. 3, 1991), submitted May 16, 2018 with the Notice of Opposition by Swindell & Pearson Limited.
Opposition of EP 2790685, Exhibit SP4—US Publication 2010119585 (granted on May 13, 2010), submitted May 16, 2018 with the Notice of Opposition by Swindell & Pearson Limited.
Opposition of EP 2790685, Exhibit SP5—U.S. Pat. No. 5,240,711 (granted on Aug. 31, 1993), submitted May 16, 2018 with the Notice of Opposition by Swindell & Pearson Limited.
Opposition of EP 2790685, Patentee's response to the Notices of Opposition by Opponents 1-4 on Oct. 5, 2018.
Opposition of EP 2790685, Exhibit P1—Chien, Y.W. Ed. 1987, "Transdermal Controlled Systemic Medications", Marcel Dekker Inc., V. 31 pp. 36-45, submitted Oct. 5, 2018 with the Patentee's Reply.
Opposition of EP 2790685, Exhibit P2—Microscopic image of a 23 μm PET backing film, submitted Oct. 5, 2018 with the Patentee's Reply.
Opposition of EP 2790685, Exhibit P3—Microscopic image of the commercial Norspan® system, submitted Oct. 5, 2018 with the Patentee's Reply.
Opposition of EP 2790685, Exhibit P4—Microscopic image of the buprenorphine-containing matrix layer of the commercial Norspan® system with mechanically removed adhesive overlay, submitted Oct. 5, 2018 with the Patentee's Reply.
Opposition of EP 2790685, Exhibit P5—Microscopic image of the buprenorphine-containing pressure-sensitive adhesive layer containing dispersed deposits according to the contested patent, submitted Oct. 5, 2018 with the Patentee's Reply.
Opposition of EP 2790685, Exhibit P6—Microscopic image of a film of 10% by weight levulinic acid in 90% by weight polyisobutylene, submitted Oct. 5, 2018 with the Patentee's Reply.
McQuinn et al., 1995, "Sustained oral mucosal delivery in human volunteers of buprenorphine from a thin non-eroding mucoadhesive polymeric disk". J. of Controlled. Release 34:243-250.
Highlights of Prescribing Information of Butrans (buprenorphine) Transdermal System for transdermal administration, revised Jun. 2011 (32 pages).
European Pat. Appln. No. 16173124.5 (Pub. No. 3106153) (corresponds to PCT Application No. PCT/EP2014/061567)—Communication re: European Search Report dated Oct. 24, 2016 (13 pages).

(56) References Cited

OTHER PUBLICATIONS

Opposition to EP 2790685—Preliminary Decision dated Apr. 17, 2019 (15 pages).
Mehrotra et al. Time Controlled Release of Arabinofuranosylcytosine (Ara-C) from Agarose Hydrogels using Layer-by-Layer Assembly: An In Vitro Study, J Biomater Sci Polym Ed. 2012, 23 (0) (27 pages).
AGAH working group Pharmacokinetics, "Collection of terms, symbols, equations, and explanations of common pharmacokinetic and pharmacodynamics parameters and sonic statistical functions", Feb. 2004 (23 pages).
PermeGear, "Equipment that measures permeation through membranes," http://permegear.com/franz.htm dated Jul. 23, 2015 (4 pages).
"Transtec 35, 52.5 and 70 micrograms transdermal patch", https://www.medicines.org.uk/emc/printdocument?documentId=8864 dated Jul. 28, 2015 relating to (9 pages).
Request for invalidation of CN patent 201480032321.8, dated Sep. 24, 2019, with English translation (57 pages).
Request for invalidation of CN patent 201480032321.8, dated Sep. 24, 2019—Evidence No. 1: CN1827107B, granted May 26, 2010, with English language counterpart International Patent Publication No. WO 9836728A2 (139 pages).
Request for invalidation of CN patent 201480032321.8, dated Sep. 24, 2019—Evidence No. 2: CN101528207B, granted Dec. 26, 2012 with English language counterpart U.S. Patent Application Publication No. 20100119A1 (14 pages).
Request for invalidation of CN patent 201480032321.8, dated Sep. 24, 2019—Evidence No. 3: International Patent Publication No. WO/98/36728A2 published Aug. 27, 1998 (95 pages).
Request for invalidation of CN patent 201480032321.8, dated Sep. 24, 2019—Evidence No. 4: CN1195505C granted Apr. 6, 2005, with English language counterpart U.S. Patent Application Publication No. 20040202710A1 (24 pages).
Request for invalidation of CN patent 201480032321.8, dated Sep. 24, 2019—Evidence No. 5: Mei Xuhui, et al., China Handbook of Licensed Pharmacists [M], published on Jan. 31, 2002, with partial English translation (4 pages).
Request for invalidation of CN patent 201480032321.8, dated Sep. 24, 2019—Evidence No. 6: Luo Mingsheng and Gao Tianhui, Pharmaceutical Excipients, published on Mar. 31, 1993, with partial English translation (9 pages).
Request for invalidation of CN patent 201480032321.8, dated Sep. 24, 2019—Evidence No. 7: Guo Tao, New Pharmacokinetics, published on Jan. 31, 2005, with partial English translation (7 pages).
Request for invalidation of CN patent 201480032321.8, dated Sep. 24, 2019—Evidence No. 8: Tian Jie and Yu Jinglong, Pharmacology [M], published on Jul. 31, 2012, with partial English translation (7 pages).
Request for invalidation of CN patent 201480032321.8, dated Sep. 24, 2019—Evidence No. 9: Reexamination decision No. FS12607, issued on Feb. 1, 2008, with partial English translation (10 pages).
Request for invalidation of CN patent 201480032321.8, dated Sep. 24, 2019—Evidence No. 10: US Patent Application Publication No. 20100119585A1, published on May 13, 2010 (6 pages).
Response to the Request for Invalidation of CN patent 201480032321.8, dated Dec. 5, 2019, with English translation (22 pages).
Response to the Request for Invalidation of CN patent 201480032321.8, dated Dec. 5, 2019—Counter Evidence No. 1: Chien, Yie W., Ed. 1987, *Transdermal Controlled Systemic Medication*, Marcel Dekker, Inc. New York and Basel, pp. 36-45, with partial Chinese translation (9 pages).
Response to the Request for Invalidation of CN patent 201480032321.8, dated Dec. 5, 2019—Counter Evidence No. 2: microscopic photo of the matrix layer of the Butrans® product, with Chinese translation (2 pages).
Response to the Request for Invalidation of CN patent 201480032321.8, dated Dec. 5, 2019—Counter Evidence No. 3: prescribing information for Butrans®, 2010, with partial Chinese translation (47 pages).
Response to the Request for Invalidation of CN patent 201480032321.8, dated Dec. 5, 2019—Marked-up version of replacement claim set, with English translation (34 pages).
Response to the Request for Invalidation of CN patent 201480032321.8. dated Dec. 5, 2019—Replacement claim set, with English translation (34 pages).
Opposition to EP 2790685, Decision of Opposition Division dated Dec. 20, 2019.
Decision to the Request for Invalidation of CN patent 201480032321.8, dated Mar. 9, 2020, with English Translation (65 pages).
Hearing Notice Section 15 (Office Action) dated Aug. 29, 2019, issued in Indian Patent Application No. 2662/CHENP/2009.

\* cited by examiner

BUPRENORPHINE TRANSDERMAL DELIVERY SYSTEM

This application is a continuation of U.S. patent application Ser. No. 15/414,138, filed Jan. 24, 2017, which is a continuation of U.S. patent application Ser. No. 14/772,474, filed Sep. 3, 2015, which is a U.S. national stage of International Patent Application No. PCT/EP2014/061567, filed Jun. 4, 2014, which claims benefit of U.S. Provisional Patent Application No. 61/830,975, filed Jun. 4, 2013, the disclosures of each of which are herein incorporated by reference in their entireties.

TECHNICAL FIELD OF THE INVENTION

The present invention relates to a transdermal therapeutic system (TTS) for the transdermal administration of buprenorphine, and processes of manufacture, uses thereof, and corresponding methods of treatment therewith.

BACKGROUND OF THE INVENTION

The active ingredient buprenorphine (5R,6R,7R,9R,13S,14S)-17-Cyclopropylmethyl-7-[(S)-3,3-dimethyl-2-hydroxybutan-2-yl]-6-methoxy-4,5-epoxy-6,14-ethanomorphinan-3-ol) is a partially synthetic opiate with high potency. Cancer patients may be treated with daily doses of around 1 mg. Despite its rather high molecular weight of 467.64 daltons, it is currently used for transdermal administration. The commercial TTS product Norspan®, also known as BuTrans®, delivers buprenorphine to the skin sufficiently to treat patients in pain for a time period of 7 days (about 168 hours) and allows therefore a use of the TTS over a time period of 7 days and allows in a fixed dosing regimen a once-weekly TTS exchange. This is specifically beneficial in terms of convenience and patient compliance. Thus the overall efficacy of the pain medicament is enhanced. However, the long administration periods may cause problems with skin irritation, which in combination with the considerable size (i.e., area of release) of the TTS may be problematic. Also, the large amount of excess drug in the TTS necessary to sustain enough driving force for sustaining the appropriate drug delivery over the long period of time is costly and has the potential to be subject to illicit use.

It is therefore desirable to reduce the overall size (i.e., area of release) of the TTS as well as the total amount of buprenorphine in the TTS before administration and also the amount remaining in the TTS after proper use, the residual amount. Thereby, the amount of drug available for illicit use (before and after proper use), and the amount to be wasted after proper use are both reduced. US Patent Application No. 2010/0119585 describes a certain TTS size and amount of drug reduction in comparison with the commercial TTS product Transtec® approved for an up-to-4 days administration regimen. Thus, the TTS needs to be replaced after 4 days at the latest. It is recommended to change Transtec® twice a week always on the same days at specific times, e.g. Monday mornings and Thursday evenings.

For convenience reasons it is, however, desirable to maintain the once weekly exchange mode (7 day dosing regimen) as, e.g., provided by the commercial product Norspan® instead of the every three to four days exchange mode as provided by, e.g., Transtec®.

The maintenance of sufficient release rates during a seven-day administration period is in particular challenging since the system is particularly sensitive to variability in the drug release. The tolerance for higher drug delivery at the beginning of the dosing period (also know as "drug burst") is very limited since the loss of drug at the beginning will lead to a loss of driving force later in the dosing period, in particular after three to four days of delivery.

A drug burst at the beginning and the variability of such systems thus need to be sufficiently controlled.

All references and publications cited herein are hereby incorporated by reference in their enteritis for all purposes.

OBJECTS AND SUMMARY OF THE INVENTION

A microreservoir system including deposits of buprenorphine and a carboxylic acid dispersed in a hydrophobic pressure sensitive adhesive layer provides high overall release rates during a seven-day administration period allowing a reduction of size and drug content in comparison to the commercial product Norspan®. The manufacturing of several batches, however, shows a high variability in the performance. These systems provide high performance but are biphasic due to the dispersed deposits (1. phase) in the adhesive (2. phase). Without wishing to be bound to any theory it is believed that the size and size distribution of the deposits influences the drug delivery. Large deposits release the drug too fast and provide for an undesired burst in the beginning of the dosing period and a failure of the system after three to four days. There is thus a need to sufficiently control the size and size distribution of the deposits.

It is an object of certain embodiments of the present invention to provide a transdermal therapeutic system for the transdermal administration of buprenorphine (e.g., buprenorphine base), which requires a relatively small amount of buprenorphine (e.g., buprenorphine base) contained therein and providing a sufficiently reproducible release of buprenorphine (e.g., buprenorphine base), in particular providing a reproducible release of buprenorphine (e.g., buprenorphine base) suitable for providing pain relief for about 168 hours (corresponding to 7 days or one week).

It is an object of certain embodiments of the present invention to provide a transdermal therapeutic system for the transdermal administration of buprenorphine (e.g., buprenorphine base) which requires a relatively small area of release and providing a sufficiently reproducible release of buprenorphine (e.g., buprenorphine base), in particular providing a reproducible release of buprenorphine (e.g., buprenorphine base) suitable for providing pain relief for about 168 hours (corresponding to 7 days or one week).

It is an object of certain embodiments of the present invention to provide reliable manufacturing processes for the above systems.

These objects and others are accomplished by the present invention, which according to one aspect relates to a transdermal therapeutic system for the transdermal administration of buprenorphine (e.g., buprenorphine base), comprising a buprenorphine (e.g., buprenorphine base) containing self-adhesive layer structure comprising A) a buprenorphine (e.g., buprenorphine base) impermeable backing layer, and B) a buprenorphine (e.g., buprenorphine base) containing pressure-sensitive adhesive layer on said buprenorphine-impermeable backing layer, the adhesive layer comprising
  a) at least one polymer-based pressure-sensitive adhesive,
  b) an analgesically effective amount of buprenorphine base or a pharmaceutically acceptable salt thereof, c) a viscosity-increasing substance in an amount of about 0.1% to about 8% of said buprenorphine-containing pressure-sensitive adhesive layer, and d) a carboxylic acid selected from the group consisting of oleic acid, linoleic acid, linolenic acid, levulinic acid and mixtures thereof, in an amount sufficient so that said analgesically effective amount of buprenorphine (e.g. buprenorphine base) is solubilized therein to form a mixture including said viscosity-increasing substance, and wherein the carboxylic acid-, buprenorphine- and viscosity-increasing substance-containing mixture forms dispersed deposits in said pressure-sensitive adhesive, and wherein preferably said buprenorphine-containing pressure-sensitive adhesive layer is the skin contact layer.

According to one specific aspect the invention relates to a transdermal therapeutic system for the transdermal administration of buprenorphine, comprising a buprenorphine-containing self-adhesive layer structure comprising A) a buprenorphine-impermeable backing layer, and B) a buprenorphine-containing pressure-sensitive adhesive layer on said buprenorphine-impermeable backing layer, the adhesive layer comprising a) at least one polymer-based pressure-sensitive adhesive, b) an analgesically effective amount of buprenorphine base or a pharmaceutically acceptable salt thereof, c) soluble polyvinylpyrrolidone, and d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said polyvinylpyrrolidone, and wherein the carboxylic acid-, buprenorphine- and polyvinylpyrrolidone-containing mixture forms dispersed deposits in the said pressure-sensitive adhesive, and wherein preferably said buprenorphine-containing pressure-sensitive adhesive layer is the skin contact layer.

According to one specific aspect the invention relates to a transdermal therapeutic system for the transdermal administration of buprenorphine base, comprising a buprenorphine base-containing self-adhesive layer structure comprising A) a buprenorphine base-impermeable backing layer, and B) a buprenorphine base-containing pressure-sensitive adhesive layer on said buprenorphine base-impermeable backing layer, the adhesive layer comprising a) at least one pressure-sensitive adhesive based on polysiloxane, b) an analgesically effective amount of buprenorphine base, c) soluble polyvinylpyrrolidone in an amount of about 1% to about 4% of the buprenorphine base-containing pressure-sensitive adhesive layer, wherein the polyvinylpyrrolidone has a K-Value of at least about 80, and d) levulinic acid, in an amount sufficient so that said analgesically effective amount of buprenorphine base is solubilized therein to form a mixture including said polyvinylpyrrolidone, and wherein the levulinic acid-, buprenorphine base- and polyvinylpyrrolidone-containing mixture forms dispersed deposits in the said pressure-sensitive adhesive, and wherein preferably said buprenorphine base-containing pressure-sensitive adhesive layer is the skin contact layer.

According to further aspects the invention relates to a method of treating pain in a patient by applying a transdermal therapeutic system in accordance with the invention to the skin of a patient, in particular to a method of treating pain in a patient by applying a transdermal therapeutic system in accordance with the invention to the skin of said patient for more than about 96 hours (or for more than 4 days), or for about 120 hours (or for 5 days), or for about 144 hours (or for 6 days) or for about 168 hours (or for 7 days or for one week).

According to one specific aspect, the invention relates to a method of treating pain in a patient by applying to the skin of said patient for about 168 hours (or for 7 days or for one week) a transdermal therapeutic system, comprising a buprenorphine (e.g., buprenorphine base) containing self-adhesive layer structure comprising A) a buprenorphine (e.g., buprenorphine base) impermeable backing layer, and B) a buprenorphine (e.g., buprenorphine base) containing pressure-sensitive adhesive layer on said buprenorphine-impermeable backing layer, the adhesive layer comprising a) at least one polymer-based pressure-sensitive adhesive, b) an analgesically effective amount of buprenorphine base or a pharmaceutically acceptable salt thereof, c) a viscosity-increasing substance in an amount of about 0.1% to about 8% of said buprenorphine-containing pressure-sensitive adhesive layer, and d) a carboxylic acid selected from the group consisting of oleic acid, linoleic acid, linolenic acid, levulinic acid and mixtures thereof, in an amount sufficient so that said analgesically effective amount of buprenorphine (e.g. buprenorphine base) is solubilized therein to form a mixture including said viscosity-increasing substance, and wherein the carboxylic acid-, buprenorphine- and viscosity-increasing substance-containing mixture forms dispersed deposits in said pressure-sensitive adhesive, and wherein preferably said buprenorphine-containing pressure-sensitive adhesive layer is the skin contact layer.

According to one specific aspect, the invention relates to a method of treating pain in a patient by applying for about 168 hours on the skin of a patient a transdermal therapeutic system for the transdermal administration of buprenorphine, comprising a buprenorphine-containing self-adhesive layer structure comprising A) a buprenorphine-impermeable backing layer, and B) a buprenorphine-containing pressure-sensitive adhesive layer on said buprenorphine-impermeable backing layer, the adhesive layer comprising a) at least one polymer-based pressure-sensitive adhesive, b) an analgesically effective amount of buprenorphine base or a pharmaceutically acceptable salt thereof, c) soluble polyvinylpyrrolidone, and d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said polyvinylpyrrolidone, and wherein the carboxylic acid-, buprenorphine- and polyvinylpyrrolidone-containing mixture forms dispersed deposits in the said pressure-sensitive adhesive, and wherein preferably said buprenorphine-containing pressure-sensitive adhesive layer is the skin contact layer.

According to one aspect, the invention relates to a method of treating pain in a patient by applying to the skin of said patient for about 168 hours a transdermal therapeutic system, comprising a buprenorphine base-containing self-adhesive layer structure comprising
- A) a buprenorphine base-impermeable backing layer, and
- B) a buprenorphine base-containing pressure-sensitive adhesive layer on said buprenorphine base-impermeable backing layer, the adhesive layer comprising
  - a) at least one pressure-sensitive adhesive based on polysiloxane,
  - b) an analgesically effective amount of buprenorphine base,
  - c) soluble polyvinylpyrrolidone in an amount of about 1% to about 4% of the buprenorphine base-containing pressure-sensitive adhesive layer, wherein the polyvinylpyrrolidone has a K-Value of at least about 80, and
  - d) levulinic acid, in an amount sufficient so that said analgesically effective amount of buprenorphine base is solubilized therein to form a mixture including said polyvinylpyrrolidone, and wherein the levulinic acid-, buprenorphine base- and polyvinylpyrrolidone-containing mixture forms dispersed deposits in the said pressure-sensitive adhesive, and wherein said buprenorphine base-containing pressure-sensitive adhesive layer is the skin contact layer.

According to one aspect, the invention relates to a set of two to five different transdermal therapeutic systems for the transdermal administration of buprenorphine base selected from five different transdermal therapeutic systems, i.e., a first, a second, a third, a forth and a fifth transdermal therapeutic system, each of the five different transdermal therapeutic systems comprising a buprenorphine-containing self-adhesive layer structure comprising
- A) a buprenorphine base-impermeable backing layer, and
- B) a buprenorphine base-containing pressure-sensitive adhesive layer on said buprenorphine base-impermeable backing layer, the adhesive layer comprising
  - a) at least one pressure-sensitive adhesive based on polysiloxanes,
  - b) an analgesically effective amount of buprenorphine base,
  - c) soluble polyvinylpyrrolidone in an amount of about 1% to about 4% of the buprenorphine base-containing pressure-sensitive adhesive layer, wherein the polyvinylpyrrolidone has a K-Value of at least about 80, and
  - d) levulinic acid, in an amount sufficient so that said analgesically effective amount of buprenorphine base is solubilized therein to form a mixture including said polyvinylpyrrolidone, and wherein the levulinic acid-, buprenorphine base- and polyvinylpyrrolidone-containing mixture forms dispersed deposits in the said pressure-sensitive adhesive, and wherein,
the first transdermal therapeutic system provides a size of said buprenorphine-containing pressure-sensitive adhesive layer providing the area of release ranging from about 1 $cm^2$ to about 4.8 $cm^2$ and contains from about 1 mg to about 4 mg buprenorphine base;
the second transdermal therapeutic system provides a size of said buprenorphine-containing pressure-sensitive adhesive layer providing the area of release ranging from about 3 $cm^2$ to about 9.5 $cm^2$ and contains from about 3.5 mg to about 8 mg buprenorphine base; and
the third transdermal therapeutic system provides a size of said buprenorphine-containing pressure-sensitive adhesive layer providing the area of release ranging from about 6 $cm^2$ to about 19 $cm^2$ and contains from about 6.5 mg to about 16 mg buprenorphine base; and
the fourth transdermal therapeutic system provides a size of said buprenorphine-containing pressure-sensitive adhesive layer providing the area of release ranging from about 12 $cm^2$ to about 28.5 $cm^2$ and contains from about 11.5 mg to about 24 mg buprenorphine base; and
the fifth transdermal therapeutic system provides a size of said buprenorphine-containing pressure-sensitive adhesive layer providing the area of release ranging from about 16 $cm^2$ to about 38 $cm^2$ and contains from about 15 mg to about 32 mg buprenorphine base,
wherein the five different transdermal therapeutic systems have increasing areas of release and amounts of buprenorphine from the first to the fifth transdermal therapeutic system for use in method of treating pain by applying one of said transdermal therapeutic systems for about 168 hours on the skin of a patient. The set of two to five different transdermal therapeutic systems in accordance with this paragraph can be expanded by one or more further transdermal therapeutic system(s) which may provide smaller, greater or intermediate areas of release and amounts of buprenorphine compared with the five different transdermal therapeutic systems described above, preferably the set of two to five different transdermal therapeutic systems is expanded by a further transdermal therapeutic system which provides a size of said buprenorphine-containing pressure-sensitive adhesive layer providing the area of release ranging from about 5 $cm^2$ to about 14 $cm^2$ and contains an amount of said buprenorphine from about 5.5 mg to about 13 mg buprenorphine base or an equimolar amount of a pharmaceutically acceptable salt thereof, providing an intermediate transdermal therapeutic system between the second and the third transdermal therapeutic system. Alternatively, one of the transdermal therapeutic systems of the set of two to five different transdermal therapeutic systems described above can be replaced by such a further transdermal therapeutic system.

According to one aspect, the invention relates to a set of transdermal therapeutic systems including at least two transdermal therapeutic systems selected from the first, second, third, fourth and fifth transdermal therapeutic systems as described in the previous paragraphs. According to one specific aspect, the at least two transdermal therapeutic systems can be selected from the first, second, third, fourth and fifth transdermal therapeutic system as described in the previous paragraphs, and the further transdermal therapeutic system which provides a size of said buprenorphine-containing pressure-sensitive adhesive layer providing the area of release ranging from about 5 $cm^2$ to about 14 $cm^2$ and contains an amount of said buprenorphine from about 5.5 mg to about 13 mg buprenorphine base.

According to one aspect, the invention relates to a method of treating pain in a patient by selecting for said patient the appropriate transdermal therapeutic system from the first, second, third, fourth and fifth transdermal therapeutic system as described in the previous two paragraphs, and subsequently applying said selected transdermal therapeutic system on the skin of said patient for about 168 hours. According to one specific aspect, the invention relates to a method of treating pain in a patient by selecting for said patient the appropriate transdermal therapeutic system from the first, second, third, fourth and fifth, and the further transdermal therapeutic system as described in the previous two paragraphs, and subsequently applying said selected transdermal therapeutic system on the skin of said patient for about 168 hours.

According to one aspect, the invention relates to a transdermal therapeutic system for the transdermal administration of buprenorphine, wherein buprenorphine is present in the form of buprenorphine base and providing a non-cumulative release of buprenorphine base as measured in a Franz diffusion cell with dermatomed human skin of 2 $\mu g/cm^2$ to 10 $\mu g/cm^2$ in the first 8 hours,
20 $\mu g/cm^2$ to 80 $\mu g/cm^2$ from hour 8 to hour 24,
20 $\mu g/cm^2$ to 80 $\mu g/cm^2$ from hour 24 to hour 32,
30 $\mu g/cm^2$ to 120 $\mu g/cm^2$ from hour 32 to hour 48,
40 $\mu g/cm^2$ to 150 $\mu g/cm^2$ from hour 48 to hour 72,
100 $\mu g/cm^2$ to 300 $\mu g/cm^2$ from hour 72 to hour 144, and
30 $\mu g/cm^2$ to 100 $\mu g/cm^2$ from hour 144 to hour 168, and
comprising a buprenorphine base-containing self-adhesive layer structure comprising
  A) a buprenorphine base-impermeable backing layer, and
  B) a buprenorphine base-containing pressure-sensitive adhesive layer on said buprenorphine base-impermeable backing layer, the adhesive layer comprising
    a) at least one polymer-based pressure-sensitive adhesive,
    b) an analgesically effective amount of buprenorphine base,
    c) a viscosity-increasing substance in an amount of about 0.1% to about 8% of said buprenorphine-containing pressure-sensitive adhesive layer, and
    d) a carboxylic acid selected from the group consisting of oleic acid, linoleic acid, linolenic acid, levulinic acid and mixtures thereof, in an amount sufficient so that said analgesically effective amount of buprenorphine base is solubilized therein to form a mixture including said viscosity-increasing substance, and wherein the carboxylic acid-, buprenorphine base- and viscosity-increasing substance-containing mixture forms dispersed deposits in the said pressure-sensitive adhesive, and
wherein preferably said buprenorphine base-containing pressure-sensitive adhesive layer is the skin contact layer, in particular for use in a method of treating pain by applying the transdermal therapeutic system for about 168 hours on the skin of a patient.

The release characteristic can also be described in terms of a mean non-cumulative skin permeation rate of
0.25 $\mu g/cm^2$-hr to 1.25 $\mu g/cm^2$-hr in the first 8 hours,
1.25 $\mu g/cm^2$-hr to 5.0 $\mu g/cm^2$-hr from hour 8 to hour 24,
2.5 $\mu g/cm^2$-hr to 10 $\mu g/cm$-hr$^2$ from hour 24 to hour 32,
1.25 $\mu g/cm^2$-hr to 5.0 $\mu g/cm^2$-hr from hour 32 to hour 48,
1.6 $\mu g/cm^2$-hr to 6.25 $\mu g/cm^2$-hr from hour 48 to hour 72,
1.3 $\mu g/cm^2$-hr to 4.2 $\mu g/cm^2$-hr from hour 72 to hour 144, and
1.25 $\mu g/cm^2$-hr to 4.2 $\mu g/cm^2$-hr from hour 144 to hour 168.

According to one aspect, the invention relates to a transdermal therapeutic system comprising buprenorphine for the transdermal administration of buprenorphine, wherein buprenorphine is present in the form of buprenorphine base and providing a non-cumulative release of buprenorphine base as measured in a Franz diffusion cell with dermatomed human skin of 2 $\mu g/cm^2$ to 10 $\mu g/cm^2$ in the first 8 hours,
20 $\mu g/cm^2$ to 80 $\mu g/cm^2$ from hour 8 to hour 24,
20 $\mu g/cm^2$ to 80 $\mu g/cm^2$ from hour 24 to hour 32,
30 $\mu g/cm^2$ to 120 $\mu g/cm^2$ from hour 32 to hour 48,
40 $\mu g/cm^2$ to 150 $\mu g/cm^2$ from hour 48 to hour 72,
100 $\mu g/cm^2$ to 300 $\mu g/cm^2$ from hour 72 to hour 144, and
30 $\mu g/cm^2$ to 100 $\mu g/cm^2$ from hour 144 to hour 168, and
comprising a buprenorphine base-containing self-adhesive layer structure comprising
  A) a buprenorphine base-impermeable backing layer, and
  B) a buprenorphine base-containing pressure-sensitive adhesive layer on said buprenorphine base-impermeable backing layer, the adhesive layer comprising
    a) at least one polymer-based pressure-sensitive adhesive,
    b) an analgesically effective amount of buprenorphine base,
    c) soluble polyvinylpyrrolidone, and
    d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said polyvinylpyrrolidone, and wherein the carboxylic acid-, buprenorphine- and polyvinylpyrrolidone-containing mixture forms dispersed deposits in the said pressure-sensitive adhesive, and
wherein said buprenorphine base-containing pressure-sensitive adhesive layer is the skin contact layer.

The release characteristic can also be described in terms of a mean non-cumulative skin permeation rate of
0.25 $\mu g/cm^2$-hr to 1.25 $\mu g/cm^2$-hr in the first 8 hours,
1.25 $\mu g/cm^2$-hr to 5.0 $\mu g/cm^2$-hr from hour 8 to hour 24,
2.5 $\mu g/cm^2$-hr to 10 $\mu g/cm$-hr$^2$ from hour 24 to hour 32,
1.25 $\mu g/cm^2$-hr to 5.0 $\mu g/cm^2$-hr from hour 32 to hour 48,
1.6 $\mu g/cm^2$-hr to 6.25 $\mu g/cm^2$-hr from hour 48 to hour 72,
1.3 $\mu g/cm^2$-hr to 4.2 $\mu g/cm^2$-hr from hour 72 to hour 144, and
1.25 $\mu g/cm^2$-hr to 4.2 $\mu g/cm^2$-hr from hour 144 to hour 168.

According to one specific aspect the invention relates to a method of manufacture of a transdermal therapeutic system for the transdermal administration of buprenorphine in accordance with the invention, comprising the steps of
1. providing a buprenorphine-containing adhesive mixture comprising
   a) buprenorphine base or a pharmaceutically acceptable salt thereof
   b) a carboxylic acid,
   c) a viscosity-increasing substance,
   d) a polymer-based pressure-sensitive adhesive, and
   e) solvent
2. storing said mixture between 0 hours and 6 days
3. homogenizing said buprenorphine-containing adhesive mixture at a homogenizing at e.g. a speed of at least 1000 rpm;
4. storing said homogenized mixture between 0 hours and 6 days
5. coating said buprenorphine-containing adhesive mixture on a film using a roller coater in an amount to provide the desired coating dry weight,
6. drying said coated buprenorphine-containing adhesive mixture to provide a buprenorphine-containing adhesive layer with the desired coating dry weight,
7. optionally laminating said buprenorphine-containing adhesive layer to a backing layer to provide an buprenorphine-containing self-adhesive layer structure, 8. optionally punching the individual systems from the buprenorphine-containing self-adhesive layer structure with the desired area of release, and
9. optionally adhering to the individual systems an active agent-free self-adhesive layer structure comprising also a backing layer and an active agent-free pressure-sensitive adhesive layer and which is larger than the individual systems of buprenorphine-containing self-adhesive layer structure, preferably wherein in step 1 buprenorphine is present in the form of buprenorphine base, the carboxylic acid is levulinic acid and the viscosity-increasing substance is polyvinylpyrrolidone and all are dissolved in an appropriate solvent (e.g. ethanol), and subsequently suspended in a pressure-sensitive adhesive based on polysiloxane in an appropriate solvent (e.g. heptanes) to provide the buprenorphine-containing adhesive mixture or solution.

Useful solvents for dissolving buprenorphine, carboxylic acid and the viscosity-increasing substance are alcohols (e.g. ethanol), acetone and methyl ethyl ketone, ethanol is preferred. The polymer-based pressure-sensitive adhesive may be dissolved in heptanes, hexanes, toluene, or ethylacetate, preferably in heptane. The solvent for buprenorphine has preferably only limited or no capability of dissolving the polymer-based pressure-sensitive adhesive and the solvent for the polymer-based pressure-sensitive adhesive has preferrably only limited or no capability of dissolving buprenorphine.

According to one aspect, the invention relates to the use of polyvinylpyrrolidone in the manufacture of a transdermal therapeutic system for the transdermal administration of buprenorphine which system includes deposits of a mixture including buprenorphine base and a carboxylic acid dispersed in a pressure-sensitive adhesive based on polysiloxane to control the size of the deposits during the manufacture.

Within the meaning of this invention, the term "transdermal therapeutic system" (or TTS) refers to the entire individual unit that is applied to the skin of a patient, and which comprises the buprenorphine-containing self-adhesive layer structure and optionally an additional larger active-free self-adhesive layer structure on top of the buprenorphine-containing self-adhesive layer structure, which TTS provides the percutaneous delivery of the active buprenorphine to the patient. During storage, such a TTS is normally located on a redetachable protective layer from which it is removed immediately before application to the surface of the patient's skin. A TTS protected this way may be stored in a blister pack or a side sealed bag.

Within the meaning of this invention, the term "buprenorphine-containing self-adhesive layer structure" refers to the active agent-containing structure providing the area of release of the active agent.

Within the meaning of this invention, "polymer-based pressure-sensitive adhesive" refers to a pressure-sensitive adhesive containing from 75% to 100% of said polymer based on the dry weight of the pressure-sensitive adhesive, e.g., 75% to 100% of polysiloxane. According to certain embodiments the pressure-sensitive adhesive contains from 80% to 100%, or from 85% to 100%, or from 90% to 100%, or from 95% to 100% of the polymer (e.g., polysiloxane) based on the dry weight of the pressure sensitive adhesive. A pressure-sensitive adhesive is in particular a material that adheres with finger pressure, is permanently tacky, exerts a strong holding force and should be removable from smooth surface without leaving a residue. Examples of useful pressure-sensitive adhesives based on polysiloxane which are commercially available include the standard Bio-PSA series (7-4400, 7-4500 and 7-4600 series), the amine compatible (endcapped) Bio-PSA series (7-4100, 7-4200 and 7-4300 series) and the Soft Skin Adhesives series (7-9800) manufactured by Dow Corning. Preferred pressure-sensitive adhesives based on polysiloxane are heptane-solvated pressure-sensitive adhesives including BIO-PSA 7-4201, BIO-PSA 7-4301 and BIO-PSA 7-4501.

Within the meaning of this invention, the term "additional larger active agent-free self-adhesive layer structure" refers to a self-adhesive layer structure that is free of active agent and larger in area than the active agent-containing structure and providing additional area adhering to the skin, but no area of release of the active agent, and enhancing thereby the overall adhesive properties of the TTS.

Within the meaning of this invention, the term "buprenorphine-containing pressure-sensitive adhesive layer" and "matrix layer" have the same meaning and refer to the layer containing the active agent (the buprenorphine) in a matrix-type structure of active in-adhesive. % amount of ingredients refers to the solid contents.

Within the meaning of this invention, the term "skin contact layer" refers to the part of the TTS which is in direct contact with the skin of the patient during administration and is located in/co-extensive with the buprenorphine-containing self-adhesive layer structure. The sizes of the "skin contact layer" and the buprenorphine-containing self-adhesive layer structure are co-extensive and correspond to the area of release.

Within the meaning of this invention, the term "deposit" as used in reference to "dispersed deposits" refers to distinguishable, e.g., visually distinguishable, areas within the pressure-sensitive adhesive. Such deposits are e.g., droplets. Deposits that are visually distinguishable may be identified by use of a microscope.

Within the meaning of this invention, the term "viscosity-increasing substance" refers to a substance which when added to the mixture of buprenorphine and carboxylic acid increases the viscosity of the mixture.

Within the meaning of this invention, the K-value refers to a value calculated from the relative viscosity of polyvinylpyrrolidone in water according to the Ph. Eur. and USP monographs for "Povidone".

Within the meaning of this invention the term "soluble polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Such soluble polyvinylpyrrolidone is supplied by BASF as Kollidon 12 PF, Kollidon 17 PF, Kollidon 25, Kollidon 30 and Kollidon 90 F. Kollidon 90 F is used throughout the examples.

Within the meaning of this invention, the size of the deposits refers to the diameter of the deposits as measured using a microscopic picture of the layers structure.

Within the meaning of this invention, the term "roll coater" refers to a coater which provides a coating whereby the fluid flow in a nip between a pair of rotating rolls controls both the thickness and the uniformity of the coated film.

Within the meaning of this invention the "in-vitro dissolution" is determined using a rotating cylinder apparatus of the Ph Eur/USP using 600 ml degassed 0.9% sodium chloride solution at 32° C. and rotated at 50 rpm. At 0.5, 2, 8 (or 5) and 24 hours, 4 ml samples are removed and analyzed by a reverse phase HPLC method using a mobile phase of 55:45% v/v acetonitrile:0.05 M potassium dihydrogen phosphate (adjusted to pH 3.5) and UV detection at 220 nm.

Within the meaning of this invention, the parameter "mean cumulative skin permeation rate" is provided in $\mu g/cm^2$-hr and is calculated from the cumulative release as measured by in vitro experiments carried out with the Franz diffusion cell over the total time period of release, e.g., 168 hours, in $\mu g/cm^2$ divided by the hours corresponding to said total time period of release, e.g., 168 hours, taking into account a lag time of 24 hours.

Within the meaning of this invention, the parameter "mean non-cumulative skin permeation rate" is provided in $\mu g/cm^2$-hr and is calculated from the non-cumulative release of a certain sample interval as measured in a Franz diffusion cell in $\mu g/cm^2$ divided by the hours of said sample interval.

Within the meaning of this invention, the parameter "cumulative release" is provided in $\mu g/cm^2$ and relates to the total amount released over the total time period of release, e.g., 168 hours, as measured in a Franz diffusion cell. The value is a mean value of at least 3 experiments.

Within the meaning of this invention, the parameter "non-cumulative release" is provided in $\mu g/cm^2$ and relates to the amount released in a sample interval at certain elapsed time within the total time period of release, e.g., hour 16 of release corresponding to a sample interval of 8 hours from hour 8 to hour 16 of release within 168 hours of total time period of release, as measured in a Franz diffusion cell. The value is a mean value of at least 3 experiments.

Within the meaning of this invention, the parameter "mean release rate" refers to the mean release rate in $\mu g/hr$ over the period of administration (e.g., 7 days) by which the active agent permeates through the human skin into the blood system and is based on the AUC obtained over said period of administration in a clinical study.

Within the meaning of this invention, the parameter "nominal mean release rate" refers to an assigned mean release rate determined by comparison with the commercial reference product BuTrans® which is applied for 7 days to the skin of the subjects and of which mean release rates are publicly available from the package insert. The corresponding known nominal mean release rate of the 25 cm² area of release BuTrans® reference TTS containing 20 mg buprenorphine is 20 µg/hr. The mean release rate is proportional to the size of the area of release of a TTS and may be used to distinguish TTS's by the dosage strength. The BuTrans® TTS with half the size (i.e. 12.5 cm² area of release) and containing 10 mg of buprenorphine provides the known nominal mean release rate of 10 µg/hr. The BuTrans® TTS with a size of 6.25 cm² area of release and containing 5 mg of buprenorphine provides the known nominal mean release rate of 5 µg/hr. Accordingly, it can be assumed that a corresponding TTS with a size of 50 cm² area of release and containing 40 mg of buprenorphine provides a nominal mean release rate of 40 µg/hr, and a corresponding TTS with a size of 37.5 cm² area of release and containing 30 mg of buprenorphine provides a nominal mean release rate of 30 µg/hr, and a corresponding TTS with a size of 18.75 cm² area of release and containing 15 mg of buprenorphine provides a nominal mean release rate of 15 µg/hr. The nominal mean release rates are assigned to the TTSs in accordance with the invention by comparing the Franz diffusion cell skin permeation rates of the reference TTS BuTrans® with the Franz diffusion cell skin permeation rates of the TTS's in accordance with the invention.

Within the meaning of this invention, the meaning of "by applying to the skin of said patient for about 168 hours" corresponds to "by applying to the skin of said patient for about 7 days or for one week" and refers to a once a week exchange mode or dosing regimen. Likewise, about 96 hours correspond to 4 days, about 120 hours correspond to 5 days and about 144 hours correspond to 6 days. The term "applying to the skin of a patient for a certain period of time" has the same meaning as "administration for a certain period of time".

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

If not indicated otherwise "%" refers to weight-%.

Within the meaning of this invention, the term "active", "active agent", and the like, as well as the term "buprenorphine" refers to buprenorphine base or a pharmaceutically acceptable salt thereof. Unless otherwise indicated the amounts of buprenorphine in the TTS relate to the amount of buprenorphine before administration of the TTS. The amounts of buprenorphine in the TTS after administration are referred to as residual amounts.

Within the meaning of this invention, values and ranges specifying the size of the area of release and the amount of buprenorphine contained in the transdermal therapeutic system are mean values of at least 3 measurements.

Within the meaning of this invention the term "pharmacokinetic parameters" refers to parameters describing the blood plasma curve, e.g. Cmax, AUCt and AUCINF obtained in a clinical study, e.g. by single-dose administration of the active agent TTS, e.g. the buprenorphine base TTS to healthy human subjects. The pharmacokinetic performance of the TTSs in accordance with the invention can be deduced from the performance of the buprenorphine-containing microreservoir systems disclosed in the international application PCT/IB2012/002973 (see e.g. pages 69 to 100 of PCT/IB2012/002973). The pharmacokinetic parameters of the individual subjects are summarized in PCT/IB2012/002973 using arithmetic and geometric means, e.g. a mean Cmax, a mean AUCt and a mean AUCINF, and additional statistics such as the respective standard deviations and standard errors, the minimum value, the maximum value, and the middle value when the list of values is ranked (Median). In the context of the present invention, pharmacokinetic parameters, e.g. the mean Cmax, the mean AUCt and the mean AUCINF refer to geometric mean values if not indicated otherwise. It cannot be precluded that the absolute mean values obtained for a certain TTS in a clinical study vary to a certain extend from study to study. To allow a comparison of absolute mean values between studies, a reference formulation, e.g. the commercial reference product BuTrans® or in the future any product based on the invention, may be used as internal standard. A comparison of the AUC per area of release, e.g. the mean AUCt per area of release of the respective reference product in the earlier and later study can be used to obtain a correction factor to take into account differences from study to study. In the clinical study described in PCT/IB2012/002973 the commercial reference product BuTrans® provides an AUCt per area of release of 1624.53 pg·hr/ml-cm². It was shown in the same study that microreservoir systems including deposits of buprenorphine and a carboxylic acid dispersed in a hydrophobic pressure sensitive adhesive layer provide a better performance in terms of the AUCt per area of release compared with the commercial product BuTrans®, i.e., Examples 1 and 2 of PCT/IB2012/002973 provide an AUCt per area of release of 2690.49 pg·hr/ml-cm² and 2746.86 pg·hr/ml-cm², respectively. The microreservoir systems thus provide an about 1.7-fold better performance than the commercial product BuTrans® in the same study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least ten individual healthy human subjects.

Within the meaning of this invention, the term "geometric mean" refers to the mean of the log transformed data backtransformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "AUCt" is provided in pg·hr/ml and relates to the area under the plasma concentration-time curve from hour 0 to the last measurable plasma concentration and is calculated by the linear trapezoidal method.

Within the meaning of this invention, the parameter "mean AUCt per area of release" is provided in pg·hr/ml-cm² and is calculated from the geometric mean AUCt as determined for a certain TTS in pg·hr/ml divided by the area of release of said TTS.

Within the meaning of this invention, the parameter "AUCINF" is provided in pg·hr/ml and relates to the area under the plasma concentration-time curve extrapolated to infinity and is calculated using the formula:

$$AUCINF = AUCt + \frac{CLast}{LambdaZ}$$

where CLast is the last measurable plasma concentration and LambdaZ is the apparent terminal phase rate constant.

Within the meaning of this invention, the parameter "Cmax" is provided in pg/ml and and relates to the maximum observed blood plasma concentration of the active agent.

Within the meaning of this invention, the parameter "t max" is provided in hr and relates to the time point at which the Cmax value is reached. In other words, t max is the time point of the maximum observed plasma concentration.

Within the meaning of this invention, the parameter "LambdaZ" is provided in 1/hr and relates to the apparent terminal phase rate constant, where LambdaZ is the magnitude of the slope of the linear regression of the log concentration versus time profile during the terminal phase.

Within the meaning of this invention, the parameter "t½Z" is provided in hr and relates to the apparent plasma terminal phase half-life and is commonly determined as t½Z=(ln 2)/LambdaZ.

Within the meaning of this invention, the term "mean plasma concentration" is provided in pg/ml and is a mean of the individual plasma concentrations of active agent, e.g. buprenorphine base, at each point in time.

Within the meaning of this invention, the term "bioequivalent" is defined to refer to a TTS that provides geometric mean values of Cmax, AUCt, and AUCINF for buprenorphine, wherein the 90% confidence intervals estimated for the ratio test/reference fall within the range of 80.00% to 125.00%.

DETAILED DESCRIPTION

Figure 1:
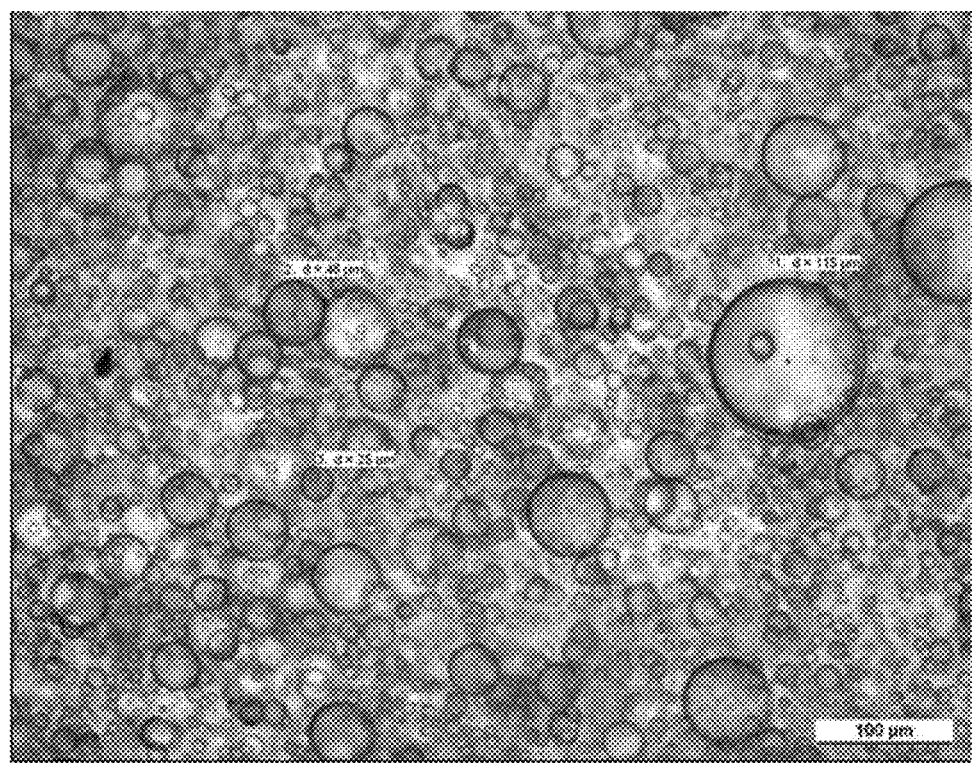
FIG. 1 depicts a microscopic picture of the matrix layer of Comparative Example 1.

A microreservoir system including deposits of buprenorphine and a carboxylic acid dispersed in a hydrophobic pressure-sensitive adhesive layer provides high overall release rates during a seven-day administration period, thereby allowing a reduction of size and drug content of the TTS in comparison to the commercial product Norspan®. Such systems are described in the parallel patent application PCT/US2012/069242, corresponding to PCT/IB2012/002973, which is hereby incorporated by reference. In particular reference is made to Examples 1 to 4 in PCT/US2012/069242, corresponding to PCT/IB2012/002973. The manufacturing of several batches, however, shows a high variability in the performance. These systems provide high performance but are biphasic due to the dispersed deposits (1. phase) in the adhesive (2. phase). Without wishing to be bound to any theory, it is believed that the size and size distribution of the deposits influences the drug delivery. Large deposits release the drug too fast and provide for an undesired burst in the beginning of the dosing period and a failure of the system after three to four days. There is thus a need to sufficiently control the size and size distribution of the deposits.

The production of a commercial transdermal product as disclosed herein requires a continuous coating and drying process to form the buprenorphine-containing pressure sensitive adhesive layer. Such coating is usually accomplished with a sufficiently sized roller coater and attached drying compartment. The buprenorphine-containing mixture to be coated is usually prepared batch wise, and is then stored for some time until the coater is ready to coat the mixture. The time between the preparation of the mixture and the coating of the mixture in a normal production routine can be almost zero, if after mixing/homogenizing the mass will be transferred to the coating station and is coated directly and may be as long as several days, e.g. four to six days, to store the mixture during the time of a failure of the coater or a weekend or other reasons for a coating process interruption. Thus the mixture must be sufficiently stable. A microreservoir system as described herein including two phases, namely the deposits and the adhesive surrounding the deposits which may change over time due to the fusion of individual deposits forming larger deposits. Thus the deposits must be hindered in fusing during the storing time between mixing and coating.

Additionally, the shearing force applied to the coating mixture during coating in a roller coater is different and higher than on a laboratory scale coating technique like such as when using the Erichsen coater. But for commercial scale production, a roller coater is necessary to provide the necessary scale up and the necessary coating precision. However, the shear force in a roller coater causes additional fusion of the deposits. Thus the deposits must be hindered in fusing during the coating process using a roller coater.

TTS Structure

According to a certain embodiment of the invention the transdermal therapeutic system for the transdermal administration of buprenorphine comprises a buprenorphine-containing self-adhesive layer structure comprising
A) a buprenorphine-impermeable backing layer, and
B) a buprenorphine-containing pressure-sensitive adhesive layer on said buprenorphine-impermeable backing layer, the adhesive layer comprising
 a) at least one polymer-based pressure-sensitive adhesive,
 b) an analgesically effective amount of buprenorphine base or a pharmaceutically acceptable salt thereof,
 c) a viscosity-increasing substance in an amount of about 0.1% to about 8% of said buprenorphine-containing pressure-sensitive adhesive layer, and
 d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said viscosity-increasing substance, and wherein the carboxylic acid-, buprenorphine- and viscosity-increasing substance-containing mixture forms dispersed deposits in the said pressure-sensitive adhesive, and
wherein said buprenorphine-containing pressure-sensitive adhesive layer is preferably the skin contact layer.

Without wishing to be bound to any theory it is believed that the viscosity-increasing substance increases the viscosity of the deposits (inner phase) within the adhesive solution (outer phase) during the production and within the adhesive matrix (outer phase) during the storage of the dried buprenorphine-containing layer.

Useful viscosity-increasing substances may be selected from the group consisting of cellulose derivatives such as methylcellulose, ethylcellulose, hydroxyethylcellulose, hydroxypropylcellulose, hydroxypropylmethylcellulose, carboxymethylcellulose, sodium carboxymethylcellulose, and microcrystalline cellulose, high molecular mass polyacrylic acids and/or their salts and/or their derivatives such as esters, polyvinylpyrrolidone, in particular soluble polyvinylpyrrolidone, colloidal silicone dioxide, sodium alginate, tragacanth, xanthan gum, bentonite, carageenan and guar gum. A preferred viscosity-increasing substance is polyvinylpyrrolidone.

In certain embodiments of the invention the viscosity-increasing substance is present in an amount of about 0.1% to about 7%, or in an amount of about 0.5% to about 5%, preferably in an amount of about 1% to about 4%, more preferably in an amount of about 2% to about 3% of the buprenorphine-containing pressure-sensitive adhesive layer.

According to a certain independent embodiments of the invention wherein the structure is concerned, the transdermal therapeutic system for the transdermal administration of buprenorphine comprises a buprenorphine-containing self-adhesive layer structure comprising
A) a buprenorphine-impermeable backing layer, and
B) a buprenorphine-containing pressure-sensitive adhesive layer on said buprenorphine-impermeable backing layer, the adhesive layer comprising
 a) at least one polymer-based pressure-sensitive adhesive,
 b) an analgesically effective amount of buprenorphine base or a pharmaceutically acceptable salt thereof,
 c) soluble polyvinylpyrrolidone, and
 d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said polyvinylpyrrolidone, and wherein the carboxylic acid-, buprenorphine- and polyvinylpyrrolidone-containing mixture forms dispersed deposits in the said pressure-sensitive adhesive, and
wherein said buprenorphine-containing pressure-sensitive adhesive layer is the skin contact layer.

Without wishing to be bound to any theory it is believed that the polyvinylpyrrolidone having a K-Value of at least 5, at least 10, at least 15, at least 20, at least 50, or a K-Value of at least 80 is in particular beneficial in increasing the viscosity of the deposits (inner phase) within the adhesive solution (outer phase) during the production and within the adhesive matrix (outer phase) during the storage of the dried buprenorphine-containing layer. The increase in viscosity si beneficial because the deposits are thereby hindered in fusing during the storing time between mixing and coating.

In certain embodiments of the invention the transdermal therapeutic system for the transdermal administration of buprenorphine comprises a buprenorphine-containing self-adhesive layer structure comprising A) a buprenorphine base-impermeable backing layer, and
B) a buprenorphine base-containing pressure-sensitive adhesive layer on said buprenorphine base-impermeable backing layer, the adhesive layer comprising
   a) at least one pressure-sensitive adhesive based on polysiloxane,
   b) an analgesically effective amount of buprenorphine base,
   c) soluble polyvinylpyrrolidone in an amount of about 1% to about 4% of the buprenorphine base-containing pressure-sensitive adhesive layer, wherein the polyvinylpyrrolidone has K-Value of at least about 80, and
   d) levulinic acid, in an amount sufficient so that said analgesically effective amount of buprenorphine base is solubilized therein to form a mixture including said polyvinylpyrrolidone, and wherein the levulinic acid-, buprenorphine base- and polyvinylpyrrolidone-containing mixture forms dispersed deposits in the said pressure-sensitive adhesive, and wherein said buprenorphine base-containing pressure-sensitive adhesive layer is the skin contact layer.

According to a certain other embodiment of the invention alternatively the buprenorphine-containing pressure-sensitive adhesive layer comprises an additional skin contact layer.

According to certain embodiments of the invention, the TTS comprises in addition to the buprenorphine-containing self-adhesive layer structure attached thereto a larger active agent-free self-adhesive layer structure, e.g., a peripheral adhesive or overlying adhesive, for enhancing the adhesive properties of the overall transdermal therapeutic system. Said active agent-free self-adhesive layer structure comprises also a backing layer. In certain embodiments, this additional layer is beige colored. The active agent-free pressure-sensitive adhesive layer of polymer-based pressure-sensitive adhesive is e.g., based on polyacrylates or polysiloxanes. The area of said second active agent-free self-adhesive layer structure adds to the overall size of the TTS but does not add to the area of release. The pressure-sensitive adhesive in the active agent-containing and the active agent-free self-adhesive layer structures may be the same or different. If the adhesive in the active agent-free self-adhesive layer is different from that of the buprenorphine-containing layer, then pressure-sensitive adhesives selected from the group of polyacrylate-based or polyisobutylene-based pressure-sensitive adhesives can be used, and polyacrylate based pressure-sensitive adhesives are preferred, in particular pressure-sensitive adhesives based on an acrylate-vinylacetate polymer, e.g., such as those available from Henkel under the tradename Duro Tak®, e.g., Duro Tak® 387 2051. Such pressure-sensitive adhesives are provided in an organic solution of ethyl acetate and heptane. Such pressure-sensitive adhesives provide a 180° Peel at 20 minutes of at least about 20 N/25 mm, and at 24 minutes of at least about 25 N/25 cm, and at one week of at least about 30 N/25 mm and a Loop tack of at least 15 N/25 mm$^2$, or of at least 20 N/25 mm$^2$, or of at least 22 N/25 mm$^2$.

Active Agent

The TTS according to the invention comprises an analgesically effective amount of buprenorphine base or an equimolar amount of a pharmaceutically acceptable salt thereof. Pharmaceutically acceptable salts may be selected from those known in the art, such as the hydrochloride, sulphate, phosphate, tartrate, maleinate, oxalate, acetate and lactate salts. According to a preferred embodiment of the invention the active agent is included in the form of buprenorphine base. The term buprenorphine base, however, does not exclude interactions, including complexation between the buprenorphine base and other ingredients of the buprenorphine-containing layer e.g. levulinic acid.

An analgesically effective amount may vary from about 1 mg to about 50 mg, in particular from about 2 mg to about 30 mg of buprenorphine base or an equimolar amount of a pharmaceutically acceptable salt, or from about 2 mg to about 25 mg of buprenorphine base or an equimolar amount of a pharmaceutically acceptable salt thereof. According to certain embodiments, the TTS contains according to five different dosages from about 1 mg to about 4 mg, or from about 3.5 mg to about 8 mg, or from about 6.5 mg to about 16 mg, or from about 11.5 mg to about 24 mg, or from about 15 mg to about 32 mg of buprenorphine base or a an equimolar amount of a pharmaceutically acceptable salt thereof, or the TTS contains according to five different dosages from about 1 mg to about 4.5 mg, or about 3 mg, or from about 4 mg to about 9 mg, or about 6 mg, or from about 8 mg to about 14 mg, or about 12 mg, or from about 15 mg to about 20 mg, or about 18 mg or from about 20 mg to about 28 mg, or about 24 mg of buprenorphine base or a an equimolar amount of a pharmaceutically acceptable salt thereof. Further dosages are provided by transdermal therapeutic systems containing smaller or greater amounts, e.g., from about 5.5 mg to about 13 mg of buprenorphine base or an equimolar amount of a pharmaceutically acceptable salt thereof.

Pressure-Sensitive Adhesive

The pressure-sensitive adhesives used for the present invention are polymer-based pressure-sensitive adhesives. Such polymer-based pressure-sensitive adhesives may e.g., be based on polysiloxanes or polyisobutylenes. For the present invention polysiloxane-based pressure-sensitive adhesives are preferred. Such polysiloxanes adhesives need, unlike other organic pressures-sensitive adhesives, no additives like antioxidants, stabilizers, plasticizers, catalysts or other potentially extractable ingredients. These pressure-sensitive adhesives provide for suitable tack for quick bonding to various skin types, including wet skin, suitable adhesive and cohesive qualities, long lasting adhesion to the skin of up to 7 days, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin, a polysiloxane is prepared which for amine stability the residual silanol functionality is additionally capped with trimethylsiloxy groups. The dimethiconol content contributes to the viscous component of the viscoelastic behavior, and impacts the wetting and the spreadability properties of the adhesive. The resin acts as a tackifying and reinforcing agent, and participates in the elastic component. The correct balance between dimethiconol and resin provides for the correct adhesive properties.

The adhesive strength of the polysiloxanes may be sufficient for the desired skin contact. In certain embodiments of the invention a plasticizer or a tackifying agent is incorporated into the formulation to improve the adhesive characteristics of the pressure-sensitive adhesive layer. It may be advantageous in an individual case to improve the tack by adding small amounts of tackifiers such as polyterpenes, rosin derivatives, or silicone oils. In preferred embodiments, the tackifying agent is a silicone oil (e.g., 360 Medical Fluid, available from Dow Corning Corporation, Midland, Mich.).

The pressure-sensitive adhesives are supplied and used in solvents like heptane, ethyl acetate or volatile silicone fluids. For the present invention heptane is preferred. The solids content is usually between 60 and 80%.

The preferred pressure-sensitive adhesives based on polysiloxanes in accordance with the invention are characterized by a solution viscosity at 25° C. and 60% solids content in heptane of more than about 150 mPa s, or from about 200 mPa s to about 700 mPa s, in particular from about 350 mPa s to about 600 mPa s, more preferred from about 480 mPa s to about 550 mPa s, or most preferred of about 500 mPa s or alternatively from about 400 mPa s to about 480 mPa s, or most preferred of about 450 mPa s. Theses may also be characterized by a complex viscosity at 0.01 rad/s at 30° C. of less than about $1 \times 10^9$ Poise, or from about $1 \times 10^5$ to about $9 \times 10^8$ Poise, or more preferred from about $1 \times 10^5$ to about $1 \times 10^7$ Poise, or most preferred about $5 \times 10^6$ Poise, or alternatively more preferred from about $2 \times 10^7$ to about $9 \times 10^8$ Poise, or most preferred about $1 \times 10^8$ Poise.

Suitable pressure-sensitive adhesives based on polysiloxanes may be obtained from Dow Corning® BIO-PSA Standard Silicone Adhesives. Preferred are the BIO-PSA 7 4301 and BIO-PSA 7 4201 Silicone Adhesives. According to certain embodiments BIO-PSA 7 4301 is preferred and according to certain other embodiments BIO-PSA 7 4201 is preferred. To avoid excessive cold flow, BIO-PSA 7 4201 is preferred. BIO-PSA 4201 has a solution viscosity at 25° C. and about 60% solids content in heptane of 450 mPa s and a complex viscosity at 0.01 rad/s at 30° C. of $1 \times 10^8$ Poise. BIO-PSA 4301 has a solution viscosity at 25° C. and about 60% solids content in heptane of 500 mPa s and a complex viscosity at 0.01 rad/s at 30° C. of $5 \times 10^6$ Poise.

The pressure-sensitive adhesive layer of the TTS of the invention may further comprise in addition to the above mentioned ingredients a), b), c) and d), (i.e. the polymer-based pressure-sensitive adhesive, the buprenorphine, the viscosity-increasing substance/the polyvinylpyrrolidone and the carboxylic acid selected from the group of oleic acid, linoleic acid, linolenic acid and levulinic acid as described herein), other various excipients or additives, selected, for example, from the group of solubilizers, fillers, tackifiers, substances which influence the barrier properties of the stratum corneum in the sense of increasing the active agent permeability, pH regulators, and preservatives.

Substances which influence the barrier properties of the stratum corneum in the sense of increasing the active agent permeability are known to the skilled worker and the substance appropriate for the respective active agents must—if necessary—be found by means of permeation studies. Some examples are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methyloctylsulfoxide, dimethyllaurylamine, dodecylpyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate. The TTS of the invention may additionally comprise according to certain embodiments (in which the pressure-sensitive adhesive layer comprises a) the polymer-based pressure-sensitive adhesive, b) the buprenorphine, c) the viscosity-increasing substance/the polyvinylpyrrolidone and d) levulinic acid or linolenic acid or mixtures of both as the carboxylic acid as described herein) oleic and linoleic acids as substances influencing the barrier properties of the stratum corneum in the sense of increasing the active agent permeability.

Such substances as described in the previous paragraph may be included in a TTS and may be present in an amount of about 1% to about 10% by weight. In a preferred embodiment of the present invention such additional substances are however not necessary. According to an embodiment of the invention the TTS does not comprise such additional substances as mentioned in the previous paragraph.

In addition to the carboxylic acid selected from oleic acid, linoleic acid, linolenic acid, levulinic acid, the solubility of the drug can be further altered by the optional addition of an agent that increases the solubility of drug or inhibits drug crystallization in the transdermal composition, such as vinyl acetate/vinylpyrrolidone copolymer and cellulose derivatives.

Fillers such as silica gels, titanium dioxide and zinc oxide may be used in conjunction with the polymer in order to influence certain physical parameters, such as cohesion and bond strength, in the desired way.

Further one or more anti-oxidants can be added. The anti-oxidant may be selected from the group consisting of tocopherol, esters thereof, e.g. α-tocopherol acetate, ascorbyl palmitate, ascorbic acid, butylhydroxytoluene, butylhydroxyanisole or propyl gallate, preferably ascorbyl palmitate. The antioxidant may be conveniently present in an amount of from about 0.01 to about 0.5%, e.g. 0.05 to 0.30, e.g. 0.18% or 0.2% of the buprenorphine-containing pressure-sensitive adhesive layer.

Buprenorphine-Containing Self-Adhesive Layer Structure

In accordance with the invention, the buprenorphine-containing self-adhesive layer structure comprises a buprenorphine-impermeable backing layer, and a buprenorphine-containing pressure-sensitive adhesive layer coated thereon. In a preferred embodiment, the buprenorphine-containing self-adhesive layer structure consists of these two elements.

The buprenorphine-containing pressure-sensitive adhesive layer may be coated at any dry weight, but is preferably coated at a dry weight of more than about 6 mg/cm² (about 60 g/m²), or of more than about 8 mg/cm² (about 80 g/m²), or ranging from about 6 mg/cm² (about 60 g/m²) to about 14 mg/cm² (about 140 g/m²), or from about 8 mg/cm² (about 80 g/m²) to about 14 mg/cm² (about 140 g/m²). Specifically, the dry weight is more than about 10 mg/cm² (about 100 g/m²), or ranges from about 10 mg/cm² (about 100 g/m²) to about 13 mg/cm² (about 130 g/m²), or ranges from about 11.5 mg/cm² (about 115 g/m²) to about 12.5 mg/cm² (about 125 g/m²), or is specifically about 12 mg/cm² (about 120 g/m²).

The dry buprenorphine-containing pressure-sensitive adhesive layer preferably contains buprenorphine base, but may contain an equimolar amount of a pharmaceutically acceptable salt. According to the invention, preferably more than 5%, or more than about 6%, or more than about 7%, or more than about 8%, or more than about 9%, or from about 6% to about 20%, or from about 7% to about 20%, or from about 8% to about 20%, or from about 9% to about 20%, or from about 6% to about 15%, or from about 7% to about 15%, or from about 8 to about 15%, or from about 9 to about 15% buprenorphine base or an equimolar amount of a pharmaceutically acceptable salt based on the total dry weight of the dry buprenorphine-containing pressure-sensitive adhesive layer is contained in the dry buprenorphine-containing pressure-sensitive adhesive layer. In a specific embodiment, about 10% buprenorphine base is contained in the dry buprenorphine-containing pressure-sensitive adhesive layer.

Preferably, the TTS contains in the pressure-sensitive adhesive layer more than about 0.55 mg/cm$^2$, or more than about 0.6 mg/cm$^2$, or more than about 0.7 mg/cm$^2$, or more than about 0.8 mg/cm$^2$, or more than about 0.9 mg/cm$^2$, or more than about 1 mg/cm$^2$, or more than about 1.1 mg/cm$^2$, buprenorphine base, or from about 0.55 mg/cm$^2$ to about 2 mg/cm$^2$, or from about 0.6 mg/cm$^2$ to about 2 mg/cm$^2$, or from about 0.7 mg/cm$^2$ to about 2 mg/cm$^2$, or from about 0.8 mg/cm$^2$ to about 2 mg/cm$^2$, or from about 0.9 mg/cm$^2$ to about 2 mg/cm$^2$, or from about 1 mg/cm$^2$ to about 2 mg/cm$^2$, or from about 1.1 mg/cm$^2$ to about 2 mg/cm$^2$ buprenorphine base or contains about 1.2 mg/cm$^2$ buprenorphine base. The TTS may also contain equimolar amounts of pharmaceutically acceptable salts.

In order to provide the desired delivery rate of buprenorphine, a carboxylic acid is present. The carboxylic acid may be selected from the group consisting of $C_3$ to $C_{24}$ carboxylic acids including oleic acid, linoleic acid, linolenic acid, levulinic acid and mixtures thereof, wherein levulinic acid is preferred. Alternatively or in addition, a substance selected from the group consisting of alcohols and esters may be present. The buprenorphine is in mixture with, e.g., dissolved in, the carboxylic acid, e.g., the levulinic acid, and this mixture, e.g., solution, is dispersed in the form of small deposits, e.g., droplets, in the matrix layer. Buprenorphine, with its known physicochemical properties, namely its poor solubility, its comparatively high melting point of 216° C., and its high molecular weight, tends readily towards crystallization. For this reason, a solubilizer with at least one acidic group (alternatively with an alcoholic or ester group) is used in order to prevent the buprenorphine from crystallizing during the storage of the pharmaceutical form. Buprenorphine and levulinic acid have an extremely low solubility in polysiloxanes. As a consequence of this, it is possible to solubilize buprenorphine in levulinic acid and to disperse this mixture in the form of small deposits (e.g. droplets) in a matrix layer prepared on the basis of polysiloxanes as described herein.

Levulinic acid is sparingly soluble in the organic solvents of the adhesives. Consequently, the liquid mixture of buprenorphine and levulinic acid can be dispersed in the solution of the adhesive, with the dispersion being retained following removal of the solvent. In a matrix layer of this kind, the solubility of the buprenorphine is dependent virtually only on the amount of the levulinic acid.

The amount of the dispersed mixture of buprenorphine, e.g., buprenorphine base, and the carboxylic acid, e.g., levulinic acid, can be up to about 40% by weight, it being preferred not to exceed about 25% or about 20% by weight and ranges from about 15% to about 25%, or from about 15% to about 20%, or from about 17% to about 20%. The size of the deposit, e.g., droplet (diameter) itself ought preferably not to exceed about 150 μm, or ranges from about 1 to about 150 μm, preferably from about 1 to about 50 μm, or from about 5 to about 50 μm, or from about 1 to about 25 μm or from about 5 to about 25 μm. The preferred size is dependent, furthermore, on the thickness of the matrix layer.

Since the carboxylic acid, e.g., the levulinic acid, can likewise be absorbed through the skin, the amount in the TTS becomes less as the time of application elapses, and leads to a reduction of the solubility of buprenorphine. As a result, the decrease in the thermodynamic activity of buprenorphine due to depletion is compensated by the reduced drug solubility in the buprenorphine/levulinic acid deposits.

According to the invention the dry buprenorphine-containing pressure-sensitive adhesive layer contains more than about 5%, or more than about 6%, or more than about 7%, or more than about 8%, or more than about 9%, or from about 6% to about 20%, or from about 7% to about 20%, or from about 8 to about 20%, or from about 9 to about 20%, or from about 5% to about 15%, or from about 6% to about 15%, or from about 6% to about 9%, or from about 9% to about 15% carboxylic acid, e.g., levulinic acid based on the total dry weight of the dry buprenorphine-containing pressure-sensitive adhesive layer. In a specific embodiment the dry buprenorphine-containing pressure-sensitive adhesive layer contains from about 6% to about 11% levulinic acid, or from about 6% to about 9% or from about 9% to about 15% levulinic acid, or about 7% levulinic acid or about 10% levulinic acid. According to a specific embodiment the pressure-sensitive adhesive layer contains the same %-amount of levulinic acid and buprenorphine base or equimolar amounts of pharmaceutically acceptable salts. According to another specific embodiment, the pressure-sensitive adhesive layer contains less %-amount of levulinic acid than it contains %-amount of buprenorphine base or equimolar amounts of pharmaceutically acceptable salts.

According to a specific embodiment, the pressure-sensitive adhesive layer contains more than about 9% to about 15% buprenorphine base and from about 6% to about 9% levulinic acid or from more than about 9% to about 15% buprenorphine base, and from about 9% to about 15% levulinic acid based on the total dry weight.

According to a certain embodiment, the pressure-sensitive adhesive layer is coated at a dry weight of from about 10 mg/cm$^2$ to about 14 mg/cm$^2$, or from about 11.5 mg/cm$^2$ to about 12.5 mg/cm$^2$, or is about 12 mg/cm$^2$, and the dry pressure-sensitive adhesive layer contains from about 7% to about 13% or from about 8% to about 12%, or from about 9% to about 11% or about 10% buprenorphine base and from about 6% to about 8%, or about 7% levulinic acid. In a specific embodiment the dry pressure-sensitive adhesive layer has a dry weight of about 12 mg/cm$^2$ and contains about 7% levulinic acid and about 10% buprenorphine base.

According to a certain other embodiment, the pressure-sensitive adhesive layer is coated at a dry weight of from about 10 mg/cm$^2$ to about 14 mg/cm$^2$, or from about 11.5 mg/cm$^2$ to about 12.5 mg/cm$^2$, or is about 12 mg/cm$^2$, and the dry pressure-sensitive adhesive layer contains from about 7% to about 13% or from about 8% to about 12%, or from about 9% to about 11% or about 10% buprenorphine base and from about 8 to about 12% or about 10% levulinic acid. In a specific embodiment, the dry pressure-sensitive adhesive layer has a dry weight of about 12 mg/cm$^2$, and contains about 10% levulinic acid and about 10% buprenorphine base.

In accordance with the above, the TTS contains more than about 0.55 mg/cm$^2$, or more than about 0.6 mg/cm$^2$, or more than about 0.7 mg/cm$^2$, or more than about 0.8 mg/cm$^2$, or more than about 0.9 mg/cm$^2$, or more than about 1 mg/cm$^2$, or more than about 1.1 mg/cm$^2$ buprenorphine base or from about 0.6 mg/cm$^2$ to about 2 mg/cm$^2$, or from about 0.7 mg/cm$^2$ to about 2 mg/cm$^2$, or from about 0.8 mg/cm$^2$ to about 2 mg/cm$^2$, or from about 0.9 mg/cm$^2$ to about 2 mg/cm$^2$, or from about 1 mg/cm$^2$ to about 2 mg/cm$^2$, or from about 1.1 mg/cm$^2$ to about 2 mg/cm$^2$ buprenorphine base or contains about 1.2 mg/cm$^2$ buprenorphine base or an equimolar amount of a pharmaceutically acceptable salt thereof. In certain embodiments, buprenorphine base is preferred. According to a specific embodiment, the pressure-sensitive adhesive layer contains the same amounts of levulinic acid and buprenorphine base. According to another specific embodiment, the pressure-sensitive adhesive layer contains less levulinic acid than it contains buprenorphine base or an equimolar amount of a pharmaceutically acceptable salt thereof.

According to a certain embodiment of the invention, the pressure-sensitive adhesives in the buprenorphine-containing layer and in the active agent-free layer are different, and the adhesive in the active agent-free layer is a pressure-sensitive adhesive based on polyacrylates. According to certain other embodiments, the adhesive in the active agent-containing and the active agent-free layer are the same and are an amine-resistant pressure-sensitive adhesive based on polysiloxane. According to certain embodiments, the polysiloxane is a product of the condensation reaction of silanol endblocked polydimethylsiloxane with a silica resin and the residual silanol functionality is capped with trimethylsiloxy groups and characterized by a solution viscosity at 25° C. and about 60% solids content in heptanes of about 500 mPa s or of about 450 mPa s. According to certain embodiments, the buprenorphine-containing pressure-sensitive adhesive layer is coated at a dry weight of about 12 mg/cm$^2$ and contains about 10% buprenorphine base and about 10% levulinic acid.

According to certain embodiments, the area of release ranges from about 1 cm$^2$ to about 38 cm$^2$, or is less than 25 cm$^2$, or less than 22 cm$^2$, or ranges from about 1.5 to about 25 cm$^2$, or from about 1.5 to about 22 cm$^2$, or from about 1.5 to about 20 cm$^2$, or is about 3 cm$^2$, or about 6 cm$^2$, or about 10 cm$^2$, or about 15 cm$^2$ or about 20 cm$^2$.

According to certain embodiments, the TTS contains from about 1 mg to about 32 mg of buprenorphine base or an equimolar amount of a pharmaceutically acceptable salt thereof, or from about 1 mg to about 28 mg, or from about 2 mg to about 25 mg, or from about 2 mg to about 24 mg of buprenorphine base or an equimolar amount of a pharmaceutically acceptable salt thereof. Considering five different increasing dosage strengths, the TTS in specific cases preferably contains a) from about 1 mg to about 4 mg, or from about 1 mg to about 4.5 mg, preferably from about 1 mg to about 3.5 mg, or from about 2 mg to about 4 mg, more preferably from about 1 mg to about 3 mg, or from about 2.5 mg to about 4 mg, or about 3 mg buprenorphine base or an equimolar amount of a pharmaceutically acceptable salt thereof, or b) from about 3.5 mg to about 8 mg, or from about 4 mg to about 9 mg, preferably from about 3.5 mg to about 7 mg, or from about 5 mg to about 8 mg, more preferably from about 3.5 mg to about 6 mg, or from about 5 mg to about 7 mg, or about 6 mg buprenorphine base or an equimolar amount of a pharmaceutically acceptable salt thereof, or c) from about 6.5 mg to about 16 mg, or from about 8 mg to about 14 mg, preferably from about 6.5 mg to about 14 mg, or from about 10 mg to about 14 mg, more preferably from about 6.5 mg to about 11 mg, or from about 11 mg to about 13 mg, or about 12 mg buprenorphine base or an equimolar amount of a pharmaceutically acceptable salt thereof, or d) from about 11.5 mg to about 24 mg, or from about 15 mg to about 20 mg, preferably from about 11.5 mg to about 21 mg, or from about 16 mg to about 19 mg, more preferably from about 11.5 mg to about 14 mg, or from about 17 mg to about 19 mg, or about 18 mg buprenorphine base or an equimolar amount of a pharmaceutically acceptable salt thereof, or e) from about 15 mg to about 32 mg, or from about 20 mg to about 28 mg, preferably from about 15 mg to about 28 mg, or from about 21 mg to about 26 mg, more preferably from about 15 mg to about 24 mg, or from about 22 mg to about 25 mg, or about 24 mg of buprenorphine base or an equimolar amount of a pharmaceutically acceptable salt thereof.

Correspondingly the area of release ranges from about 1 cm$^2$ to about 38 cm$^2$, or from 1.5 cm$^2$ to about 24 cm$^2$, or ranges from 1.5 cm$^2$ to about 22 cm$^2$, or ranges from 1.5 cm$^2$ to about 20 cm$^2$ and with respect to the five specific preferred dosage strengths a) to e)

a) ranges from about 1 cm$^2$ to about 4.8 cm$^2$, or from about 1.5 cm$^2$ to about 5.5 cm$^2$, preferably from about 1 cm$^2$ to about 4.5 cm$^2$, or from about 2 cm$^2$ to about 4 cm$^2$, more preferably from about 2.5 cm$^2$ to about 4 cm$^2$, or from about 2 cm$^2$ to about 3 cm$^2$, or is about 2.5 cm$^2$, or b) ranges from about 3 cm$^2$ to about 9.5 cm$^2$, or from about 3 cm$^2$ to about 9 cm$^2$, preferably from about 3 cm$^2$ to about 9 cm$^2$, or from about 4.5 cm$^2$ to about 7.5 cm$^2$, more preferably from about 5 cm$^2$ to about 8 cm$^2$, or from about 4.5 cm$^2$ to about 6 cm$^2$, or is about 5 cm$^2$, or c) ranges from about 6 cm$^2$ to about 19 cm$^2$, or from about 6 cm$^2$ to about 14 cm$^2$, preferably from about 6 cm$^2$ to about 18 cm$^2$, or from about 8 cm$^2$ to about 12 cm$^2$, more preferably from about 10 cm$^2$ to about 16 cm$^2$, or from about 9 cm$^2$ to about 11 cm$^2$, or is about 10 cm$^2$, or d) ranges from about 12 cm$^2$ to about 28.5 cm$^2$, or from about 13 cm$^2$ to about 17 cm$^2$, preferably from about 12 cm$^2$ to about 27 cm$^2$, or from about 13 cm$^2$ to about 16 cm$^2$, more preferably from about 17 cm$^2$ to about 23 cm$^2$, or from about 14 cm$^2$ to about 16 cm$^2$, or is about 15 cm$^2$, or e) ranges from about 16 cm$^2$ to about 38 cm$^2$, or from about 16 cm$^2$ to about 24 cm$^2$, preferably or from about 16 cm$^2$ to about 35 cm$^2$, or from about 17 cm$^2$ to about 22 cm$^2$, more preferably from about 23.5 cm$^2$ to about 32 cm$^2$, or from about 18 cm$^2$ to about 21 cm$^2$, or is about 20 cm$^2$.

A further TTS providing a dosage strength between strength b) and c) contains from about 5.5 mg to about 13 mg buprenorphine base or an equimolar amount of a pharmaceutically acceptable salt thereof and the area of release ranges from about 5 cm$^2$ to about 14 cm$^2$, preferably from about 5 cm$^2$ to about 13.5 cm$^2$.

In such embodiments the dry pressure-sensitive adhesive layer preferably comprises a pressure-sensitive adhesive based on polysiloxanes and has preferably a dry weight of about 6 mg/cm$^2$, 7.5 mg/cm$^2$, 8 mg/cm$^2$, 9 mg/cm$^2$, 10.5 mg/cm$^2$, or 12 mg/cm$^2$ and contains 10% buprenorphine base.

According to certain preferred embodiments, the TTS contains with respect to five dosage strengths a) to e) the following amounts of buprenorphine base or an equimolar amount of a pharmaceutically acceptable salt thereof and provides the following corresponding area of release ranges:

a)

| a) | about 1 cm$^2$ to about 4.8 cm$^2$ | about 1 cm$^2$ to about 4.5 cm$^2$ | about 2.5 cm$^2$ to about 4 cm$^2$ |
|---|---|---|---|
| about 1 mg to about 4 mg | X | X | X |
| about 1 mg to about 3.5 mg | X | X | X |
| about 1 mg to about 3 mg | X | X | X | b)

| b) | about 3 cm$^2$ to about 9.5 cm$^2$ | about 3 cm$^2$ to about 9 cm$^2$ | about 5 cm$^2$ to about 8 cm$^2$ |
|---|---|---|---|
| about 3.5 mg to about 8 mg | X | X | X |
| about 3.5 mg to about 7 mg | X | X | X |
| about 3.5 mg to about 6 mg | X | X | X | c)

| c) | about 6 cm$^2$ to about 19 cm$^2$ | about 6 cm$^2$ to about 18 cm$^2$ | about 10 cm$^2$ to about 16 cm$^2$ |
|---|---|---|---|
| about 6.5 mg to about 16 mg | X | X | X |
| about 6.5 mg to about 14 mg | X | X | X |
| about 6.5 mg to about 11 mg | X | X | X | d)

| d) | about 12 cm$^2$ to about 28.5 cm$^2$ | about 12 cm$^2$ to about 27 cm$^2$ | about 17 cm$^2$ to about 23 cm$^2$ |
|---|---|---|---|
| about 11.5 mg to about 24 mg | X | X | X |
| about 11.5 mg to about 21 mg | X | X | X |
| about 11.5 mg to about 14 mg | X | X | X | e)

| e) | about 16 cm$^2$ to about 38 cm$^2$ | about 16 cm$^2$ to about 35 cm$^2$ | about 23.5 cm$^2$ to about 32 cm$^2$ |
|---|---|---|---|
| about 15 mg to about 32 mg | X | X | X |
| about 15 mg to about 28 mg | X | X | X |
| about 15 mg to about 24 mg | X | X | X |

The further TTS providing the dosage strength between strength b) and c) provides from about 5.5 mg to about 13 mg buprenorphine base or an equimolar amount of a pharmaceutically acceptable salt thereof and the area of release ranges from about 5 cm$^2$ to about 14 cm$^2$, or from about 5.5 mg to about 13 mg buprenorphine base or an equimolar amount of a pharmaceutically acceptable salt thereof and the area of release ranges from about 5 cm$^2$ to about 13.5 cm$^2$.

Set of Transdermal Therapeutic Systems

For the treatment of pain a patient needs to be titrated to the individual dose of buprenorphine to adequately control the pain. In order to meet the individual requirements five different dosage strengths are provided in accordance with the invention.

According to one aspect, the invention relates to a set of two (first and second, or second and third, or third and fourth, or fourth and fifth TTS, or any other combination of two of the five different dosage strengths), three (first to third, or second to fourth or third to fifth TTS, or any other combination of three of the five different dosage strengths), four (first to fourth or second to fifth TTS, or any other combination of four of the five different dosage strengths) or five (first to fifth TTS) different transdermal therapeutic systems in accordance with the invention, wherein: the first transdermal therapeutic system provides a size of said buprenorphine-containing pressure-sensitive adhesive layer providing the area of release ranging from about 1 cm$^2$ to about 4.8 cm$^2$, or from about 1.5 cm$^2$ to about 5.5 cm$^2$ and contains an amount of said buprenorphine from about 1 mg to about 4 mg, or from about 1 mg to about 4.5 mg buprenorphine base or an equimolar amount of a pharmaceutically acceptable salt thereof; and the second transdermal therapeutic system provides a size of said buprenorphine-containing pressure-sensitive adhesive layer providing the area of release ranging from about 3 cm$^2$ to about 9.5 cm$^2$, or from about 3 cm$^2$ to about 9 cm$^2$ and contains an amount of said buprenorphine from about 3.5 mg to about 8 mg, or from about 4 mg to about 9 mg buprenorphine base or an equimolar amount of a pharmaceutically acceptable salt thereof; and the third transdermal therapeutic system provides a size of said buprenorphine-containing pressure-sensitive adhesive layer providing the area of release ranging from about 6 cm$^2$ to about 19 cm$^2$, or from about 6 cm$^2$ to about 14 cm$^2$ and contains an amount of said buprenorphine from about 6.5 mg to about 16 mg, or from about 8 mg to about 14 mg buprenorphine base or an equimolar amount of a pharmaceutically acceptable salt thereof; and the fourth transdermal therapeutic system provides a size of said buprenorphine-containing pressure-sensitive adhesive layer providing the area of release ranging from about 12 cm$^2$ to about 28.5 cm$^2$, or from about 13 cm$^2$ to about 17 cm$^2$ and contains an amount of said buprenorphine from about 11.5 mg to about 24 mg, or from about 15 mg to about 20 mg buprenorphine base or an equimolar amount of a pharmaceutically acceptable salt thereof; and the fifth transdermal therapeutic system provides a size of said buprenorphine-containing pressure-sensitive adhesive layer providing the area of release ranging from about 16 $cm^2$ to about 38 $cm^2$, or from about 16 $cm^2$ to about 24 $cm^2$ and contains an amount of said buprenorphine from about 15 mg to about 32 mg, or from about 20 mg to about 28 mg buprenorphine base or an equimolar amount of a pharmaceutically acceptable salt thereof. The set of two to five different transdermal therapeutic systems in accordance with this paragraph can be expanded by one or more further transdermal therapeutic system(s) which may provide smaller, greater or intermediate areas of release and amounts of buprenorphine compared with the five different transdermal therapeutic systems described above, preferably the set of two to five different transdermal therapeutic systems is expanded by a further transdermal therapeutic system which provides a size of said buprenorphine-containing pressure-sensitive adhesive layer providing the area of release ranging from about 5 $cm^2$ to about 14 $cm^2$ and contains an amount of said buprenorphine from about 5.5 mg to about 13 mg buprenorphine base or an equimolar amount of a pharmaceutically acceptable salt thereof, providing an intermediate transdermal therapeutic system between the second and the third transdermal therapeutic system. Alternatively, one of the transdermal therapeutic systems of the set of two to five different transdermal therapeutic systems can be replaced by such a further transdermal therapeutic system.

The invention relates also to set of transdermal therapeutic systems, wherein:
the first transdermal therapeutic system provides a size of said buprenorphine-containing pressure-sensitive adhesive layer providing the area of release ranging from about 1 $cm^2$ to about 4.5 $cm^2$, or from about 2 $cm^2$ to about 4 $cm^2$ and contains an amount of said buprenorphine from about 1 mg to about 4 mg, or from about 1 mg to about 3.5 mg, or from about 2 mg to about 4 mg buprenorphine base or an equimolar amount of a pharmaceutically acceptable salt thereof; and
the second transdermal therapeutic system provides a size of said buprenorphine-containing pressure-sensitive adhesive layer providing the area of release ranging from about 3 $cm^2$ to about 9 $cm^2$, or from about 4.5 $cm^2$ to about 7.5 $cm^2$ and contains an amount of said buprenorphine from about 3.5 mg to about 8 mg, or from about 3.5 mg to about 7 mg, or from about 5 mg to about 8 mg buprenorphine base or an equimolar amount of a pharmaceutically acceptable salt thereof; and
the third transdermal therapeutic system provides a size of said buprenorphine-containing pressure-sensitive adhesive layer providing the area of release ranging from about 6 $cm^2$ to about 18 $cm^2$, or from about 8 $cm^2$ to about 12 $cm^2$ and contains an amount of said buprenorphine from about 6.5 mg to about 16 mg, or from about 6.5 mg to about 14 mg, or from about 10 mg to about 14 mg buprenorphine base or an equimolar amount of a pharmaceutically acceptable salt thereof; and
the fourth transdermal therapeutic system provides a size of said buprenorphine-containing pressure-sensitive adhesive layer providing the area of release ranging from about 12 $cm^2$ to about 27 $cm^2$, or from about 13 $cm^2$ to about 16 $cm^2$ and contains an amount of said buprenorphine from about 11.5 mg to about 21 mg, or from about 11.5 mg to about 24 mg, or from about 16 mg to about 19 mg buprenorphine base or an equimolar amount of a pharmaceutically acceptable salt thereof; and
the fifth transdermal therapeutic system provides a size of said buprenorphine-containing pressure-sensitive adhesive layer providing the area of release ranging from about 16 $cm^2$ to about 35 $cm^2$, or from about 17 $cm^2$ to about 22 $cm^2$ and contains an amount of said buprenorphine from about 15 mg to about 32 mg, or from about 15 mg to about 28 mg, or from about 21 mg to about 26 mg buprenorphine base or an equimolar amount of a pharmaceutically acceptable salt thereof. The set of two to five different transdermal therapeutic systems in accordance with this paragraph can be expanded by one or more further transdermal therapeutic system(s) which may provide smaller, greater or intermediate areas of release and amounts of buprenorphine compared with the five different transdermal therapeutic systems described above, preferably the set of two to five different transdermal therapeutic systems is expanded by a further transdermal therapeutic system which provides a size of said buprenorphine-containing pressure-sensitive adhesive layer providing the area of release ranging from about 5 $cm^2$ to about 13.5 $cm^2$ and contains an amount of said buprenorphine from about 5.5 mg to about 13 mg buprenorphine base or an equimolar amount of a pharmaceutically acceptable salt thereof, providing an intermediate transdermal therapeutic system between the second and the third transdermal therapeutic system. Alternatively, one of the transdermal therapeutic systems of the set of two to five different transdermal therapeutic systems can be replaced by such a further transdermal therapeutic system.

The invention relates also to set of different transdermal therapeutic, wherein:
the first transdermal therapeutic system provides a size of said buprenorphine-containing pressure-sensitive adhesive layer providing the area of release ranging from about 2.5 $cm^2$ to about 4 $cm^2$, or from about 2 $cm^2$ to about 3 $cm^2$ and contains an amount of said buprenorphine from about 1 mg to about 3 mg, or from about 2.5 mg to about 4 mg buprenorphine base or an equimolar amount of a pharmaceutically acceptable salt thereof; and
the second transdermal therapeutic system provides a size of said buprenorphine-containing pressure-sensitive adhesive layer providing the area of release ranging from about 5 $cm^2$ to about 8 $cm^2$, or from about 4.5 $cm^2$ to about 6 $cm^2$ and contains an amount of said buprenorphine from about 3.5 mg to about 6 mg, or from about 5 mg to about 7 mg buprenorphine base or an equimolar amount of a pharmaceutically acceptable salt thereof; and
the third transdermal therapeutic system provides a size of said buprenorphine-containing pressure-sensitive adhesive layer providing the area of release ranging from about 10 $cm^2$ to about 16 $cm^2$, or from about 9 $cm^2$ to about 11 $cm^2$ and contains an amount of said buprenorphine from about 6.5 mg to about 11 mg, or from about 11 mg to about 13 mg buprenorphine base or an equimolar amount of a pharmaceutically acceptable salt thereof; and
the fourth transdermal therapeutic system provides a size of said buprenorphine-containing pressure-sensitive adhesive layer providing the area of release ranging from about 17 $cm^2$ to about 23 $cm^2$, or from about 14 $cm^2$ to about 16 $cm^2$ and contains an amount of said buprenorphine from about 11.5 mg to about 14 mg, or from about 17 mg to about 19 mg buprenorphine base or an equimolar amount of a pharmaceutically acceptable salt thereof; and
the fifth transdermal therapeutic system provides a size of said buprenorphine-containing pressure-sensitive adhesive layer providing the area of release ranging from about 23.5 $cm^2$ to about 32 $cm^2$, or from about 18 $cm^2$ to about 21 $cm^2$ and contains an amount of said buprenorphine from about 15 mg to about 24 mg, or from about 22 mg to about 25 mg buprenorphine base or an equimolar amount of a pharmaceutically acceptable salt thereof. The set of two to five different transdermal therapeutic systems in accordance with this paragraph can be expanded by one or more further transdermal therapeutic system(s) which may provide smaller, greater or intermediate areas of release and amounts of buprenorphine compared with the five different transdermal therapeutic systems described above, preferably the set of two to five different transdermal therapeutic systems is expanded by a further transdermal therapeutic system which provides a size of said buprenorphine-containing pressure-sensitive adhesive layer providing the area of release ranging from about 5 cm$^2$ to about 13.5 cm$^2$ and contains an amount of said buprenorphine from about 5.5 mg to about 13 mg buprenorphine base or an equimolar amount of a pharmaceutically acceptable salt thereof, providing an intermediate transdermal therapeutic system between the second and the third transdermal therapeutic system. Alternatively, one of the transdermal therapeutic systems of the set of two to five different transdermal therapeutic systems can be replaced by such a further transdermal therapeutic system.

In a further aspect of the invention a transdermal therapeutic system selected from a set of transdermal therapeutic systems as described in the previous paragraphs is provided wherein buprenorphine is present in the form of buprenorphine base and wherein the first transdermal therapeutic system when tested in a comparative clinical study is bioequivalent to a reference product having an area of release of about 6.25 cm$^2$ and providing a nominal mean release rate of about 5 µg/hr over about 168 hours of administration, the second transdermal therapeutic system when tested in a comparative clinical study is bioequivalent to a reference product having an area of release of about 12.5 cm$^2$ and providing a nominal mean release rate of about 10 µg/hr over about 168 hours of administration, the third transdermal therapeutic system when tested in a comparative clinical study is bioequivalent to a reference product having an area of release of about 25 cm$^2$ and providing a nominal mean release rate of about 20 µg/hr over about 168 hours of administration, the fourth transdermal therapeutic system when tested in a comparative clinical study is bioequivalent to a reference product having an area of release of about 37.5 cm$^2$ and providing a nominal mean release rate of about 30 µg/hr over about 168 hours of administration, the fifth transdermal therapeutic system when tested in a comparative clinical study is bioequivalent to a reference product having an area of release of about 50 cm$^2$ and providing a nominal mean release rate of about 40 µg/hr over about 168 hours of administration, the further transdermal therapeutic system when tested in a comparative clinical study is bioequivalent to a reference product having an area of release of about 18.75 cm$^2$ and providing a nominal mean release rate of about 15 µg/hr over about 168 hours of administration, wherein the reference product is prepared by the following steps:
1. mixing of 1,139 g of a 47.83% polyacrylate solution of a self-crosslinked acrylate copolymer of 2-ethylhexyl acrylate, vinyl acetate, acrylic acid (solvent: ethyl acetate:heptanes:isopropanol:toluene:acetylacetonate in the ratio of 37:26:26:4:1), 100 g of levulinic acid, 150 g of oleyl oleate, 100 g of polyvinylpyrrolidone, 150 g of ethanol, 200 g of ethyl acetate, and 100 g of buprenorphine base to provide a mixture;
2. stirring the mixture of step 1 for about 2 hours and controlling the dissolution of all solids visually whereas controlling the evaporation loss by reweighing and replenishing the possible solvent loss by ethyl acetate;
3. subsequently applying the mixture on a transparent polyester film in such a manner that the mass per unit area of the dry adhesive layer amounts to about 80 g/m$^2$ wherein the polyester film is rendered removable by means of siliconization and serves as protective layer;
4. removing the solvents of the mixture applied on a transparent polyester film in step 3 by drying with heated air which is led over a moist lane resulting in evaporation of the solvents, but also in melting of the levulinic acid and covering the adhesive film with a polyester foil;
5. punching the area of release of 6.25 cm$^2$, 12.5 cm$^2$, 18.75 cm$^2$, 25 cm$^2$, 37.5 cm$^2$ and 50 cm$^2$, respectively, by means of suitable cutting tools and removing the edges left between the individual systems.

According to one aspect, the invention relates to a transdermal therapeutic system described as first transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 6.25 cm$^2$.

According to one aspect, the invention relates to a transdermal therapeutic system described as second transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 12.5 cm$^2$.

According to one aspect, the invention relates to a transdermal therapeutic system described as third transdermal therapeutic system in the previous paragraphs wherein buprenorphine is present in the form of buprenorphine base and which is when tested in a comparative clinical study bioequivalent to the commercial product BuTrans®, also known as Norspan®, having an area of release of 25 cm$^2$.

According to one aspect, the invention relates to a transdermal therapeutic system comprising buprenorphine for the transdermal administration of buprenorphine selected from:
a first transdermal therapeutic system providing a size of the area of release ranging from about 1 cm$^2$ to about 4.8 cm$^2$ and containing an amount of said buprenorphine from 1 mg to about 4 mg buprenorphine base or an equimolar amount of a pharmaceutically acceptable salt thereof and providing a nominal mean release rate of about 5 µg/hr and/or providing a mean AUCt of more than 7,000 pg·hr/ml, preferably more than 8,000 pg·hr/ml, or of from more than 7,000 pg·hr/ml to about 16,000 pg·hr/ml, or of from more than 8,000 pg·hr/ml to about 16,000 pg·hr/ml over about 168 hours of administration after a single-dose administration to a subject population;
a second transdermal therapeutic system providing a size of the area of release ranging from about 3 cm$^2$ to about 9.5 cm$^2$ and containing an amount of said buprenorphine from about 3.5 mg to about 8 mg buprenorphine base or an equimolar amount of a pharmaceutically acceptable salt thereof and providing a nominal mean release rate of about 10 µg/hr and/or providing a mean AUCt of more than 14,000 pg·hr/ml, preferably of more than 16,000 pg·hr/ml, or of from more than 14,000 pg·hr/ml to about 32,000 pg·hr/ml, or of from more than 16,000 pg·hr/ml to about 32,000 pg·hr/ml over about 168 hours of administration after a single-dose administration to a subject population; and a third transdermal therapeutic system providing a size of the area of release ranging from about 6 cm² to about 19 cm² and containing an amount of said buprenorphine from about 6.5 mg to about 16 mg buprenorphine base or an equimolar amount of a pharmaceutically acceptable salt thereof and providing a nominal mean release rate of about 20 µg/hr and/or providing a mean AUCt of more than 28,000 pg·hr/ml, preferably of more than 32,000 pg·hr/ml, or of from more than 28,000 pg·hr/ml to about 64,000 pg·hr/ml, or of from more than 32,000 pg·hr/ml to about 64,000 pg·hr/ml over about 168 hours of administration after a single-dose administration to a subject population; and a fourth transdermal therapeutic system providing a size of the area of release ranging from about 12 cm² to about 28.5 cm² and containing an amount of said buprenorphine from about 11.5 mg to about 24 mg buprenorphine base or an equimolar amount of a pharmaceutically acceptable salt thereof and providing a nominal mean release rate of about 30 µg/hr and/or providing a mean AUCt of more than 42,000 pg·hr/ml, preferably of more than 48,000 pg·hr/ml, or of from more than 42,000 pg·hr/ml to about 96,000 pg·hr/ml, or of from more than 48,000 pg·hr/ml to about 96,000 pg·hr/ml over about 168 hours of administration after a single-dose administration to a subject population; and a fifth transdermal therapeutic system providing a size of the area of release ranging from about 16 cm² to about 38 cm² and containing an amount of said buprenorphine from about 15 mg to about 32 mg buprenorphine base or an equimolar amount of a pharmaceutically acceptable salt thereof and providing a nominal mean release rate of about 40 µg/hr and/or providing a mean AUCt of more than 62,000 pg·hr/ml, preferably of more than 64,000 pg·hr/ml, or of from more than 62,000 pg·hr/ml to about 128,000 pg·hr/ml, or of from more than 64,000 pg·hr/ml to about 128,000 pg·hr/ml over about 168 hours of administration after a single-dose administration to a subject population; and a further transdermal therapeutic system providing a size of the area of release ranging from about 5 cm² to about 14 cm² and containing an amount of said buprenorphine from about 5.5 mg to about 13 mg buprenorphine base or an equimolar amount of a pharmaceutically acceptable salt thereof and providing a nominal mean release rate of about 15 µg/hr and/or providing a mean AUCt of more than 22,000 pg·hr/ml, preferably of more than 24,000 pg·hr/ml, or of from more than 22,000 pg·hr/ml to about 48,000 pg·hr/ml, or of from more than 24,000 pg·hr/ml to about 48,000 pg·hr/ml over about 168 hours of administration after a single-dose administration to a subject population.

According to one aspect, the invention relates to a transdermal therapeutic system comprising buprenorphine for the transdermal administration of buprenorphine selected from:
a first transdermal therapeutic system providing a size of the area of release ranging from about 1 cm² to about 4.5 cm² and containing an amount of said buprenorphine from 1 mg to about 4 mg, or from 1 mg to about 3.5 mg buprenorphine base or an equimolar amount of a pharmaceutically acceptable salt thereof and providing a nominal mean release rate of about 5 µg/hr and/or providing a mean AUCt of more than 7,000 pg·hr/ml, preferably more than 8,000 pg·hr/ml, or of from more than 7,000 pg·hr/ml to about 16,000 pg·hr/ml, or of from more than 8,000 pg·hr/ml to about 16,000 pg·hr/ml over about 168 hours of administration after a single-dose administration to a subject population;

a second transdermal therapeutic system providing a size of the area of release ranging from about 3 cm² to about 9 cm² and containing an amount of said buprenorphine from about 3.5 mg to about 8 mg, or from about 3.5 mg to about 7 mg buprenorphine base or an equimolar amount of a pharmaceutically acceptable salt thereof and providing a nominal mean release rate of about 10 µg/hr and/or providing a mean AUCt of more than 14,000 pg·hr/ml, preferably of more than 16,000 pg·hr/ml, or of from more than 14,000 pg·hr/ml to about 32,000 pg·hr/ml, or of from more than 16,000 pg·hr/ml to about 32,000 pg·hr/ml over about 168 hours of administration after a single-dose administration to a subject population; and a third transdermal therapeutic system providing a size of the area of release ranging from about 6 cm² to about 18 cm² and containing an amount of said buprenorphine from about 6.5 mg to about 16 mg, or from about 6.5 mg to about 14 mg buprenorphine base or an equimolar amount of a pharmaceutically acceptable salt thereof and providing a nominal mean release rate of about 20 µg/hr and/or providing a mean AUCt of more than 28,000 pg·hr/ml, preferably of more than 32,000 pg·hr/ml, or of from more than 28,000 pg·hr/ml to about 64,000 pg·hr/ml, or of from more than 32,000 pg·hr/ml to about 64,000 pg·hr/ml over about 168 hours of administration after a single-dose administration to a subject population; and a fourth transdermal therapeutic system providing a size of the area of release ranging from about 12 cm² to about 27 cm² and containing an amount of said buprenorphine from about 11.5 mg to about 24 mg, or from about 11.5 mg to about 21 mg buprenorphine base or an equimolar amount of a pharmaceutically acceptable salt thereof and providing a nominal mean release rate of about 30 µg/hr and/or providing a mean AUCt of more than 42,000 pg·hr/ml, preferably of more than 48,000 pg·hr/ml, or of from more than 42,000 pg·hr/ml to about 96,000 pg·hr/ml, or of from more than 48,000 pg·hr/ml to about 96,000 pg·hr/ml over about 168 hours of administration after a single-dose administration to a subject population; and a fifth transdermal therapeutic system providing a size of the area of release ranging from about 16 cm² to about 35 cm² and containing an amount of said buprenorphine from about 15 mg to about 32 mg, or from about 15 mg to about 28 mg buprenorphine base or an equimolar amount of a pharmaceutically acceptable salt thereof and providing a nominal mean release rate of about 40 µg/hr and/or providing a mean AUCt of more than 62,000 pg·hr/ml, preferably of more than 64,000 pg·hr/ml, or of from more than 62,000 pg·hr/ml to about 128,000 pg·hr/ml, or of from more than 64,000 pg·hr/ml to about 128,000 pg·hr/ml over about 168 hours of administration after a single-dose administration to a subject population; and a further transdermal therapeutic system providing a size of the area of release ranging from about 5 cm² to about 13.5 cm² and containing an amount of said buprenorphine from about 5.5 mg to about 13 mg buprenorphine base or an equimolar amount of a pharmaceutically acceptable salt thereof and providing a nominal mean release rate of about 15 µg/hr and/or providing a mean AUCt of more than 22,000 pg·hr/ml, preferably of more than 24,000 pg·hr/ml, or of from more than 22,000 pg·hr/ml to about 48,000 pg·hr/ml, or of from more than 24,000 pg·hr/ml to about 48,000 pg·hr/ml over about 168 hours of administration after a single-dose administration to a subject population.

According to one aspect, the invention relates a transdermal therapeutic system comprising buprenorphine for the transdermal administration of buprenorphine selected from:
a first transdermal therapeutic system providing a size of the area of release ranging from about 2.5 cm² to about 4 cm² and containing an amount of said buprenorphine from 1 mg to about 3 mg buprenorphine base or an equimolar amount of a pharmaceutically acceptable salt thereof and providing a nominal mean release rate of about 5 μg/hr and/or providing a mean AUCt of more than 7,000 pg·hr/ml, preferably more than 8,000 pg·hr/ml, or of from more than 7,000 pg·hr/ml to about 16,000 pg·hr/ml, or of from more than 8,000 pg·hr/ml to about 16,000 pg·hr/ml over about 168 hours of administration after a single-dose administration to a subject population;

a second transdermal therapeutic system providing a size of the area of release ranging from about 5 cm² to about 8 cm² and containing an amount of said buprenorphine from about 3.5 mg to about 6 mg buprenorphine base or an equimolar amount of a pharmaceutically acceptable salt thereof and providing a nominal mean release rate of about 10 μg/hr and/or providing a mean AUCt of more than 14,000 pg·hr/ml, preferably of more than 16,000 pg·hr/ml, or of from more than 14,000 pg·hr/ml to about 32,000 pg·hr/ml, or of from more than 16,000 pg·hr/ml to about 32,000 pg·hr/ml over about 168 hours of administration after a single-dose administration to a subject population; and a third transdermal therapeutic system providing a size of the area of release ranging from about 10 cm² to about 16 cm² and containing an amount of said buprenorphine from about 6.5 mg to about 11 mg buprenorphine base or an equimolar amount of a pharmaceutically acceptable salt thereof and providing a nominal mean release rate of about 20 μg/hr and/or providing a mean AUCt of more than 28,000 pg·hr/ml, preferably of more than 32,000 pg·hr/ml, or of from more than 28,000 pg·hr/ml to about 64,000 pg·hr/ml, or of from more than 32,000 pg·hr/ml to about 64,000 pg·hr/ml over about 168 hours of administration after a single-dose administration to a subject population; and a fourth transdermal therapeutic system providing a size of the area of release ranging from about 17 cm² to about 23 cm² and containing an amount of said buprenorphine from about 11.5 mg to about 14 mg buprenorphine base or an equimolar amount of a pharmaceutically acceptable salt thereof and providing a nominal mean release rate of about 30 μg/hr and/or providing a mean AUCt of more than 42,000 pg·hr/ml, preferably of more than 48,000 pg·hr/ml, or of from more than 42,000 pg·hr/ml to about 96,000 pg·hr/ml, or of from more than 48,000 pg·hr/ml to about 96,000 pg·hr/ml over about 168 hours of administration after a single-dose administration to a subject population; and a fifth transdermal therapeutic system providing a size of the area of release ranging from about 23.5 cm² to about 32 cm² and containing an amount of said buprenorphine from about 15 mg to about 24 mg buprenorphine base or an equimolar amount of a pharmaceutically acceptable salt thereof and providing a nominal mean release rate of about 40 μg/hr and/or providing a mean AUCt of more than 62,000 pg·hr/ml, preferably of more than 64,000 pg·hr/ml, or of from more than 62,000 pg·hr/ml to about 128,000 pg·hr/ml, or of from more than 64,000 pg·hr/ml to about 128,000 pg·hr/ml over about 168 hours of administration after a single-dose administration to a subject population; and a further transdermal therapeutic system providing a size of the area of release ranging from about 5 cm² to about 13.5 cm² and containing an amount of said buprenorphine from about 5.5 mg to about 13 mg buprenorphine base or an equimolar amount of a pharmaceutically acceptable salt thereof and providing a nominal mean release rate of about 15 μg/hr and/or providing a mean AUCt of more than 22,000 pg·hr/ml, preferably of more than 24,000 pg·hr/ml, or of from more than 22,000 pg·hr/ml to about 48,000 pg·hr/ml, or of from more than 24,000 pg·hr/ml to about 48,000 pg·hr/ml over about 168 hours of administration after a single-dose administration to a subject population.

Release Characteristic

In accordance with the invention, the TTS is further characterized by the skin permeation rate determined by in vitro experiments carried out with the Franz diffusion cell (e.g., a 9 ml Franz diffusion cell), using human split thickness skin. Skin from cosmetic surgeries (female breast, date of birth 1989) can be used. A dermatone is used to prepare skin to a thickness of 800 μm, with an intact epidermis, in accordance with the OECD Guideline (adopted Apr. 13, 2004). Due to the prolonged test (168 hours) 800 μm skin is used instead of the recommended 200 to 400 μm skin. The receptor medium used is a phosphate buffer solution pH 5.5 with 0.1% saline azide as antibacteriological agent is used at a temperature of 32±1° Example formulations with an area of 1.163 cm² are punched from laminates, and in the present examples are each tested against 1.163 cm² samples of the commercial product Norspan®. The concentrations of buprenorphine in the acceptor medium of the Franz cell are measured.

The TTS according to the invention provides a mean cumulative skin permeation rate of more than about 1.3 μg/cm²-hr, or more than about 1.5 μg/cm²-hr or more than about 1.7 μg/cm²-hr over a 168 hours test, or of more than about 2 μg/cm²-hr over a 168 hours test, or of more than about 2.5 μg/cm²-hr over a 168 hours test, or of more than 2.7 μg/cm²-hr over a 168 hours test, or of more than about 3 μg/cm²-hr over a 168 hours test, or from about 1.3 μg/cm²-hr to about 4 μg/cm²-hr, or from about 1.7 μg/cm²-hr to about 4 μg/cm²-hr, or from about 2 μg/cm²-hr to about 4 μg/cm²-hr, or from about 2.5 μg/cm²-hr to about 4 μg/cm²-hr, or from about 2.7 μg/cm²-hr to about 4 μg/cm²-hr, or from about 3 μg/cm²-hr to about 4 μg/cm²-hr, over a 168 hours test. The commercial product BuTrans® provides a mean cumulative skin permeation rate of about 1.7 μg/cm²-hr over a 168 hours test in said test.

Figure 13:
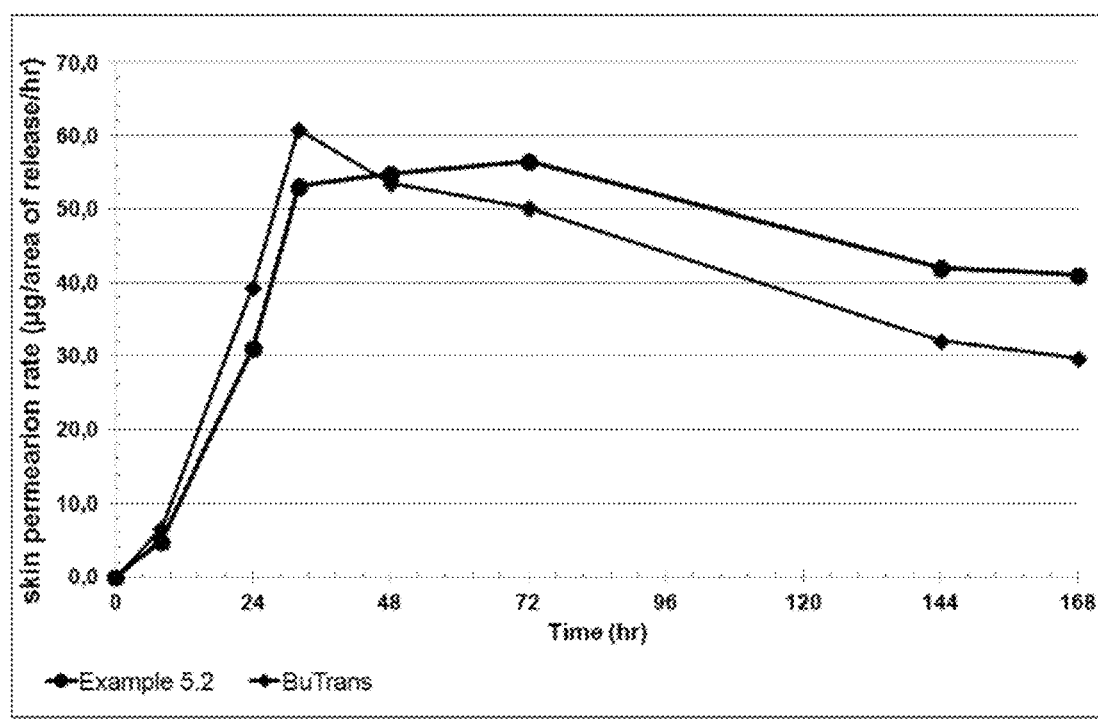
FIG. 13 depicts the mean non-cumulative skin permeation rate of the of the transdermal therapeutic systems. The area of release of the transdermal therapeutic system according to Example 5.2 is 14 cm² and the area of release for BuTrans® is 25 cm². The amount of buprenorphine base for Example 5.2 is 12.6 mg and the amount of buprenorphine base for BuTrans® is 20 mg.

According to certain embodiments, the TTS provides a cumulative release as measured in a Franz diffusion cell as mentioned above of about 220 μg/cm² to about 640 μg/cm² over a time period of 168 hours, or of about 400 μg/cm² to about 640 μg/cm², or of about 450 μg/cm² to about 640 μg/cm², or of about 500 μg/cm² to about 640 μg/cm², or of about 600 μg/cm² to about 640 μg/cm² over a time period of 168 hours. The commercial product BuTrans® provides a cumulative release of about 250.7 μg/cm² in said test. As can be seen from FIG. 13, comparable skin permeation rates are measured using the 25 cm² BuTrans® TTS including 20 mg buprenorphine base and a TTS of an example in accordance with the invention with an area of 14 cm² and including 12.6 mg buprenorphine base. This corresponds to about a 44% size reduction in area of release and a reduction of about 50% in the amount of used buprenorphine base.

According to certain embodiments, the TTS provides a non-cumulative release of buprenorphine base as measured in a Franz diffusion cell of
2 μg/cm² to 10 μg/cm² in the first 8 hours,
20 μg/cm² to 80 μg/cm² from hour 8 to hour 24,
20 μg/cm² to 80 μg/cm² from hour 24 to hour 32,
30 μg/cm² to 120 μg/cm² from hour 32 to hour 48,
40 μg/cm² to 150 μg/cm² from hour 48 to hour 72,
100 μg/cm² to 300 μg/cm² from hour 72 to hour 144, and
30 μg/cm2 to 100 μg/cm² from hour 144 to hour 168.

According to certain embodiments, the TTS provides a non-cumulative release of buprenorphine base as measured in a Franz diffusion cell of
2 µg/cm$^2$ to 6 µg/cm$^2$ in the first 8 hours,
25 µg/cm$^2$ to 60 µg/cm$^2$ from hour 8 to hour 24,
25 µg/cm$^2$ to 60 µg/cm$^2$ from hour 24 to hour 32,
40 µg/cm$^2$ to 100 µg/cm$^2$ from hour 32 to hour 48,
50 µg/cm$^2$ to 140 µg/cm$^2$ from hour 48 to hour 72,
100 µg/cm$^2$ to 280 µg/cm$^2$ from hour 72 to hour 144, and
30 µg/cm$^2$ to 100 µg/cm$^2$ from hour 144 to hour 168.

According to certain embodiments, the TTS provides a non-cumulative release of buprenorphine base as measured in a Franz diffusion cell of
3 µg/cm$^2$ to 6 µg/cm$^2$ in the first 8 hours,
30 µg/cm$^2$ to 50 µg/cm$^2$ from hour 8 to hour 24,
30 µg/cm$^2$ to 50 µg/cm$^2$ from hour 24 to hour 32,
60 µg/cm$^2$ to 90 µg/cm$^2$ from hour 32 to hour 48,
100 µg/cm$^2$ to 130 µg/cm$^2$ from hour 48 to hour 72,
200 µg/cm$^2$ to 280 µg/cm$^2$ from hour 72 to hour 144, and
60 µg/cm$^2$ to 100 µg/cm$^2$ from hour 144 to hour 168.

The commercial product BuTrans® provides a non-cumulative release of buprenorphine base as measured in a Franz diffusion cell in the same setting of
2.1 µg/cm$^2$ in the first 8 hours,
25.2 µg/cm$^2$ from hour 8 to hour 24,
19.4 µg/cm$^2$ from hour 24 to hour 32,
34.3 µg/cm$^2$ from hour 32 to hour 48,
48.2 µg/cm$^2$ from hour 48 to hour 72,
92.7 µg/cm$^2$ from hour 72 to hour 144, and
28.5 µg/cm$^2$ from hour 144 to hour 168.

Method of Treatment/Medical Use

According to one aspect, the transdermal therapeutic system in accordance with the invention and as described above in detail is for use in a method of treating pain. The Method comprises in particular the application of the TTS for about 168 hours (corresponding to 7 days or one week) on the skin of a patient. According to other methods in accordance with the invention the TTS can be applied for more than about 96 hours corresponding to more than 4 days, or about 120 hours corresponding to 5 days and about 144 hours corresponding to 6 days. The application for about 168 hours is preferred.

According to one aspect, the invention relates to a method of treatment wherein a set of five different transdermal therapeutic systems corresponding to different dosage strengths and corresponding different nominal mean release rates and/or mean release rates over about 168 hours of administration is used, wherein:
the first transdermal therapeutic system provides a size of said buprenorphine-containing pressure-sensitive adhesive layer providing the area of release ranging from about 1.5 cm$^2$ to about 5.5 cm$^2$ and contains an amount of said buprenorphine from about 1 mg to about 4.5 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 3 cm$^2$ to about 9 cm$^2$ and contains an amount of said buprenorphine from about 4 mg to about 9 mg buprenorphine base or an equimolar amount of a pharmaceutically acceptable salt thereof and provides a mean release rate of buprenorphine ranging from about 8 to about 12 µg/hr or from about 9 to about 1 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 6 cm$^2$ to about 14 cm$^2$ and contains an amount of said buprenorphine from about 8 mg to about 14 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/hr over about 168 hours of administration; and
the fourth transdermal therapeutic system provides a size of said buprenorphine-containing pressure-sensitive adhesive layer providing the area of release ranging from about 13 cm$^2$ to about 17 cm$^2$ and contains an amount of said buprenorphine from about 15 mg to about 20 mg buprenorphine base or an equimolar amount of a pharmaceutically acceptable salt thereof and provides a mean release rate of buprenorphine ranging from about 26 to about 35 µg/hr or from about 27 to about 32 µg/hr, and/or provides a nominal mean release rate of buprenorphine of about 30 µg/hr over about 168 hours of administration; and
the fifth transdermal therapeutic system provides a size of said buprenorphine-containing pressure-sensitive adhesive layer providing the area of release ranging from about 16 cm$^2$ to about 24 cm$^2$ and contains an amount of said buprenorphine from about 20 mg to about 28 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

The invention relates also to set of transdermal therapeutic systems, wherein:
the first transdermal therapeutic system provides a size of said buprenorphine-containing pressure-sensitive adhesive layer providing the area of release ranging from about 2 cm$^2$ to about 4 cm$^2$ and contains an amount of said buprenorphine from about 2 mg to about 4 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and
the second transdermal therapeutic system provides a size of said buprenorphine-containing pressure-sensitive adhesive layer providing the area of release ranging from about 4.5 cm$^2$ to about 7.5 cm$^2$ and contains an amount of said buprenorphine from about 5 mg to about 8 mg buprenorphine base or an equimolar amount of a pharmaceutically acceptable salt thereof and provides a mean release rate of buprenorphine ranging from about 8 to about 12 µg/hr or from about 9 to about 11 µg/hr, and/or provides a nominal mean release rate of buprenorphine of about 10 µg/hr over about 168 hours of administration; and
the third transdermal therapeutic system provides a size of said buprenorphine-containing pressure-sensitive adhesive layer providing the area of release ranging from about 8 cm$^2$ to about 12 cm$^2$ and contains an amount of said buprenorphine from about 10 mg to about 14 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/hr over about 168 hours of administration; and the fourth transdermal therapeutic system provides a size of said buprenorphine-containing pressure-sensitive adhesive layer providing the area of release ranging from about 13 cm² to about 16 cm² and contains an amount of said buprenorphine from about 16 mg to about 19 mg buprenorphine base or an equimolar amount of a pharmaceutically acceptable salt thereof and provides a mean release rate of buprenorphine ranging from about 26 to about 35 µg/hr or from about 27 to about 32 µg/hr, and/or provides a nominal mean release rate of buprenorphine of about 30 µg/hr over about 168 hours of administration; and the fifth transdermal therapeutic system provides a size of said buprenorphine-containing pressure-sensitive adhesive layer providing the area of release ranging from about 17 cm² to about 22 cm² and contains an amount of said buprenorphine from about 21 mg to about 26 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

The invention relates also to set of different transdermal therapeutic, wherein:

the first transdermal therapeutic system provides a size of said buprenorphine-containing pressure-sensitive adhesive layer providing the area of release ranging from about 2 cm² to about 3 cm² and contains an amount of said buprenorphine from about 2.5 mg to about 4 mg buprenorphine base or an equimolar amount of a pharmaceutically acceptable salt thereof and provides a mean release rate of buprenorphine ranging from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 4.5 cm² to about 6 cm² and contains an amount of said buprenorphine from about 5 mg to about 7 mg buprenorphine base or an equimolar amount of a pharmaceutically acceptable salt thereof and provides a mean release rate of buprenorphine ranging from about 8 to about 12 µg/hr or from about 9 to about 11 µg/hr, and/or provides a nominal mean release rate of buprenorphine of about 10 µg/hr over about 168 hours of administration; and the third transdermal therapeutic system provides a size of said buprenorphine-containing pressure-sensitive adhesive layer providing the area of release ranging from about 9 cm² to about 11 cm² and contains an amount of said buprenorphine from about 11 mg to about 13 mg buprenorphine base or an equimolar amount of a pharmaceutically acceptable salt thereof and provides a mean release rate of buprenorphine ranging from about 15 to about 25 µg/hr or from about 17 to about 22 µg/hr, and/or provides a nominal mean release rate of buprenorphine of about 20 µg/hr over about 168 hours of administration; and the fourth transdermal therapeutic system provides a size of said buprenorphine-containing pressure-sensitive adhesive layer providing the area of release ranging from about 14 cm² to about 16 cm² and contains an amount of said buprenorphine from about 17 mg to about 19 mg buprenorphine base or an equimolar amount of a pharmaceutically acceptable salt thereof and provides a mean release rate of buprenorphine ranging from about 26 to about 35 µg/hr or from about 27 to about 32 µg/hr, or about 30 µg/hr over about 168 hours of administration; and the fifth transdermal therapeutic system provides a size of said buprenorphine-containing pressure-sensitive adhesive layer providing the area of release ranging from about 18 cm² to about 21 cm² and contains an amount of said buprenorphine from about 22 mg to about 25 mg buprenorphine base or an equimolar amount of a pharmaceutically acceptable salt thereof and provides a mean release rate of buprenorphine ranging from about 36 to about 45 µg/hr or from about 38 to about 42 µg/hr, and/or provides a nominal mean release rate of buprenorphine of about 40 µg/hr over about 168 hours of administration.

According to one aspect, the invention relates to a method of treating pain in a patient wherein said patient is treated with one appropriately selected TTS from a set of two (first and second, or second and third, or third and fourth, or fourth and fifth TTS, or any other combination of two of the five different dosage strengths), three (first to third, or second to fourth or third to fifth TTS, or any other combination of three of the five different dosage strengths), four (first to fourth or second to fifth TTS, or any other combination of four of the five different dosage strengths) or five (first to fifth TTS) different transdermal therapeutic systems corresponding to different dosage strengths and corresponding different nominal mean release rates and/or mean release rates over about 168 hours of administration is used, wherein:

the first transdermal therapeutic system provides a size of said buprenorphine-containing pressure-sensitive adhesive layer providing the area of release ranging from about 1 cm² to about 4.8 cm² and contains an amount of said buprenorphine from about 1 mg to about 4 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 3 cm² to about 9.5 cm² and contains an amount of said buprenorphine from about 3.5 mg to about 8 mg buprenorphine base or an equimolar amount of a pharmaceutically acceptable salt thereof and provides a mean release rate of buprenorphine of at least about 6 µg/hr, or of from about 8 to about 12 µg/hr or from about 9 to about 11 µg/hr, and/or provides a nominal mean release rate of buprenorphine of about 10 µg/hr over about 168 hours of administration; and the third transdermal therapeutic system provides a size of said buprenorphine-containing pressure-sensitive adhesive layer providing the area of release ranging from about 6 cm² to about 19 cm² and contains an amount of said buprenorphine from about 6.5 mg to about 16 mg buprenorphine base or an equimolar amount of a pharmaceutically acceptable salt thereof and provides a mean release rate of buprenorphine of at least about 11 µg/hr, or of from about 15 to about 25 µg/hr or at least about 16 µg/hr, or from about 17 to about 22 µg/hr, and/or provides a nominal mean release rate of buprenorphine of about 20 µg/hr over about 168 hours of administration; and the fourth transdermal therapeutic system provides a size of said buprenorphine-containing pressure-sensitive adhesive layer providing the area of release ranging from about 12 cm² to about 28.5 cm² and contains an amount of said buprenorphine from about 11.5 mg to about 24 mg buprenorphine base or an equimolar amount of a pharmaceutically acceptable salt thereof and provides a mean release rate of buprenorphine of at least about 21 µg/hr, or of from about 26 to about 35 µg/hr or from about 27 to about 32 µg/hr, and/or provides a nominal mean release rate of buprenorphine of about 30 µg/hr over about 168 hours of administration; and the fifth transdermal therapeutic system provides a size of said buprenorphine-containing pressure-sensitive adhesive layer providing the area of release ranging from about 16 cm² to about 38 cm² and contains an amount of said buprenorphine from about 15 mg to about 32 mg buprenorphine base or an equimolar amount of a pharmaceutically acceptable salt thereof and provides a mean release rate of buprenorphine of at least about 31 µg/hr, or of from about 36 to about 45 µg/hr or from about 38 to about 42 µg/hr, and/or provides a nominal mean release rate of buprenorphine of about 40 µg/hr over about 168 hours of administration. The set of two to five different transdermal therapeutic systems in accordance with this paragraph can be expanded by a further transdermal therapeutic system which provides a size of said buprenorphine-containing pressure-sensitive adhesive layer providing the area of release ranging from about 5 cm² to about 14 cm² and contains an amount of said buprenorphine from about 5.5 mg to about 13 mg buprenorphine base or an equimolar amount of a pharmaceutically acceptable salt thereof and provides a mean release rate of buprenorphine of at least about 11 µg/hr, or of from about 12 to about 18 µg/hr or from about 13.5 to about 16.5 µg/hr, and/or provides a nominal mean release rate of buprenorphine of about 15 µg/hr over about 168 hours of administration. Alternatively, one of the transdermal therapeutic systems of the set of two to five different transdermal therapeutic systems can be replaced by said transdermal therapeutic system.

The invention relates also to a set of transdermal therapeutic systems, wherein:

the first transdermal therapeutic system provides a size of said buprenorphine-containing pressure-sensitive adhesive layer providing the area of release ranging from about 1 cm² to about 4.5 cm² and contains an amount of said buprenorphine from about 1 mg to about 4 mg, or from about 1 mg to about 3.5 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 3 cm² to about 9 cm² and contains an amount of said buprenorphine from about 3.5 mg to about 8 mg, or from about 3.5 mg to about 7 mg buprenorphine base or an equimolar amount of a pharmaceutically acceptable salt thereof and provides a mean release rate of buprenorphine of at least about 6 µg/hr, or of from about 8 to about 12 µg/hr or from about 9 to about 11 µg/hr, and/or provides a nominal mean release rate of buprenorphine of about 10 µg/hr over about 168 hours of administration; and the third transdermal therapeutic system provides a size of said buprenorphine-containing pressure-sensitive adhesive layer providing the area of release ranging from about 6 cm² to about 18 cm² and contains an amount of said buprenorphine from about 6.5 mg to about 16 mg, or from about 6.5 mg to about 14 mg buprenorphine base or an equimolar amount of a pharmaceutically acceptable salt thereof and provides a mean release rate of buprenorphine of at least about 11 µg/hr, or of from about 15 to about 25 µg/hr or at least about 16 µg/hr, from about 17 to about 22 µg/hr, and/or provides a nominal mean release rate of buprenorphine of about 20 µg/hr over about 168 hours of administration; and the fourth transdermal therapeutic system provides a size of said buprenorphine-containing pressure-sensitive adhesive layer providing the area of release ranging from about 12 cm² to about 27 cm² and contains an amount of said buprenorphine from about 11.5 mg to about 24 mg, or from about 11.5 mg to about 21 mg buprenorphine base or an equimolar amount of a pharmaceutically acceptable salt thereof and provides a mean release rate of buprenorphine of at least about 21 µg/hr, or of from about 26 to about 35 µg/hr or from about 27 to about 32 µg/hr, and/or provides a nominal mean release rate of buprenorphine of about 30 µg/hr over about 168 hours of administration; and the fifth transdermal therapeutic system provides a size of said buprenorphine-containing pressure-sensitive adhesive layer providing the area of release ranging from about 16 cm² to about 35 cm² and contains an amount of said buprenorphine from about 15 mg to about 32 mg, or from about 15 mg to about 28 mg buprenorphine base or an equimolar amount of a pharmaceutically acceptable salt thereof and provides a mean release rate of buprenorphine of at least about 31 µg/hr, or of from about 36 to about 45 µg/hr or from about 38 to about 42 µg/hr, and/or provides a nominal mean release rate of buprenorphine of about 40 µg/hr over about 168 hours of administration. The set of two to five different transdermal therapeutic systems in accordance with this paragraph can be expanded by a further transdermal therapeutic system which provides a size of said buprenorphine-containing pressure-sensitive adhesive layer providing the area of release ranging from about 5 cm² to about 13.5 cm² and contains an amount of said buprenorphine from about 5.5 mg to about 13 mg buprenorphine base or an equimolar amount of a pharmaceutically acceptable salt thereof and provides a mean release rate of buprenorphine of at least about 11 µg/hr, or of from about 12 to about 18 µg/hr or from about 13.5 to about 16.5 µg/hr, and/or provides a nominal mean release rate of buprenorphine of about 15 µg/hr over about 168 hours of administration. Alternatively, one of the transdermal therapeutic systems of the set of two to five different transdermal therapeutic systems can be replaced by said transdermal therapeutic system. Alternatively, one of the transdermal therapeutic systems of the set of two to five different transdermal therapeutic systems can be replaced by said transdermal therapeutic system.

The invention relates also to set of different transdermal therapeutic, wherein:

the first transdermal therapeutic system provides a size of said buprenorphine-containing pressure-sensitive adhesive layer providing the area of release ranging from about 2.5 cm² to about 4 cm² and contains an amount of said buprenorphine from about 1 mg to about 3 mg buprenorphine base or an equimolar amount of a pharmaceutically acceptable salt thereof and provides a mean release rate of buprenorphine of at least about 2 µg/hr, or of from about 2.5 to about 7.5 µg/hr or from about 4 to about 6 µg/hr, and/or provides a nominal mean release rate of buprenorphine of about 5 µg/hr over about 168 hours of administration; and the second transdermal therapeutic system provides a size of said buprenorphine-containing pressure-sensitive adhesive layer providing the area of release ranging from about 5 cm$^2$ to about 8 cm$^2$ and contains an amount of said buprenorphine from about 3.5 mg to about 6 mg buprenorphine base or an equimolar amount of a pharmaceutically acceptable salt thereof and provides a mean release rate of buprenorphine of at least about 6 μg/hr, or of from about 8 to about 12 μg/hr or from about 9 to about 11 μg/hr, and/or provides a nominal mean release rate of buprenorphine of about 10 μg/hr over about 168 hours of administration; and the third transdermal therapeutic system provides a size of said buprenorphine-containing pressure-sensitive adhesive layer providing the area of release ranging from about 10 cm$^2$ to about 16 cm$^2$ and contains an amount of said buprenorphine from about 6.5 mg to about 11 mg buprenorphine base or an equimolar amount of a pharmaceutically acceptable salt thereof and provides a mean release rate of buprenorphine of at least about 11 μg/hr, or of from about 15 to about 25 μg/hr or from about 17 to about 22 μg/hr, and/or provides a nominal mean release rate of buprenorphine of about 20 μg/hr over about 168 hours of administration; and the fourth transdermal therapeutic system provides a size of said buprenorphine-containing pressure-sensitive adhesive layer providing the area of release ranging from about 17 cm$^2$ to about 23 cm$^2$ and contains an amount of said buprenorphine from about 11.5 mg to about 14 mg buprenorphine base or an equimolar amount of a pharmaceutically acceptable salt thereof and provides a mean release rate of buprenorphine of at least about 21 μg/hr, or of from about 26 to about 35 μg/hr or from about 27 to about 32 μg/hr, and/or provides a nominal mean release rate of buprenorphine of about 30 μg/hr over about 168 hours of administration; and the fifth transdermal therapeutic system provides a size of said buprenorphine-containing pressure-sensitive adhesive layer providing the area of release ranging from about 23.5 cm$^2$ to about 32 cm$^2$ and contains an amount of said buprenorphine from about 15 mg to about 24 mg buprenorphine base or an equimolar amount of a pharmaceutically acceptable salt thereof and provides a mean release rate of buprenorphine of at least about 31 μg/hr, or of from about 36 to about 45 μg/hr or from about 38 to about 42 μg/hr, and/or provides a nominal mean release rate of buprenorphine of about 40 μg/hr over about 168 hours of administration.

According to one aspect, the invention relates to a method of treating pain in a patient wherein a patient is treated with one appropriately selected TTS from a set of different transdermal therapeutic systems as described in the previous paragraphs, wherein:

the first transdermal therapeutic system provides a mean AUCt of more than 7,000 pg·hr/ml, preferably more than 8,000 pg·hr/ml, or of from more than 7,000 pg·hr/ml to about 16,000 pg·hr/ml, or of from more than 8,000 pg·hr/ml to about 16,000 pg·hr/ml over about 168 hours of administration after a single-dose administration to a subject population; and the second transdermal therapeutic system provides a mean AUCt of more than 14,000 pg·hr/ml, preferably of more than 16,000 pg·hr/ml, or of from more than 14,000 pg·hr/ml to about 32,000 pg·hr/ml, or of from more than 16,000 pg·hr/ml to about 32,000 pg·hr/ml over about 168 hours of administration after a single-dose administration to a subject population; and the third transdermal therapeutic system provides a mean AUCt of more than 28,000 pg·hr/ml, preferably of more than 32,000 pg·hr/ml, or of from more than 28,000 pg·hr/ml to about 64,000 pg·hr/ml, or of from more than 32,000 pg·hr/ml to about 64,000 pg·hr/ml over about 168 hours of administration after a single-dose administration to a subject population; and the fourth transdermal therapeutic system provides a mean AUCt of more than 42,000 pg·hr/ml, preferably of more than 48,000 pg·hr/ml, or of from more than 42,000 pg·hr/ml to about 96,000 pg·hr/ml, or of from more than 48,000 pg·hr/ml to about 96,000 pg·hr/ml over about 168 hours of administration after a single-dose administration to a subject population; and the fifth transdermal therapeutic system provides a mean AUCt of more than 62,000 pg·hr/ml, preferably of more than 64,000 pg·hr/ml, or of from more than 62,000 pg·hr/ml to about 128,000 pg·hr/ml, or of from more than 64,000 pg·hr/ml to about 128,000 pg·hr/ml over about 168 hours of administration after a single-dose administration to a subject population; and the further transdermal therapeutic system provides a mean AUCt of more than 22,000 pg·hr/ml, preferably of more than 24,000 pg·hr/ml, or of from more than 22,000 pg·hr/ml to about 48,000 pg·hr/ml, or of from more than 24,000 pg·hr/ml to about 48,000 pg·hr/ml over about 168 hours of administration after a single-dose administration to a subject population.

According to one aspect, the invention relates to a method of treatment described in the previous paragraphs, wherein the transdermal therapeutic system provides a mean AUCt per area of release of more than 1,700 pg·hr/ml-cm$^2$, or of more than 1,900 pg·hr/ml-cm$^2$, or of more than 2,300 pg·hr/ml-cm$^2$ over about 168 hours of administration after a single-dose administration to a subject population or provides a mean AUCt per area of release of from more than 1,700 pg·hr/ml-cm$^2$ to about 5,000 pg·hr/ml-cm$^2$, or of from more than 1,900 pg·hr/ml-cm$^2$ to about 5,000 pg·hr/ml-cm$^2$, or of from more than 2,300 pg·hr/ml-cm$^2$ to about 5,000 pg·hr/ml-cm$^2$ over about 168 hours of administration after a single-dose administration to a subject population.

According to one aspect, the invention relates to a method of treatment described in the previous paragraphs, wherein the transdermal therapeutic system provides an arithmetic mean t max of from about 60 hr to about 120 hr, preferably from about 66 hr to less than 108 hr, or from about 72 hr to about 96 hr after a single-dose administration to a subject population.

Method of Manufacture

According to one further aspect, the invention relates to a method of manufacture of a transdermal therapeutic system for the transdermal administration of buprenorphine, comprising the steps of 1. providing a buprenorphine-containing adhesive mixture comprising
   a) buprenorphine base or a pharmaceutically acceptable salt thereof
   b) a carboxylic acid (e.g., levulinic acid),
   c) a viscosity increasing agent (e.g. polyvinylpyrrolidon)
   c) a polymer-based pressure-sensitive adhesive, and
   d) solvent (e.g., heptane and ethanol)
2. storing said mixture between 0 hours and 6 days
3. homogenizing said buprenorphine-containing adhesive mixture at a homogenizing speed of e.g. at least 1000 rpm (e.g. with a BECOMIX RW 30 Ex);
4. storing said homogenized mixture between 0 hours and 6 days,
5. coating said homogenized buprenorphine-containing adhesive mixture on a film (e.g., polyethylene terephthalate film) in an amount to provide the desired dry weight using a roller coater in an amount to provide the desired coating dry weight, 6. drying said coated buprenorphine-containing adhesive mixture to provide a buprenorphine-containing adhesive layer with the desired coating dry weight, 7. optionally laminating said buprenorphine-containing adhesive layer to a backing layer (e.g., Scotchpak 1220 from 3M) to provide an buprenorphine-containing self-adhesive layer structure, 8. optionally punching the individual systems from the buprenorphine-containing self-adhesive layer structure with the desired area of release, and 9. optionally adhering to the individual systems an active-free self-adhesive layer structure comprising also a backing layer and an active agent-free pressure-sensitive adhesive layer and which is larger than the individual systems of buprenorphine-containing self-adhesive layer structure.

In step 1 of said method of manufacture preferably buprenorphine base, levulinic acid and polyvinylpyrrolidone are used and are dissolved in ethanol and subsequently suspended in a polymer-based pressure-sensitive adhesive based on polysiloxane in heptane to provide the buprenorphine-containing adhesive mixture or emulsion.

The homogenization provides homogeneous mixtures and helps to provide narrower deposit size distributions. In combination with a viscosity-increasing substance in the deposits the size and size distribution of the deposits remains during the time between homogenization and coating and during coating. In particular the process is suitable for a commercial production skale.

Homogenization speeds of e.g. at least 1000 rpm can be applied with a homogenizer, e.g. with a rotor-stator homogenizer (e.g. BECOMIX RW 30 Ex). In certain embodiments of the invention the homogenization speed is from about 1500 rpm to about 3800 rpm, or from about 1500 rpm to about 3000 rpm. The preferred homogenization speed is about 2000 rpm.

EXAMPLES

The present invention will now be more fully described with reference to the accompanying examples. It should be understood, however, that the following description is illustrative only and should not be taken in any way as a restriction of the invention.

Comparative Example 1

The composition of the buprenorphine base-containing adhesive mixture is summarized in Table 1 below.

TABLE 1

| Ingredient (Trade Name) | Amt/unit (g) |
| --- | --- |
| Buprenorphine base | 7.00 |
| Levulinic acid | 4.90 |
| Ascorbyl palmitate | 0.175 |
| Ethanol | 3.80 |
| Polysiloxane adhesive in n-heptane Solids content of 73% by weight (BIO-PSA 7-4201 from Dow Corning Healthcare) | 79.57 |
| n-heptane | 4.56 |
| Total | 100.01 |

In a suitable vessel, 7.00 g of buprenorphine were dissolved in 4.90 g of levulinic acid, 3.80 g of Ethanol and 0.175 g of Ascobyl palmitate by stirring until the buprenorphine was completely dissolved forming the buprenorphine solution. 79.57 g of a polysiloxane adhesive in the form of a solution in n-heptane having a solids content of 73% by weight and 4.56 g of heptane were added. The mixture was stirred to give 100.01 g of a buprenorphine-containing adhesive mixture with 7% of buprenorphine, with a solids content of 70% (buprenorphine base-containing adhesive mixture).

The buprenorphine base-containing adhesive mixture was coated within less than 24 h after the buprenorphine containing mixture was finished on a polyethylene terephthalate film (e.g. Scotchpak from 3M) using an Erichsen coater and the solvent was removed by drying at approximately 50° C. for approx. 8 minutes.

The coating thickness was chosen such that removal of the solvents results in a coating weight of the matrix layer of approx. 120 g/m$^2$. This results in the 10% by weight of buprenorphine base, and 7% by weight of levulinic acid in this matrix layer. The dried film was laminated with the backing layer (e.g. polyethylenterephthalate (PET) foil 19 μm) to provide the buprenorphine-containing self-adhesive layer structure.

Microscopic pictures were taken of the matrix layer using a Nikon S/N 237789 Microscope. FIG. 1 shows a microscopic picture of the matrix layer of Example 1.

Comparative Example 2

The composition of the buprenorphine base-containing adhesive mixture is summarized in Table 2 below.

TABLE 2

| Ingredient (Trade Name) | Amt/unit (kg) |
| --- | --- |
| Buprenorphine base | 1.890 |
| Levulinic acid | 1.323 |
| Ethanol | 0.945 |
| Polysiloxane adhesive in n-heptane Solids content of 73% by weight (BIO-PSA 7-4201 from Dow Corning Healthcare) | 21.489 |
| n-heptane | 1.353 |
| Total | 27 |

In a stainless steel vessel, 1.890 kg of buprenorphine were dissolved in 1.323 kg of levulinic acid and 0.945 kg of ethanol by stirring until the buprenorphine was completely dissolved. With stirring, 21.489 kg of a polysiloxane adhesive in the form of a solution in n-heptane having a solids content of 73% by weight and 1.353 kg of heptane were added. The mixture was stirred to give 27 kg of a buprenorphine-containing adhesive mixture with 7% of buprenorphine, with a solids content of 70% (buprenorphine base-containing adhesive mixture).

Within 24 hours the buprenorphine base-containing adhesive mixture was coated on a polyethylene terephthalate film (e.g., Scotchpak from 3M) using a pilot plant roll coater including a drying tunnel, several drying sections, an unwinding and laminating station. The solvent was removed by drying at approximately 30-50° C. The matrix layer remained within the drying tunnel at approx. 8 minutes. The coating thickness was chosen such that removal of the solvents results in a coating weight of the matrix layer of 120 g/m$^2$. This results in the 10% by weight of buprenorphine base and 7% by weight of levulinic acid in this matrix layer. The dried film was laminated with the backing layer (e.g: polyethylenterephthalate (PET) film 19 μm) to provide the buprenorphine-containing self-adhesive layer structure.

The individual systems (TTS) were then punched from the buprenorphine-containing self-adhesive layer structure.

In specific embodiments a TTS as described above can be provided with a further self-adhesive layer of larger surface area, preferably with rounded corners, comprising a pressure-sensitive adhesive matrix layer which is free of active ingredient and has a preferably beige colored backing layer (overtape). This is of advantage when the TTS, on the basis of its physical properties alone, does not adhere sufficiently to the skin and/or when the buprenorphine-containing matrix layer, for the purpose of avoiding waste, has pronounced corners (square or rectangular shapes). The overtape including the TTS are then punched out by only punching the overtape and sealed into pouches of the primary packaging material.

Figure 2A:
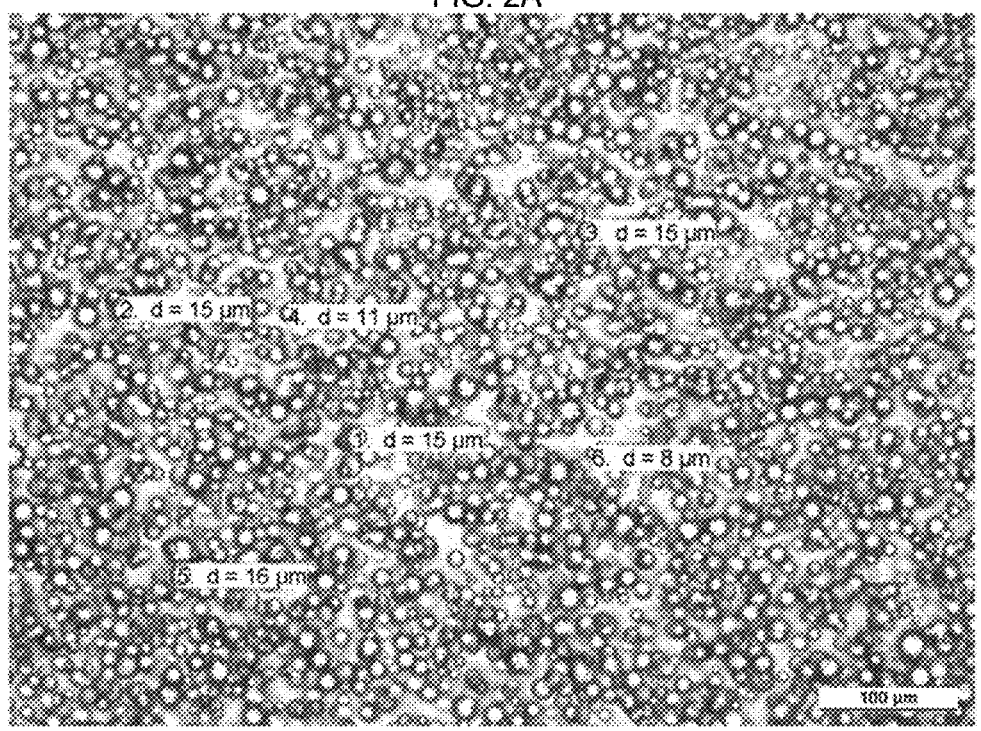
FIG. 2A depicts a microscopic picture of the buprenorphine base-containing adhesive mixture of Comparative Example 2.
Figure 2B:
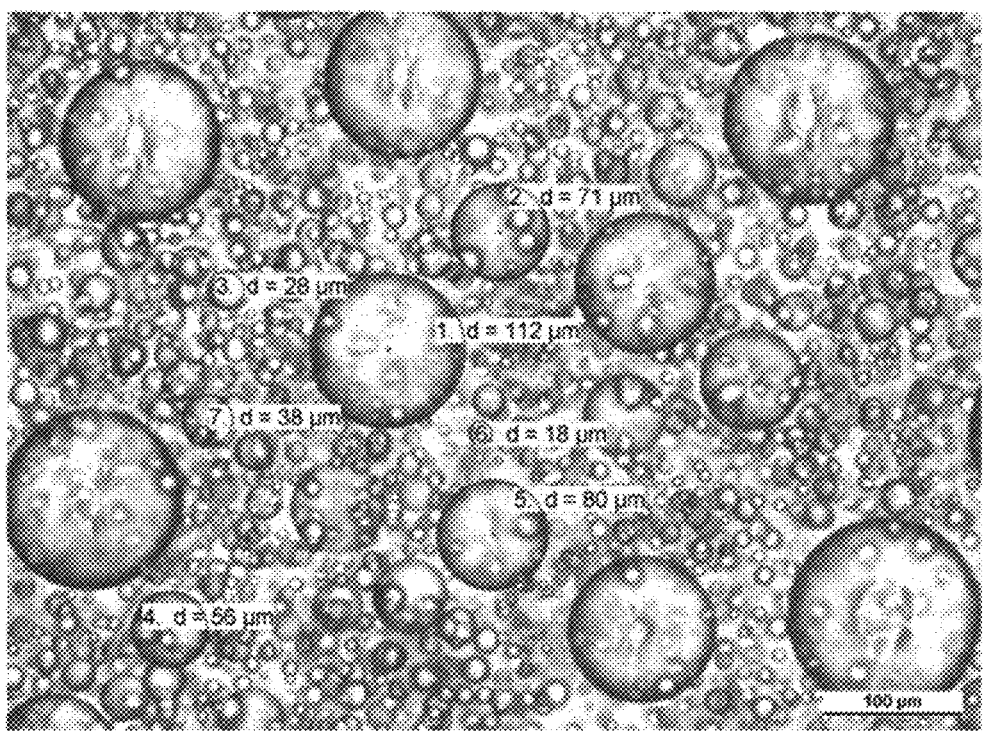
FIG. 2B depicts a microscopic picture of the matrix layer of Comparative Example 2.

Microscopic pictures were taken of the buprenorphine base-containing adhesive mixture and of the matrix layer using a Nikon S/N 237789 Microscope. FIG. 2A shows a microscopic picture of the buprenorphine base-containing adhesive mixture of Comparative Example 2 and FIG. 2B shows a microscopic picture of the matrix layer of Comparative Example 2.

Example 3

The composition of the buprenorphine base-containing adhesive mixture is summarized in Table 3 below.

TABLE 3

| Ingredient (Trade Name) | Amt/unit (g) |
|---|---|
| Buprenorphine base | 7.44 |
| Levulinic acid | 5.24 |
| Ascorbyl palmitate | 0.14 |
| Polyvinylpyrrolidone (PVP) | 1.88 |
| Ethanol | 10.77 |
| Polysiloxane adhesive in n-heptane Solids content of 73% by weight (BIO-PSA 7-4201 from Dow Corning Healthcare) | 82.47 |
| n-heptane | 1.73 |
| Total | 109.67 |

In a suitable vessel, 37.86 g of polyvinylpyrrolidone and 113.57 g of ethanol were dissolved to form a 25% PVP pre-solution. The prescribed amount of the PVP pre-solution, Levulinic acid and Ascorbyl palmitate were suspended with stirring and afterwards the remaining part of Ethanol and the Buprenorphine was added to form a buprenorphine containing solution by stirring until a solution is formed. 82.50 g of a polysiloxane adhesive in the form of a solution in n-heptane having a solids content of 73% by weight and 1.74 g of heptane were added. The mixture was stirred to give 109.67 g of a buprenorphine-containing adhesive mixture with 6.8% of buprenorphine, with a solids content of 68% (buprenorphine base-containing adhesive mixture).

The buprenorphine base-containing adhesive mixture was coated within less than 24 h after the buprenorphine containing mixture was finished on a polyethylene terephthalate film (e.g. Scotchpak from 3M) using an Erichsen coater and the solvent was removed by drying in a first step at room temperature for approximately 10 minutes, followed by a second drying step at approximately 60° C. for approx. 10 minutes.

The coating thickness was chosen such that removal of the solvents results in a coating weight of the matrix layer of approx. 120 g/m². This results in the 10% by weight of buprenorphine base, 7% by weight of levulinic acid and 2.5% by weight of polyvinylpyrrolidone in this matrix layer. The dried film was laminated with the backing layer (e.g. polyethylenterephthalate (PET) foil 19 μm) to provide the buprenorphine-containing self-adhesive layer structure.

Figure 3A:
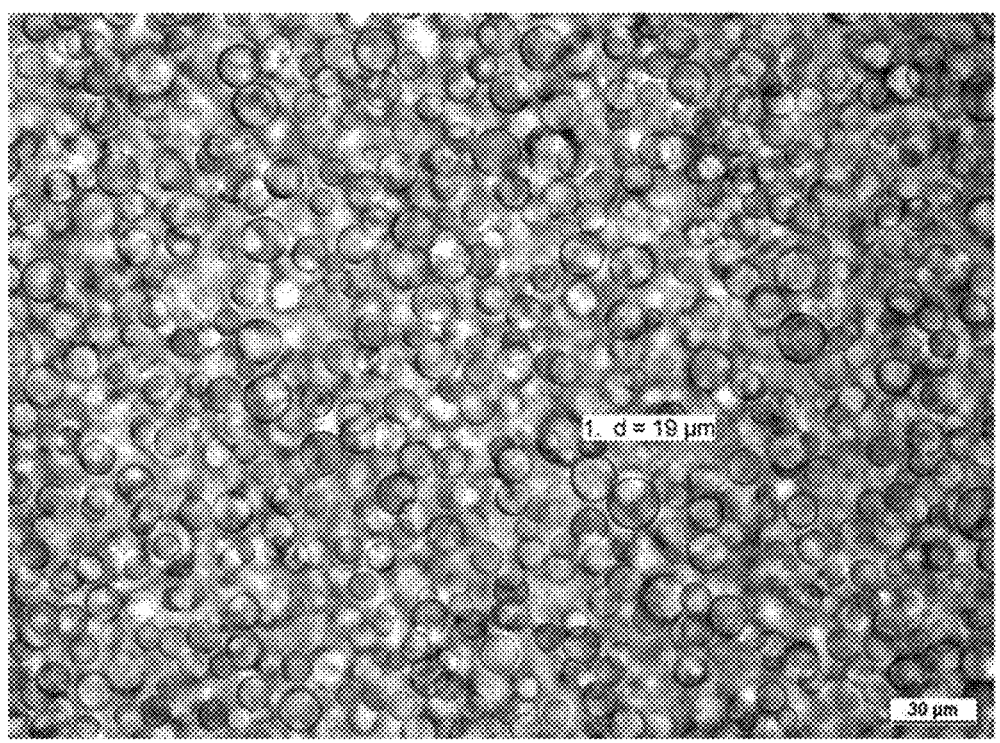
FIG. 3A depicts a microscopic picture of the buprenorphine base-containing adhesive mixture of Example 3.
Figure 3B:
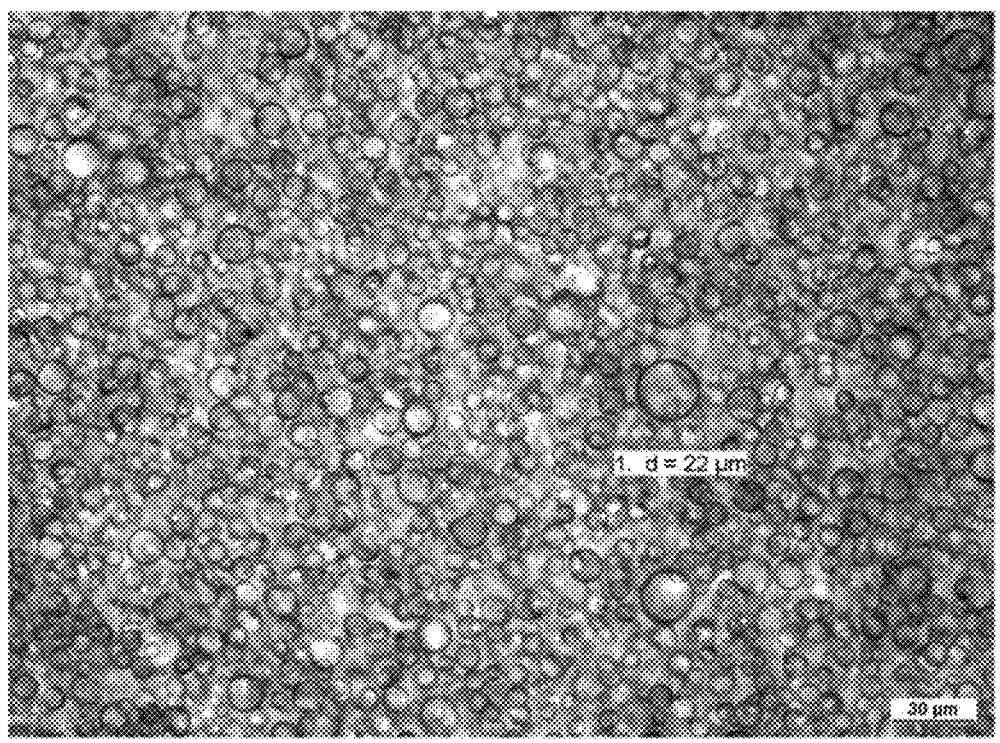
FIG. 3B depicts a microscopic picture of the matrix layer of Example 3.

Microscopic pictures were taken of the buprenorphine base-containing adhesive mixture and the matrix layer using a Nikon S/N 237789 Microscope. FIG. 3 shows a microscopic picture of the matrix layer of Example 3. FIG. 3A shows a microscopic picture of the buprenorphine base-containing adhesive mixture of Example 3 and FIG. 3B shows a microscopic picture of the matrix layer of Example 3.

Example 4

The composition of the buprenorphine base-containing adhesive mixture is summarized in Table 4 below.

TABLE 4

| Ingredient (Trade Name) | Amt/unit (kg) |
|---|---|
| Buprenorphine base | 1.368 |
| Levulinic acid | 0.958 |
| Polyvinylpyrrolidone (PVP) | 0.342 |
| Ascorbyl palmitate | 0.027 |
| Ethanol | 1.938 |
| Polysiloxane adhesive in n-heptane Solids content of 73% by weight (BIO-PSA 7-4201 from Dow Corning Healthcare) | 15.048 |
| n-heptane | 0.319 |
| Total | 20 |

In a 10 l vessel, 1.00 kg of polyvinylpyrrolidone and 3.00 g of ethanol were dissolved to form a 25% PVP pre-solution. In a homogenizing/mixing vessel: Becomix Lab mixer RW 30 Ex, 1.368 kg of PVP pre-solution, 0.958 kg levulinic acid, 0.027 kg of Ascorbyl palmitate and the main part of 0.912 kg of Ethanol were suspended by stirring. The prescribed amount of buprenorphine was weighed and added to the homogenizing/mixing vessel followed by rinsing the weighing container used for buprenorphine with the remaining part of Ethanol. The mixture was kept under stirring for at least 1 h until a buprenorphine containing solution was formed. 15.048 kg of a polysiloxane adhesive in the form of a solution in n-heptane having a solids content of 73% by weight and 0.319 kg of n-heptane were added to the mixing/homogenizing vessel The mixture was stirred for at least 2 h until a buprenorphine-containing adhesive mixture with 6.8% of buprenorphine, with a solids content of 68% (buprenorphine base-containing adhesive mixture) was formed.

Within 24 hours the buprenorphine base-containing adhesive mixture was coated on a polyethylene terephthalate foil (e.g. Scotchpak from 3M) using a pilot plant roll coater including a drying tunnel, several drying sections, an unwinding and laminating station. The solvent was removed by drying at approximately 30-50° C. The matrix layer remained within the drying tunnel at approx. 8 minutes. The coating thickness was chosen such that removal of the solvents results in a coating weight of the matrix layer of 120 g/m². This results in the 10% by weight of buprenorphine base and 7% by weight of levulinic acid and 2.5% by weight of polyvinylpyrrolidone in this matrix layer. The dried film was laminated with the backing layer (e.g. polyethylenterephthalate (PET) foil 19 μm) to provide the buprenorphine-containing self-adhesive layer structure.

The individual systems (TTS) were then punched from the buprenorphine-containing self-adhesive layer structure.

In specific embodiments a TTS as described above can be provided with a further self-adhesive layer of larger surface area, preferably with rounded corners, comprising a pressure-sensitive adhesive matrix layer which is free of active ingredient and has a preferably beige colored backing layer (overtape). This is of advantage when the TTS, on the basis of its physical properties alone, does not adhere sufficiently to the skin and/or when the buprenorphine-containing matrix layer, for the purpose of avoiding waste, has pronounced corners (square or rectangular shapes.

The overtape including the TTS are then punched out by only punching the overtape and sealed into pouches of the primary packaging material.

Figure 4A:
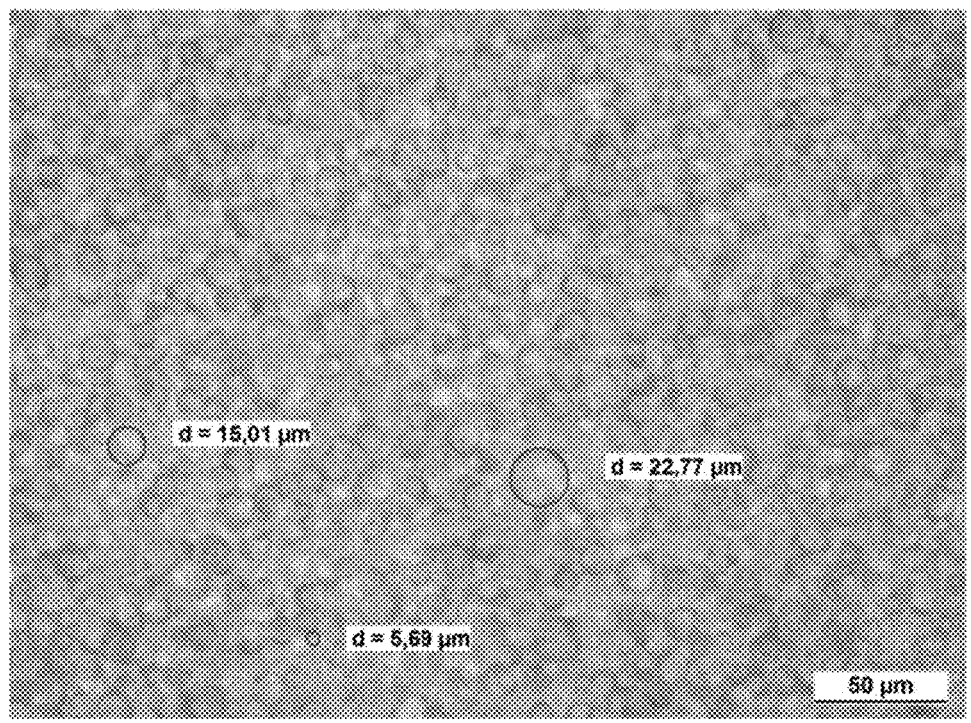
FIG. 4A depicts a microscopic picture of the buprenorphine base-containing adhesive mixture of Example 4.
Figure 4B:
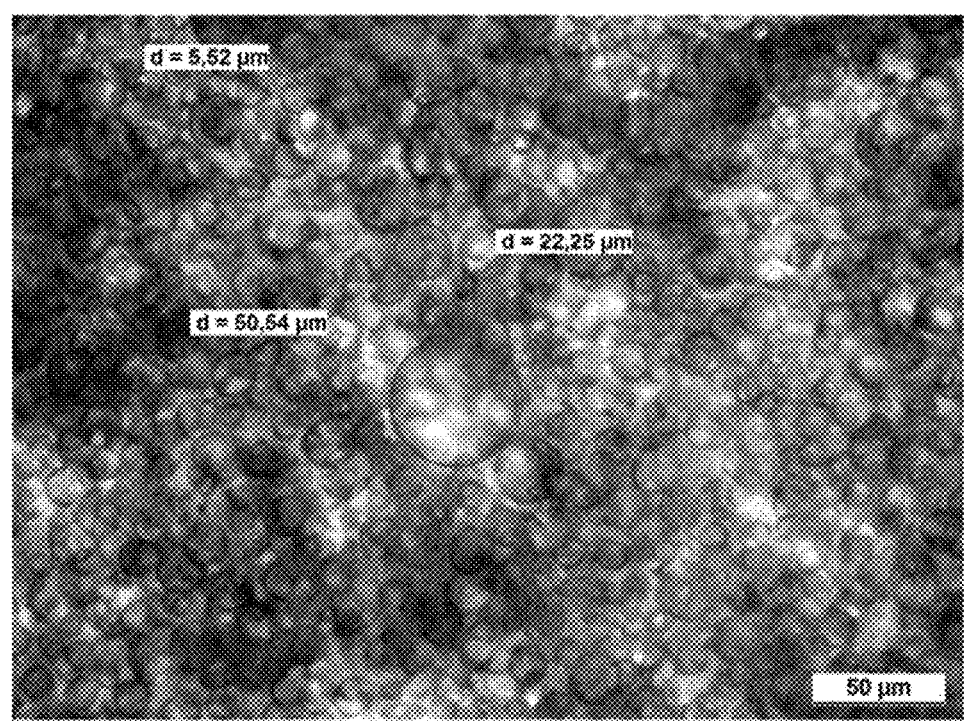
FIG. 4B depicts a microscopic picture of the matrix layer of Example 4.
Figure 5:
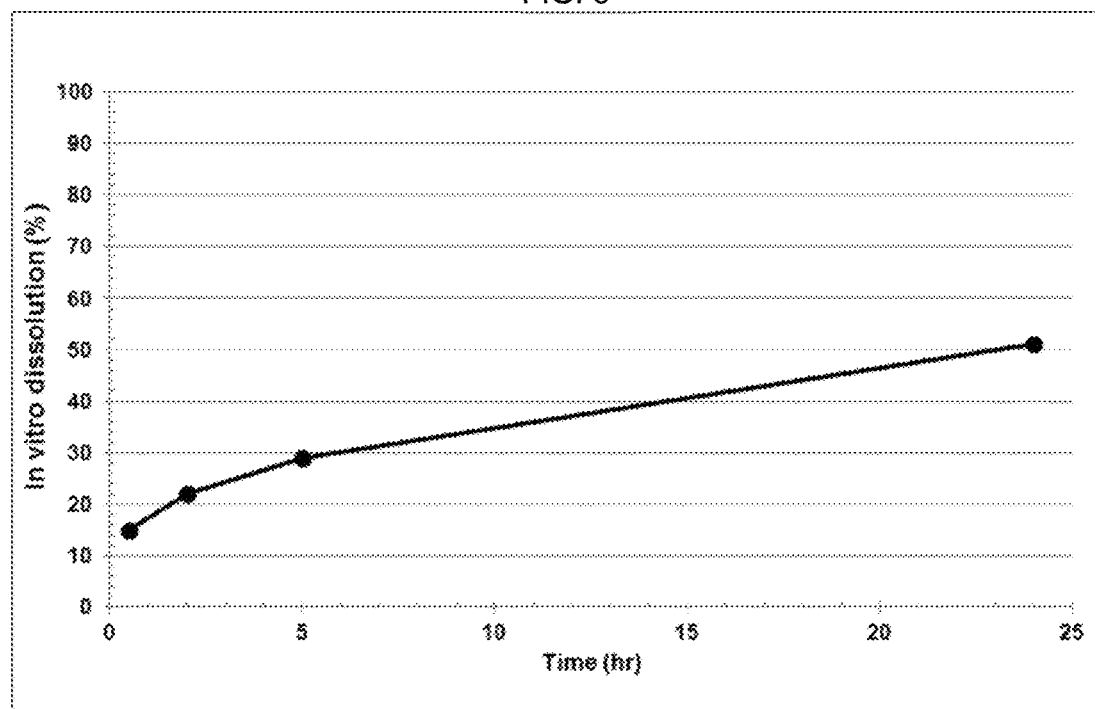
FIG. 5 depicts the mean in-vitro-dissolution of Comparative Example 1.
Figure 6:
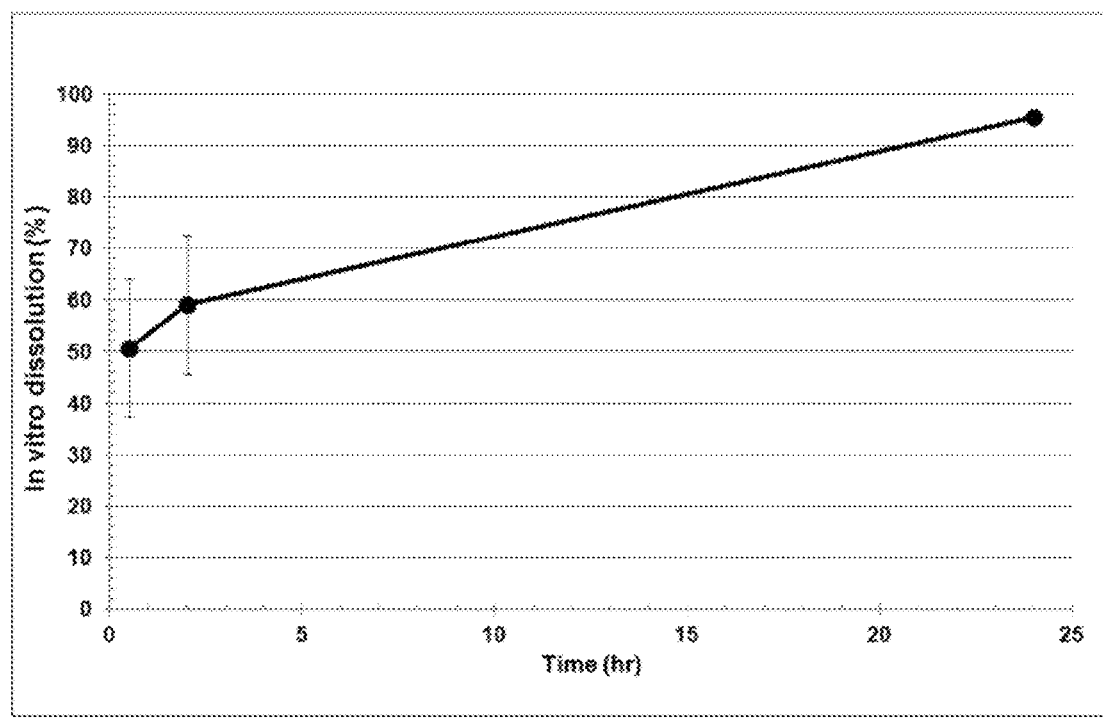
FIG. 6 depicts the mean in-vitro-dissolution of Comparative Example 2.
Figure 7:
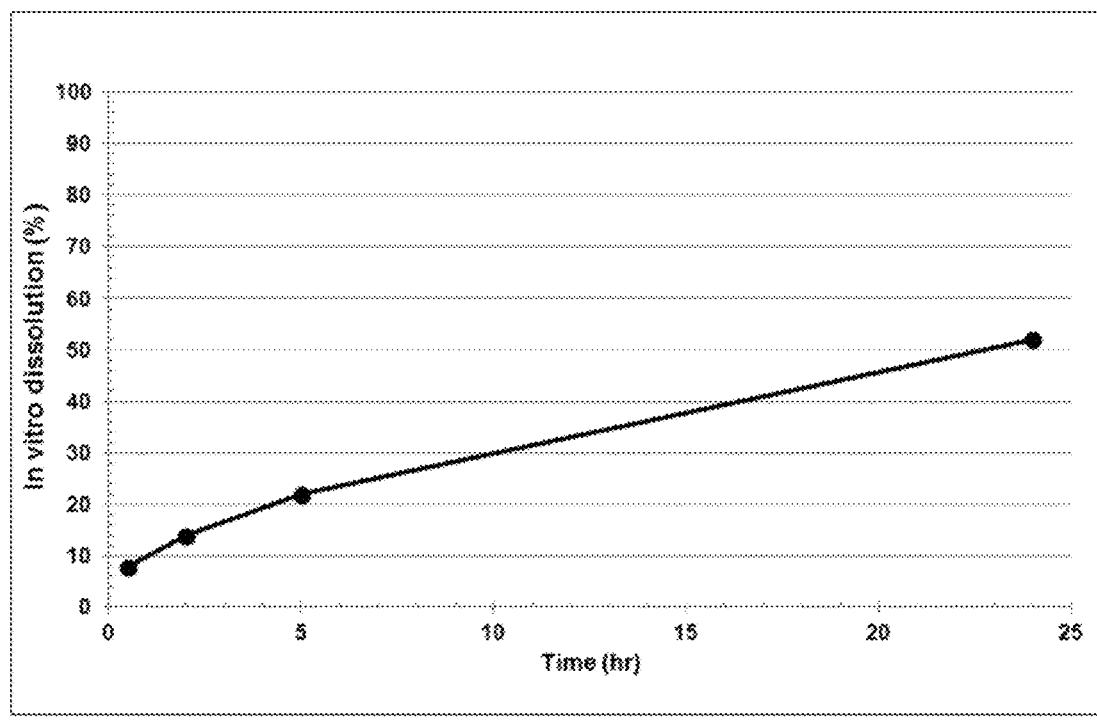
FIG. 7 depicts the mean in-vitro-dissolution of Example 3.
Figure 8:
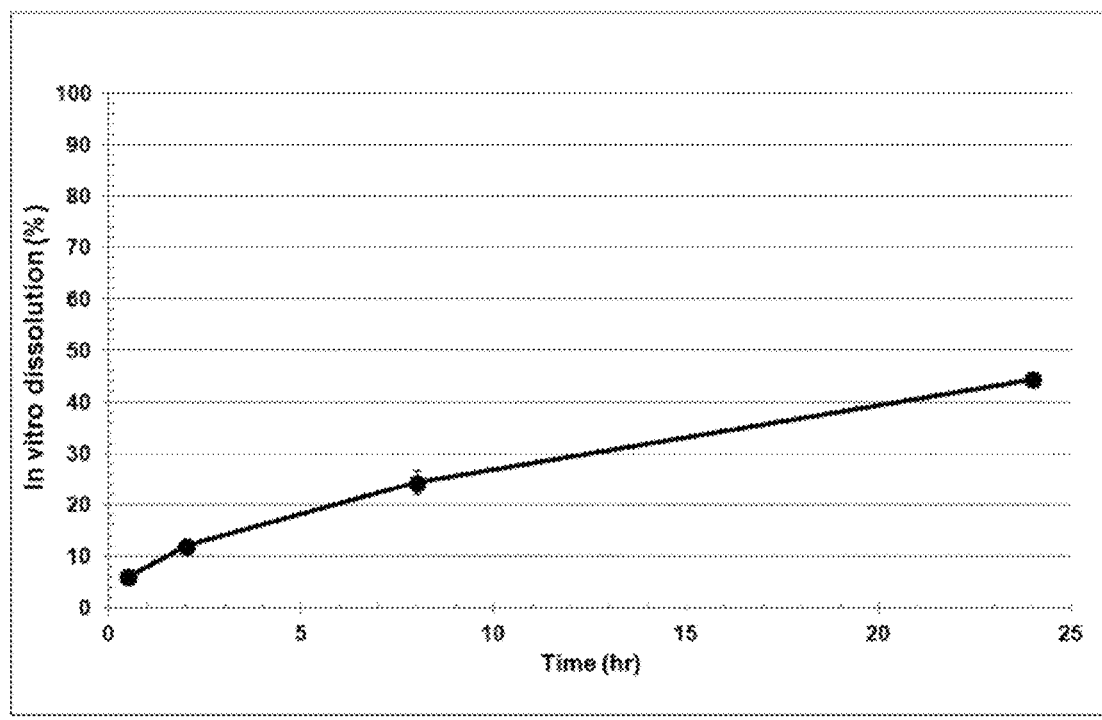
FIG. 8 depicts the mean in-vitro-dissolution of Example 4.

Microscopic pictures were taken of the buprenorphine base-containing adhesive mixture and of the matrix layer using a Nikon S/N 237789 Microscope. FIG. 4A shows a microscopic picture of the buprenorphine base-containing adhesive mixture of Example 4 and FIG. 4B shows a microscopic picture of the matrix layer of Example 4.

Example 5

The composition of the buprenorphine base-containing adhesive mixture and the process of manufacture was as described for Example 4. After the mixing step forming a buprenorphine containing mixture, the buprenorphine base-containing adhesive mixture was additionally homogenized at a homogenizing speed of 2000 rpm-2500 rpm before coated on a polyethylene terephthalate film (e.g. Scotchpak from 3M).

In Example 5, films with two different coating weights of the matrix layer were prepared:

TABLE 5

| Example 5 | Coating weight of the matrix layer [g/m²] |
|---|---|
| Example 5.1 | 120 |
| Example 5.2 | 90 |

Example 6

The composition of the buprenorphine base-containing adhesive mixture is summarized in Table 6 below.

TABLE 6

| Ingredient (Trade Name) | Amt/unit (kg) |
|---|---|
| Buprenorphine base | 1.432 |
| Levulinic acid | 1.002 |
| Polyvinylpyrrolidone | 0.179 |
| Ascorbylacid palmitate | 0.029 |
| Ethanol | 1.014 |
| Polysiloxane adhesive in n-heptane Solids content of 73% by weight (BIO-PSA 7-4201 from Dow Corning Healthcare) | 15.997 |
| n-heptane | 0.346 |
| Total | 20 |

In a 10 l vessel, 1.00 kg of polyvinylpyrrolidone and 3.00 g of ethanol were dissolved to form a 25% PVP pre-solution. In a homogenizing/mixing vessel: Becomix Lab mixer RW 30 Ex, 0.716 kg of PVP pre-solution, 1.002 kg levulinic acid, 0.029 kg of Ascorbyl palmitate and the main part of 0.478 kg of Ethanol were suspended by stirring. The prescribed amount of buprenorphine was weighed and added to the homogenizing/mixing vessel followed by rinsing the weighing container used for buprenorphine with the remaining part of Ethanol. The mixture was kept under stirring for at least 1 h until a buprenorphine containing solution was formed. 15.997 kg of a polysiloxane adhesive in the form of a solution in n-heptane having a solids content of 73% by weight and 0.346 kg of n-heptane were added to the mixing/homogenizing vessel The mixture was stirred for at least 2 h until a buprenorphine-containing adhesive mixture with 7.2% of buprenorphine, with a solids content of 72% (buprenorphine base-containing adhesive mixture) was formed.

Within 24 hours the buprenorphine base-containing adhesive mixture was coated on a polyethylene terephthalate film (e.g. Scotchpak from 3M) using a pilot plant roll coater including a drying tunnel, several drying sections, an unwinding and laminating station. The solvent was removed by drying at approximately 30-50° C. The matrix layer remained within the drying tunnel at approx. 8 minutes. The coating thickness was chosen such that removal of the solvents results in a specific coating weight of 120 g/m².

This results in the 10% by weight of buprenorphine base, 7% by weight of levulinic acid and 1.25% by weight of polyvinylpyrrolidone in this matrix layer. The dried film was laminated with the backing layer (e.g polyethylenterephthalate (PET) foil 19 μm) to provide the buprenorphine-containing self-adhesive layer structure.

The individual systems (TTS) were then punched from the buprenorphine-containing self-adhesive layer structure.

In specific embodiments a TTS as described above can be provided with a further self-adhesive layer of larger surface area, preferably with rounded corners, comprising a pressure-sensitive adhesive matrix layer which is free of active ingredient and has a preferably skin-colored backing layer. This is of advantage when the TTS, on the basis of its physical properties alone, does not adhere sufficiently to the skin and/or when the buprenorphine-containing matrix layer, for the purpose of avoiding waste, has pronounced corners (square or rectangular shapes).

The overtape including the TTS are then punched out by only punching the overtape and sealed into pouches of the primary packaging material.

Example 7

The composition of the buprenorphine base-containing adhesive mixture and the process of manufacture was as described for Example 6. After the mixing step forming a buprenorphine containing mixture, the buprenorphine base-containing adhesive mixture was additionally homogenized at a homogenizing speed of 2000 rpm-2500 rpm before coated on a polyethylene terephthalate film (e.g. Scotchpak from 3M).

In Example 7, films with two different coating weights of the matrix layer were prepared:

TABLE 7

| Example 7 | Coating weight of the matrix layer [g/m$^2$] |
|---|---|
| Example 7.1 | 120 |
| Example 7.2 | 90 |

Example 8

The composition of the buprenorphine base-containing adhesive mixture and the process of manufacture was as described for Example 6. After the mixing step forming a buprenorphine containing mixture, the buprenorphine base-containing adhesive mixture was additionally homogenized at a homogenizing speed of 3500 rpm-4000 rpm before coated on a polyethylene terephthalate film (e.g. Scotchpak from 3M).

Example 9

In Example 9 the in-vitro dissolution of Comparative Examples 1 and 2, and Examples 3 and 4 were determined using the rotating cylinder apparatus of the Ph Eur/USP. The back of the TTS is affixed to the cylinder element using double sided adhesive tape. Following removal of the release liner, the cylinder is lowered into the dissolution medium (600 ml, degassed 0.9% sodium chloride solution at 32° C.) and rotated at 50 rpm. At 0.5, 2, 8 (or 5) and 24 hours, 4 ml samples are removed and analyzed by a reverse phase HPLC method using a mobile phase of 55:45% v/v acetonitrile:0.05 M potassium dihydrogen phosphate (adjusted to pH 3.5) and UV detection at 220 nm. The results are shown in Table 8 and FIGS. 5 to 8.

TABLE 8

| | In vitro dissolution [%] (SD) | | | |
|---|---|---|---|---|
| Elapsed time (hr) | Comparative Example 1 n = 6 | Comparative Example 2 n = 6 | Example 3 n = 6 | Example 4 n = 3 |
| 0 | 0 | 0 | 0 | 0 |
| 0.5 | 15 (0.5) | 51 (13.3) | 8 (0.5) | 6 (0) |
| 2 | 22 (1.0) | 59 (13.5) | 14 (0.8) | 12 (0) |
| 5 | 29 (1.2) | — | 22 (1.1) | — |
| 8 | — | — | — | 24 (2.4) |
| 24 | 51 (1.0) | 95 (8.8) | 52 (1.6) | 44 (1.3) |

Example 10

Figure 9:
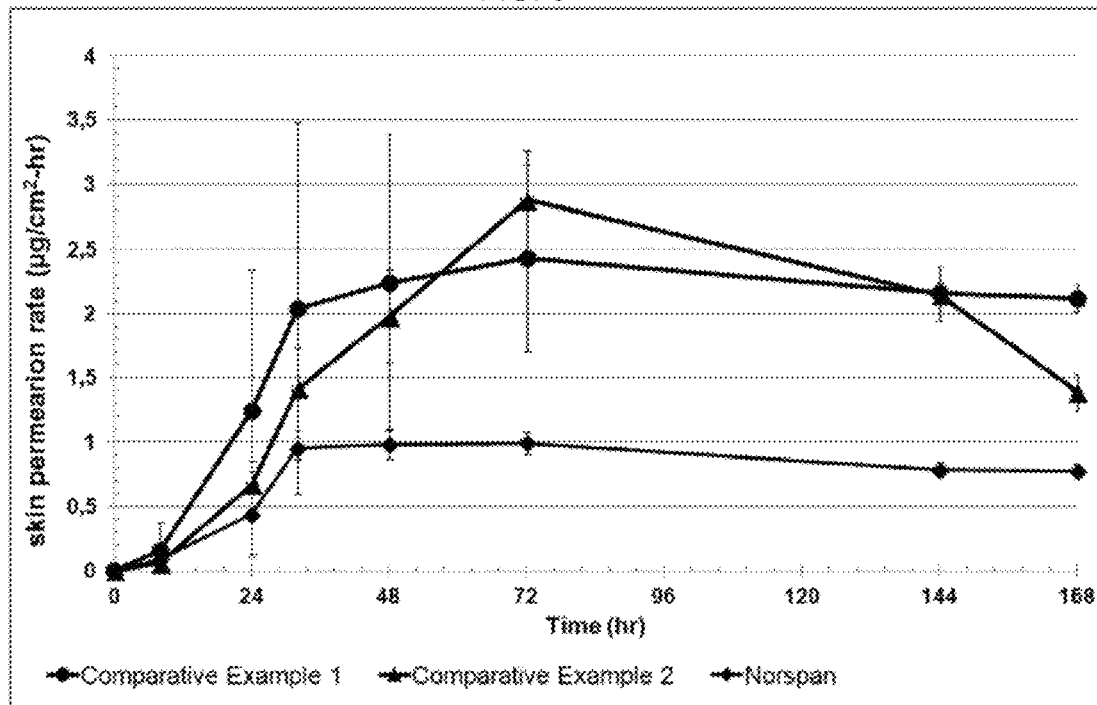
FIG. 9 depicts the mean non-cumulative skin permeation rates for Comparative Examples 1 and 2 and Norspan®.
Figure 10:
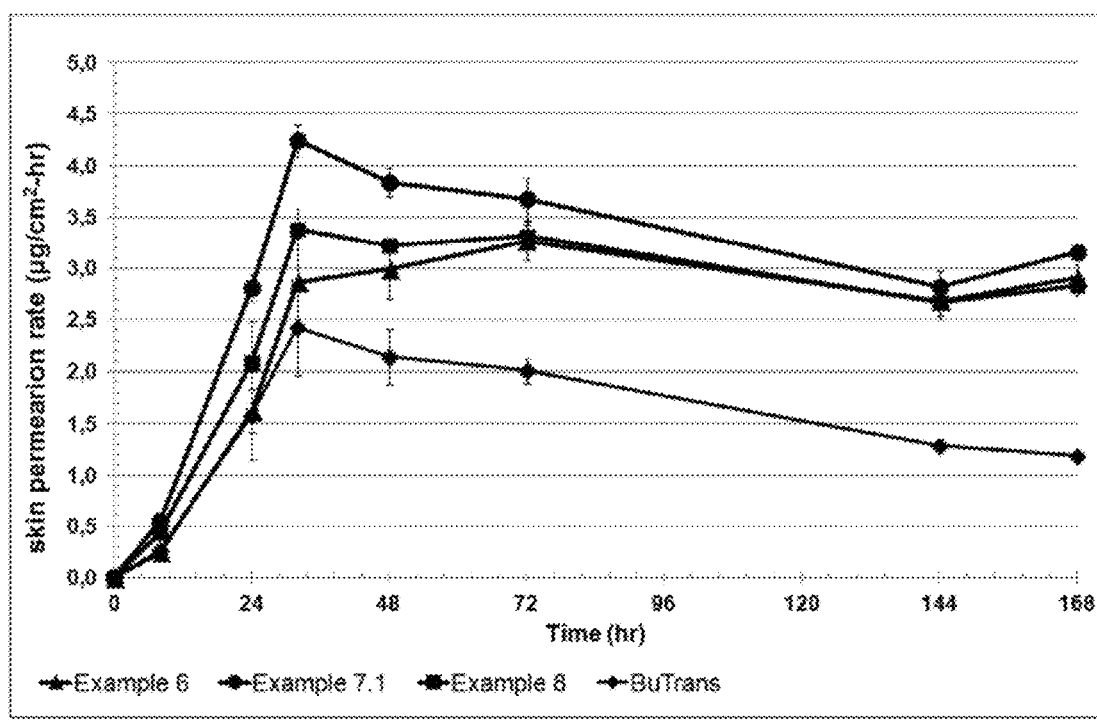
FIG. 10 depicts the mean non-cumulative skin permeation rates for Examples 6, 7.1, 8 and BuTrans®.
Figure 11:
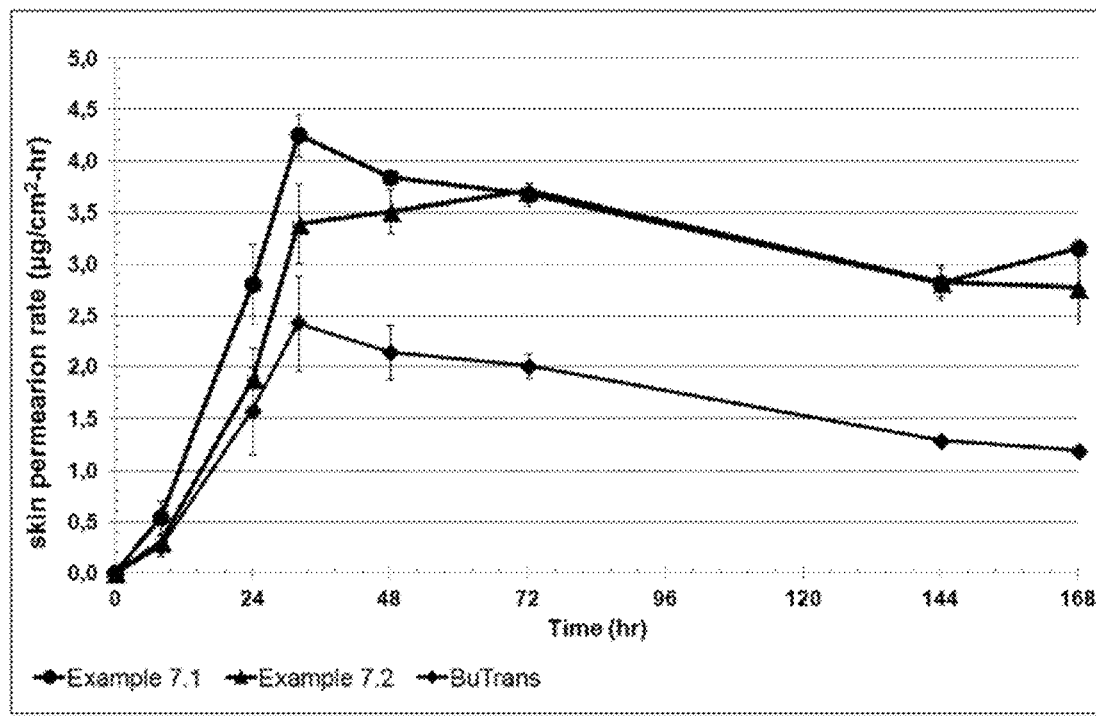
FIG. 11 depicts the mean non-cumulative skin permeation rates for Examples 7.1, 7.2 and BuTrans®.
Figure 12:
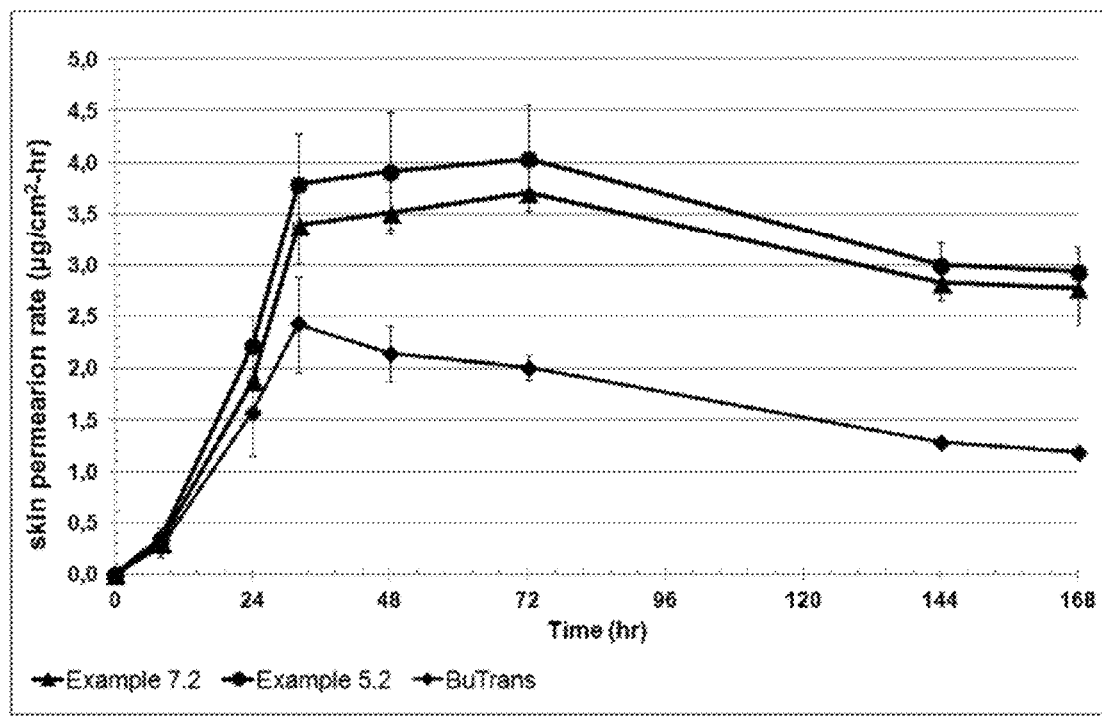
FIG. 12 depicts the mean non-cumulative skin permeation rates for Examples 7.2, 5.2 and BuTrans®.

In Example 10, the in-vitro skin permeation rates of Comparative Examples 1 and 2 and Norspan® were determined by in vitro experiments in accordance with the OECD Guideline (adopted Apr. 13, 2004) carried out with a 9 ml Franz diffusion cell. Split thickness human skin from cosmetic surgeries (female breast, date of birth 1987) was used. A dermatome was used to prepare skin to a thickness of 800 µm, with an intact epidermis for all examples Comparative Examples 1 and 2 and the commercial product Norspan®. Diecuts with an area of 1.163 cm$^2$ were punched from Comparative Examples 1 and 2, and were each tested against diecuts of the commercial product Norspan®. The concentrations of buprenorphine in the receptor medium of the Franz cell (phosphate buffer solution pH 5.5 with 0.1% saline azide as antibacteriological agent) at a temperature of 32±1° C. were measured. The results are shown in Tables 9.1 to 9.4 and FIG. 9.

TABLE 9.1

| | Non-cumulative release [µg/cm$^2$] n = 3 (SD) | | |
|---|---|---|---|
| Elapsed time (hr) | Comparative Example 1 | Comparative Example 2 | Norspan ® |
| 0 | 0 | 0 | 0 |
| 8 | 1.29 (1.71) | 0.48 (0.23) | 0.75 (0.10) |
| 24 | 19.85 (17.70) | 10.75 (2.90) | 7.05 (5.31) |
| 32 | 16.32 (11.50) | 11.27 (2.56) | 7.63 (0.68) |
| 48 | 35.88 (18.39) | 31.67 (5.81) | 15.63 (1.70) |
| 72 | 58.22 (17.37) | 69.03 (9.19) | 23.73 (2.05) |
| 144 | 155.33 (15.27) | 154.67 (6.41) | 56.80 (3.723) |
| 168 | 50.88 (2.60) | 33.28 (3.47) | 18.67 (1.3) |

TABLE 9.2

| | Mean non-cumulative skin permeation rate [µg/cm$^2$-hr] n = 3 (SD) | | |
|---|---|---|---|
| Elapsed time (hr) | Comparative Example 1 | Comparative Example 2 | Norspan ® |
| 0 | 0 | 0 | 0 |
| 8 | 0.16 (0.21) | 0.06 (0.03) | 0.09 (0.01) |
| 24 | 1.24 (1.11) | 0.67 (0.18) | 0.44 (0.33) |
| 32 | 2.04 (1.44) | 1.41 (0.32) | 0.95 (0.08) |
| 48 | 2.24 (1.15) | 1.98 (0.36) | 0.98 (0.11) |
| 72 | 2.43 (0.72) | 2.88 (0.38) | 0.99 (0.09) |
| 144 | 2.16 (0.21) | 2.15 (0.09) | 0.79 (0.05) |
| 168 | 2.12 (0.11) | 1.39 (0.14) | 0.78 (0.05) |

TABLE 9.3

| Cumulative release after 168 hours of release [µg/cm$^2$] n = 3 (SD) | | |
|---|---|---|
| Comparative Example 1 | Comparative Example 2 | Norspan ® |
| 337.83 (82.62) | 311.17 (14.25) | 130.33 (14.05) |

TABLE 9.4

| Mean cumulative skin permeation rate over 168 hours taking into account a lag time of 24 hours [µg/cm$^2$-hr] | | |
|---|---|---|
| Comparative Example 1 | Comparative Example 2 | Norspan ® |
| 2.3 | 2.2 | 0.9 |

Example 11

In Example 11, the in-vitro skin permeation rates of Examples 5 to 8 and BuTrans® were determined by in vitro experiments in accordance with the OECD Guideline (adopted Apr. 13, 2004) carried out with a 9 ml Franz diffusion cell. Split thickness human skin from cosmetic surgeries (female sample of abdomen region, date of birth 1983) was used. A dermatome was used to prepare skin to a thickness of 800 µm, with an intact epidermis for all examples 5 to 8 and the commercial product BuTrans®. Diecuts with an area of 1.163 cm$^2$ were punched from examples 5 to 8, and were each tested against diecuts of the commercial product BuTrans®. The concentrations of buprenorphine in the receptor medium of the Franz cell (phosphate buffer solution pH 5.5 with 0.1% saline azide as antibacteriological agent) at a temperature of 32±1° C. were measured. The results are shown in Tables 10.1 to 10.7 and FIGS. 10 to 13.

TABLE 10.1

Non-cumulative release [µg/cm$^2$] n = 3 (SD)

| Elapsed time (hr) | Example 6.1 | Example 7.1 | Example 8.1 | BuTrans ® |
|---|---|---|---|---|
| 0 | 0 | 0 | 0 | 0 |
| 8 | 1.9 (0.2) | 4.4 (1.3) | 3.5 (0.6) | 2.1 (0.8) |
| 24 | 26.0 (3.4) | 45.0 (6.3) | 33.5 (2.1) | 25.2 (6.8) |
| 32 | 22.9 (3.5) | 34.0 (1.6) | 27.1 (1.3) | 19.4 (3.7) |
| 48 | 47.8 (4.6) | 61.4 (1.1) | 51.6 (2.3) | 34.3 (4.2) |
| 72 | 78.4 (4.6) | 88.3 (2.6) | 79.6 (4.9) | 48.2 (2.8) |
| 144 | 193.3 (13.1) | 203.3 (9.9) | 192.3 (11.0) | 92.7 (3.3) |
| 168 | 69.8 (3.2) | 75.7 (2.4) | 68.0 (1.6) | 28.5 (0.7) |

TABLE 10.2

Non-cumulative release [µg/cm$^2$] n = 3 (SD)

| Elapsed time (hr) | Example 7.2 | Example 5.2 | BuTrans ® |
|---|---|---|---|
| 0 | 0 | 0 | 0 |
| 8 | 2.5 (0.7) | 2.8 (0.8) | 2.1 (0.8) |
| 24 | 30.1 (4.8) | 35.6 (4.6) | 25.2 (6.8) |
| 32 | 27.2 (3.0) | 30.4 (3.9) | 19.4 (3.7) |
| 48 | 56.2 (3.3) | 62.7 (9.1) | 34.3 (4.2) |
| 72 | 89.0 (0.9) | 96.9 (12.3) | 48.2 (2.8) |
| 144 | 203.7 (12.0) | 216.3 (15.6) | 92.7 (3.3) |
| 168 | 66.6 (8.5) | 70.5 (5.7) | 28.5 (0.7) |

TABLE 10.3

Mean non-cumulative skin permeation rate [µg/cm$^2$·hr] n = 3 (SD)

| Elapsed time (hr) | Example 6.1 | Example 7.1 | Example 8.1 | BuTrans ® |
|---|---|---|---|---|
| 0 | 0 | 0 | 0 | 0 |
| 8 | 0.2 (0.0) | 0.5 (0.2) | 0.4 (0.1) | 0.3 (0.1) |
| 24 | 1.6 (0.2) | 2.8 (0.4) | 2.1 (0.1) | 1.6 (0.4) |
| 32 | 2.9 (0.4) | 4.2 (0.2) | 3.4 (0.2) | 2.4 (0.5) |
| 48 | 3.0 (0.3) | 3.8 (0.1) | 3.2 (0.2) | 2.1 (0.3) |
| 72 | 3.3 (0.3) | 3.7 (0.1) | 3.3 (0.2) | 2.0 (0.1) |
| 144 | 2.7 (0.2) | 2.8 (0.1) | 2.7 (0.2) | 1.3 (0.0) |
| 168 | 2.9 (0.1) | 3.2 (0.1) | 2.8 (0.1) | 1.2 (0.0) |

TABLE 10.4

Mean non-cumulative skin permeation rate [µg/cm$^2$·hr] n = 3 (SD)

| Elapsed time (hr) | Example 7.2 | Example 5.2 | BuTrans ® |
|---|---|---|---|
| 0 | 0 | 0 | 0 |
| 8 | 0.3 (0.1) | 0.4 (0.1) | 0.3 (0.1) |
| 24 | 1.9 (0.3) | 2.2 (0.3) | 1.6 (0.4) |
| 32 | 3.4 (0.4) | 3.8 (0.5) | 2.4 (0.5) |
| 48 | 3.5 (0.2) | 3.9 (0.6) | 2.1 (0.3) |
| 72 | 3.7 (0.0) | 4.0 (0.5) | 2.0 (0.1) |
| 144 | 2.8 (0.2) | 3.0 (0.2) | 1.3 (0.0) |
| 168 | 2.8 (0.4) | 2.9 (0.2) | 1.2 (0.0) |

TABLE 10.5

Mean non-cumulative skin permeation rate [µg/cm$^2$·hr] n = 3 (SD) and per area of release [µg/hr]

| Elapsed time (hr) | Sample interval (hr) | Area of release (cm$^2$) | Example 5.2 | BuTrans ® Area of release (25 cm$^2$) |
|---|---|---|---|---|
| 0 | 0 | | 0 | 0 |
| 8 | 8 | | 0.4 (0.1) | 0.3 (0.1) |
| | | 10 | 3.5 | 6.7 |
| | | 14 | 4.9 | 6.7 |
| 24 | 16 | | 2.2 (0.3) | 1.6 (0.4) |
| | | 10 | 22.2 | 39.4 |
| | | 14 | 31.1 | 39.4 |
| 32 | 8 | | 3.8 (0.5) | 2.4 (0.5) |
| | | 10 | 38.0 | 60.7 |
| | | 14 | 53.1 | 60.7 |
| 48 | 16 | | 3.9 (0.6) | 2.1 (0.3) |
| | | 10 | 39.2 | 53.6 |
| | | 14 | 54.8 | 53.6 |
| 72 | 24 | | 4.0 (0.5) | 2.0 (0.1) |
| | | 10 | 40.4 | 50.2 |
| | | 14 | 56.5 | 50.2 |
| 144 | 72 | | 3.0 (0.2) | 1.3 (0.0) |
| | | 10 | 30.0 | 32.2 |
| | | 14 | 42.1 | 32.2 |
| 168 | 24 | | 2.9 (0.2) | 1.2 (0.0) |
| | | 10 | 29.4 | 29.7 |
| | | 14 | 41.1 | 29.7 |

TABLE 10.6

Cumulative release after 168 hours of release [µg/cm$^2$] n = 3 (SD)

| Example 5.2 | BuTrans ® |
|---|---|
| 515.3 (44.1) | 250.7 (17.1) |

TABLE 10.7

Mean cumulative skin permeation rate over 168 hours taking into account a lag time of 24 hours [µg/cm$^2$·hr]

| Example 5.2 | BuTrans ® |
|---|---|
| 3.6 | 1.7 |

The invention claimed is:

1. A transdermal therapeutic system for transdermal administration of buprenorphine, comprising a buprenorphine-containing self-adhesive layer structure comprising
   A) a buprenorphine-impermeable backing layer, and
   B) a buprenorphine-containing pressure-sensitive adhesive layer on said buprenorphine-impermeable backing layer, said adhesive layer comprising
      at least one polymer-based pressure-sensitive adhesive based on polysiloxanes,
      an analgesically effective amount of buprenorphine comprising buprenorphine base or a pharmaceutically acceptable salt thereof,
      a viscosity-increasing substance in an amount of about 0.1% to about 8% of said buprenorphine-containing pressure-sensitive adhesive layer, wherein the viscosity-increasing substance comprises polyvinylpyrrolidone, and
      a carboxylic acid comprising levulinic acid, in an amount sufficient so that said analgesically effective amount of buprenorphine is solubilized therein to form a mixture including said viscosity-increasing substance, and wherein said carboxylic acid-, buprenorphine- and viscosity-increasing substance-containing mixture forms dispersed deposits in said pressure-sensitive adhesive, and wherein said buprenorphine-containing pressure-sensitive adhesive layer is the skin contact layer.

2. The transdermal therapeutic system of claim 1, wherein said buprenorphine-comprises buprenorphine base.

3. The transdermal therapeutic system of claim 1, wherein said polyvinylpyrrolidone is present in an amount of about 0.1% to about 7%, or of about 0.5% to about 5%, or of about 1% to about 4%, or of about 2% to about 3% of said buprenorphine-containing pressure-sensitive adhesive layer.

4. The transdermal therapeutic system of claim 1, wherein said polyvinylpyrrolidone is present in an amount of about 0.1% to about 7%.

5. The transdermal therapeutic system of claim 1, wherein said polyvinylpyrrolidone has a K-Value of at least about 5, or of at least about 10, or of at least about 15, or of at least about 20, or of at least about 50, or of at least about 80.

6. The transdermal therapeutic system of claim 1, wherein the polyvinylpyrrolidone has a K-Value of at least about 80.

7. The transdermal therapeutic system of claim 1, wherein said buprenorphine comprises buprenorphine base and said polyvinylpyrrolidone is present in an amount of about 1% to about 4%.

8. The transdermal therapeutic system of claim 1, wherein said amount of said buprenorphine contained in the transdermal therapeutic system ranges from about 1 mg to about 4 mg buprenorphine base or an equimolar amount of the pharmaceutically acceptable salt thereof, or about 3.5 mg to about 8 mg buprenorphine base or an equimolar amount of the pharmaceutically acceptable salt thereof, or about 6.5 mg to about 16 mg buprenorphine base or an equimolar amount of the pharmaceutically acceptable salt thereof, or about 11.5 mg to about 24 mg buprenorphine base or an equimolar amount of the pharmaceutically acceptable salt thereof, or about 15 mg to about 32 mg buprenorphine base or an equimolar amount of the pharmaceutically acceptable salt thereof.

9. The transdermal therapeutic system of claim 1, wherein said buprenorphine-containing pressure-sensitive adhesive layer has a size that provides an area of release ranging from about 1 $cm^2$ to about 4.8 $cm^2$, or
about 3 $cm^2$ to about 9.5 $cm^2$, or
about 6 $cm^2$ to about 19 $cm^2$, or
about 12 $cm^2$ to about 28.5 $cm^2$, or
about 16 $cm^2$ to about 38 $cm^2$.

10. The transdermal therapeutic system of claim 1, wherein said buprenorphine-containing pressure-sensitive adhesive layer has a size that provides an area of release ranging from about 1 $cm^2$ to about 4.8 $cm^2$ and said amount of said buprenorphine contained in the transdermal therapeutic system ranges from about 1 mg to about 4 mg buprenorphine base or an equimolar amount of the pharmaceutically acceptable salt thereof, wherein said transdermal therapeutic system provides a nominal mean release rate of about 5 μg/hr over about 168 hours of administration.

11. The transdermal therapeutic system of claim 1, wherein said buprenorphine-containing pressure-sensitive adhesive layer has a size that provides an area of release ranging from about 3 $cm^2$ to about 9.5 $cm^2$, and said amount of said buprenorphine contained in the transdermal therapeutic system ranges from about 3.5 mg to about 8 mg buprenorphine base or an equimolar amount of the pharmaceutically acceptable salt thereof, wherein said transdermal therapeutic system provides a nominal mean release rate of about 10 μg/hr over about 168 hours of administration.

12. The transdermal therapeutic system of claim 1, wherein said buprenorphine-containing pressure-sensitive adhesive layer has a size that provides an area of release ranging from about 6 $cm^2$ to about 19 $cm^2$ and said amount of said buprenorphine contained in the transdermal therapeutic system ranges from about 6.5 mg to about 16 mg buprenorphine base or an equimolar amount of the pharmaceutically acceptable salt thereof, wherein said transdermal therapeutic system provides a nominal mean release rate of about 20 μg/hr over about 168 hours of administration.

13. The transdermal therapeutic system of claim 1, wherein said buprenorphine-containing pressure-sensitive adhesive layer has a size that provides an area of release ranging from about 12 $cm^2$ to about 28.5 $cm^2$, and said amount of said buprenorphine contained in the transdermal therapeutic system ranges from about 11.5 mg to about 24 mg buprenorphine base or an equimolar amount of the pharmaceutically acceptable salt thereof, wherein said transdermal therapeutic system provides a nominal mean release rate of about 30 μg/hr over about 168 hours of administration.

14. The transdermal therapeutic system of claim 1, wherein said buprenorphine-containing pressure-sensitive adhesive layer has a size that provides an area of release ranging from about 16 $cm^2$ to about 38 $cm^2$, and said amount of said buprenorphine contained in the transdermal therapeutic system ranges from about 15 mg to about 32 mg buprenorphine base or an equimolar amount of the pharmaceutically acceptable salt thereof, wherein said transdermal therapeutic system provides a nominal mean release rate of about 40 μg/hr over about 168 hours of administration.

15. The transdermal therapeutic system of claim 1, wherein said buprenorphine comprises buprenorphine base and said system provides a mean cumulative skin permeation rate measured in a Franz diffusion cell with dermatomed human skin of more than 1.3 μg/$cm^2$-hr over a 168 hours test and/or provides a cumulative release of buprenorphine base as measured in a Franz diffusion cell with dermatomed human skin of 220 μg/$cm^2$ to 640 μg/$cm^2$ over a time period of 168 hours.

16. The transdermal therapeutic system of claim 1, wherein said buprenorphine comprises buprenorphine base and said system provides a non-cumulative release of buprenorphine base as measured in a Franz diffusion cell with dermatomed human skin of 2 μg/$cm^2$ to 10 μg/$cm^2$ in the first 8 hours,
20 μg/$cm^2$ to 80 μg/$cm^2$ from hour 8 to hour 24,
20 μg/$cm^2$ to 80 μg/$cm^2$ from hour 24 to hour 32,
30 μg/$cm^2$ to 120 μg/$cm^2$ from hour 32 to hour 48,
40 μg/$cm^2$ to 150 μg/$cm^2$ from hour 48 to hour 72,
100 μg/$cm^2$ to 300 μg/$cm^2$ from hour 72 to hour 144, and
30 μg/$cm^2$ to 100 μg/$cm^2$ from hour 144 to hour 168.

17. The transdermal therapeutic system of claim 1, wherein said transdermal therapeutic system provides a mean AUCt per area of release of more than 1,700 pg·hr/ml-$cm^2$ over about 168 hours of administration after a single-dose administration to a subject population.

18. The transdermal therapeutic system of claim 1, wherein said buprenorphine base-containing pressure-sensitive adhesive layer comprises an anti-oxidant selected from the group consisting of ascorbyl palmitate, tocopherol and esters thereof, ascorbic acid, butylhydroxytoluene, butylhydroxyanisole, propyl gallate and mixtures thereof.

19. The transdermal therapeutic system of claim 18, wherein said anti-oxidant is ascorbyl palmitate and is present in an amount of from about 0.01 to about 0.5% of said buprenorphine-containing pressure-sensitive adhesive layer.

20. A set of two to five different transdermal therapeutic systems each in accordance with claim 1, wherein
said first transdermal therapeutic system provides a size of said buprenorphine-containing pressure-sensitive adhesive layer providing an area of release ranging from about 1 $cm^2$ to about 4.8 $cm^2$ and contains an amount of said buprenorphine from about 1 mg to about 4 mg buprenorphine base or an equimolar amount of a pharmaceutically acceptable salt thereof;
said second transdermal therapeutic system provides a size of said buprenorphine-containing pressure-sensitive adhesive layer providing an area of release ranging from about 3 $cm^2$ to about 9.5 $cm^2$ and contains an amount of said buprenorphine from about 3.5 mg to about 8 mg buprenorphine base or an equimolar amount of a pharmaceutically acceptable salt thereof;
said third transdermal therapeutic system provides a size of said buprenorphine-containing pressure-sensitive adhesive layer providing an area of release ranging from about 6 $cm^2$ to about 19 $cm^2$ and contains an amount of said buprenorphine from about 6.5 mg to about 16 mg buprenorphine base or an equimolar amount of a pharmaceutically acceptable salt thereof;
said fourth transdermal therapeutic system provides a size of said buprenorphine-containing pressure-sensitive adhesive layer providing an area of release ranging from about 12 $cm^2$ to about 28.5 $cm^2$ and contains an amount of said buprenorphine from about 11.5 mg to about 24 mg buprenorphine base or an equimolar amount of a pharmaceutically acceptable salt thereof; and
said fifth transdermal therapeutic system provides a size of said buprenorphine-containing pressure-sensitive adhesive layer providing an area of release ranging from about 16 $cm^2$ to about 38 $cm^2$ and contains an amount of said buprenorphine from about 15 mg to about 32 mg buprenorphine base or an equimolar amount of a pharmaceutically acceptable salt thereof.

21. A transdermal therapeutic system for transdermal administration of buprenorphine, comprising a buprenorphine-containing self-adhesive layer structure comprising
A) a buprenorphine-impermeable backing layer, and
B) a buprenorphine-containing pressure-sensitive adhesive layer on said buprenorphine-impermeable backing layer, said adhesive layer comprising
a) at least one polymer-based pressure-sensitive adhesive based on polysiloxanes or polyisobutylenes,
b) an analgesically effective amount of buprenorphine base or a pharmaceutically acceptable salt thereof,
c) a viscosity-increasing substance in an amount of about 0.1% to about 8% of said buprenorphine-containing pressure-sensitive adhesive layer, wherein the viscosity-increasing substance is polyvinylpyrrolidone, and
d) a carboxylic acid selected from the group consisting of oleic acid, linoleic acid, linolenic acid, levulinic acid and mixtures thereof, in an amount sufficient so that said analgesically effective amount of buprenorphine is solubilized therein to form a mixture including said viscosity-increasing substance, and wherein said carboxylic acid-, buprenorphine- and viscosity-increasing substance-containing mixture forms dispersed deposits in said pressure-sensitive adhesive, and
wherein said buprenorphine-containing pressure-sensitive adhesive layer is the skin contact layer.

22. The transdermal therapeutic system of claim 21, wherein said buprenorphine is present in the form of buprenorphine base and/or wherein said carboxylic acid is levulinic acid.

23. The transdermal therapeutic system of claim 21, wherein said buprenorphine is present in the form of buprenorphine base, said carboxylic acid is levulinic acid and said polymer-based pressure-sensitive adhesive is based on polysiloxanes.

24. The transdermal therapeutic system of claim 21, wherein said polyvinylpyrrolidone is present in an amount of about 0.1% to about 7%, or of about 0.5% to about 5%, or of about 1% to about 4%, or of about 2% to about 3% of said buprenorphine-containing pressure-sensitive adhesive layer.

25. The transdermal therapeutic system of claim 21, wherein the polyvinylpyrrolidone has a K-Value of at least about 80.

26. The transdermal therapeutic system of claim 21, wherein said buprenorphine is present in the form of buprenorphine base, said carboxylic acid is levulinic acid, said polymer-based pressure-sensitive adhesive is based on polysiloxanes and said polyvinylpyrrolidone in an amount of about 1% to about 4%.

27. The transdermal therapeutic system of claim 21, wherein said amount of said buprenorphine contained in the transdermal therapeutic system ranges from about 1 mg to about 4 mg buprenorphine base or an equimolar amount of the pharmaceutically acceptable salt thereof, or
about 3.5 mg to about 8 mg buprenorphine base or an equimolar amount of the pharmaceutically acceptable salt thereof, or
about 6.5 mg to about 16 mg buprenorphine base or an equimolar amount of the pharmaceutically acceptable salt thereof, or
about 11.5 mg to about 24 mg buprenorphine base or an equimolar amount of the pharmaceutically acceptable salt thereof, or
about 15 mg to about 32 mg buprenorphine base or an equimolar amount of the pharmaceutically acceptable salt thereof.

28. The transdermal therapeutic system of claim 21, wherein said buprenorphine-containing pressure-sensitive adhesive layer has a size that provides an area of release ranging from
about 1 $cm^2$ to about 4.8 $cm^2$, or
about 3 $cm^2$ to about 9.5 $cm^2$, or
about 6 $cm^2$ to about 19 $cm^2$, or
about 12 $cm^2$ to about 28.5 $cm^2$, or
about 16 $cm^2$ to about 38 $cm^2$.

29. The transdermal therapeutic system of claim 21, wherein said buprenorphine-containing pressure-sensitive adhesive layer has a size that provides an area of release ranging from about 1 $cm^2$ to about 4.8 $cm^2$ and said amount of said buprenorphine contained in the transdermal therapeutic system ranges from about 1 mg to about 4 mg buprenorphine base or an equimolar amount of the pharmaceutically acceptable salt thereof,
wherein said transdermal therapeutic system provides a nominal mean release rate of about 5 μg/hr over about 168 hours of administration.

30. The transdermal therapeutic system of claim 21, wherein said buprenorphine-containing pressure-sensitive adhesive layer has a size that provides an area of release ranging from about 3 cm² to about 9.5 cm², and said amount of said buprenorphine contained in the transdermal therapeutic system ranges from about 3.5 mg to about 8 mg buprenorphine base or an equimolar amount of the pharmaceutically acceptable salt thereof,
wherein said transdermal therapeutic system provides a nominal mean release rate of about 10 μg/hr over about 168 hours of administration.

31. The transdermal therapeutic system of claim 21, wherein said buprenorphine-containing pressure-sensitive adhesive layer has a size that provides an area of release ranging from about 6 cm² to about 19 cm² and said amount of said buprenorphine contained in the transdermal therapeutic system ranges from about 6.5 mg to about 16 mg buprenorphine base or an equimolar amount of the pharmaceutically acceptable salt thereof, wherein said transdermal therapeutic system provides a nominal mean release rate of about 20 μg/hr over about 168 hours of administration.

32. The transdermal therapeutic system of claim 21, wherein said buprenorphine-containing pressure-sensitive adhesive layer has a size that provides an area of release ranging from about 12 cm² to about 28.5 cm², and said amount of said buprenorphine contained in the transdermal therapeutic system ranges from about 11.5 mg to about 24 mg buprenorphine base or an equimolar amount of the pharmaceutically acceptable salt thereof, wherein said transdermal therapeutic system provides a nominal mean release rate of about 30 μg/hr over about 168 hours of administration.

33. The transdermal therapeutic system of claim 21, wherein said buprenorphine-containing pressure-sensitive adhesive layer has a size that provides an area of release ranging from about 16 cm² to about 38 cm², and said amount of said buprenorphine contained in the transdermal therapeutic system ranges from about 15 mg to about 32 mg buprenorphine base or an equimolar amount of the pharmaceutically acceptable salt thereof, wherein said transdermal therapeutic system provides a nominal mean release rate of about 40 μg/hr over about 168 hours of administration.

34. The transdermal therapeutic system of claim 21, wherein said buprenorphine is present in the form of buprenorphine base and said system provides a mean cumulative skin permeation rate measured in a Franz diffusion cell with dermatomed human skin of more than 1.3 μg/cm²-hr over a 168 hours test and/or provides a cumulative release of buprenorphine base as measured in a Franz diffusion cell with dermatomed human skin of 220 μg/cm² to 640 μg/cm² over a time period of 168 hours.

35. The transdermal therapeutic system of claim 21, wherein said buprenorphine is present in the form of buprenorphine base and said system provides a non-cumulative release of buprenorphine base as measured in a Franz diffusion cell with dermatomed human skin of
2 μg/cm² to 10 μg/cm² in the first 8 hours,
20 μg/cm² to 80 μg/cm² from hour 8 to hour 24,
20 μg/cm² to 80 μg/cm² from hour 24 to hour 32,
30 μg/cm² to 120 μg/cm² from hour 32 to hour 48,
40 μg/cm² to 150 μg/cm² from hour 48 to hour 72,
100 μg/cm² to 300 μg/cm² from hour 72 to hour 144, and
30 μg/cm² to 100 μg/cm² from hour 144 to hour 168.

36. The transdermal therapeutic system of claim 21, wherein said transdermal therapeutic system provides a mean AUCt per area of release of more than 1,700 pg·hr/ml-cm² over about 168 hours of administration after a single-dose administration to a subject population.

37. The transdermal therapeutic system of claim 21, wherein said buprenorphine base-containing pressure-sensitive adhesive layer comprises an anti-oxidant selected from the group consisting of ascorbyl palmitate, tocopherol and esters thereof, ascorbic acid, butylhydroxytoluene, butylhydroxyanisole, propyl gallate and mixtures thereof.

38. The transdermal therapeutic system of claim 37, wherein said anti-oxidant is ascorbyl palmitate and is present in an amount of from about 0.01 to about 0.5% of said buprenorphine-containing pressure-sensitive adhesive layer.

39. A method of treating pain in a patient comprising applying the transdermal therapeutic system of claim 21 to the skin of said patient.

40. The method claim 39, wherein said transdermal therapeutic system is applied on the skin of the patient for about 168 hours.

41. The method of claim 39, wherein said buprenorphine is present in the form of buprenorphine base and/or wherein said carboxylic acid is levulinic acid.

42. The method of claim 39, wherein said buprenorphine is present in the form of buprenorphine base, said carboxylic acid is levulinic acid and said polymer-based pressure-sensitive adhesive is based on polysiloxanes.

43. The method of claim 39, wherein the polyvinylpyrrolidone has a K-Value of at least about 80.

44. The method of claim 39, wherein said buprenorphine is present in the form of buprenorphine base, said carboxylic acid is levulinic acid, said polymer-based pressure-sensitive adhesive is based on polysiloxanes and said polyvinylpyrrolidone in an amount of about 1% to about 4%.

45. The method of claim 39, wherein said transdermal therapeutic system provides a mean AUCt per area of release of more than 1,700 pg·hr/ml-cm² over about 168 hours of administration after a single-dose administration to a subject population.

46. The transdermal therapeutic system of claim 21, wherein the polyvinylpyrrolidone comprises soluble polyvinylpyrrolidone.

47. The transdermal therapeutic system of claim 21, wherein the polyvinylpyrrolidone has a K-Value of at least about 5, or of at least about 10, or of at least about 15, or of at least about 20, or of at least about 50, or of at least about 80.

48. A set of two to five different transdermal therapeutic systems each in accordance with claim 21, wherein
said first transdermal therapeutic system provides a size of said buprenorphine-containing pressure-sensitive adhesive layer providing an area of release ranging from about 1 cm² to about 4.8 cm² and contains an amount of said buprenorphine from about 1 mg to about 4 mg buprenorphine base or an equimolar amount of a pharmaceutically acceptable salt thereof;
said second transdermal therapeutic system provides a size of said buprenorphine-containing pressure-sensitive adhesive layer providing an area of release ranging from about 3 cm² to about 9.5 cm² and contains an amount of said buprenorphine from about 3.5 mg to about 8 mg buprenorphine base or an equimolar amount of a pharmaceutically acceptable salt thereof;
said third transdermal therapeutic system provides a size of said buprenorphine-containing pressure-sensitive adhesive layer providing an area of release ranging from about 6 cm² to about 19 cm² and contains an amount of said buprenorphine from about 6.5 mg to about 16 mg buprenorphine base or an equimolar amount of a pharmaceutically acceptable salt thereof;

said fourth transdermal therapeutic system provides a size of said buprenorphine-containing pressure-sensitive adhesive layer providing an area of release ranging from about 12 cm² to about 28.5 cm² and contains an amount of said buprenorphine from about 11.5 mg to about 24 mg buprenorphine base or an equimolar amount of a pharmaceutically acceptable salt thereof; and said fifth transdermal therapeutic system provides a size of said buprenorphine-containing pressure-sensitive adhesive layer providing an area of release ranging from about 16 cm² to about 38 cm² and contains an amount of said buprenorphine from about 15 mg to about 32 mg buprenorphine base or an equimolar amount of a pharmaceutically acceptable salt thereof.

* * * * *